US007090842B1

(12) United States Patent
Chatterjee et al.

(10) Patent No.: US 7,090,842 B1

(45) Date of Patent: Aug. 15, 2006

(54) MURINE MONOCLONAL ANTI-IDIOTYPE ANTIBODY 3H1 SEQUENCES FOR HUMAN CARCINOEMBRYONIC ANTIGEN

(75) Inventors: Malaya Chatterjee, Lexington, KY (US); Heinz Kohler, Lexington, KY (US); Sunil K. Chatterjee, Lexington, KY (US); Kenneth A. Foon, Lexington, KY (US)

(73) Assignee: Board of Trustees of the University of Kentucky, Lexington, KY (US)

( * ) Notice: Subject to any disclaimer, the term of this patent is extended or adjusted under 35 U.S.C. 154(b) by 0 days.

(21) Appl. No.: 08/579,916

(22) Filed: Dec. 28, 1995

Related U.S. Application Data

(63) Continuation-in-part of application No. 08/365,484, filed on Dec. 28, 1994, now abandoned.

(51) Int. Cl.
*A61K 39/395* (2006.01)

(52) U.S. Cl. .............................. 424/131.1; 424/130.1; 424/133.1; 424/134.1; 424/138.1; 424/139.1; 424/141.1; 435/7.1; 530/387.1; 530/387.2; 530/387.3; 530/687.7; 530/388.1

(58) Field of Classification Search ................ 530/376, 530/387.1, 387.2, 387.3, 387.7, 388.1; 435/7.1, 435/7.7; 424/130.1, 131.1, 133.1, 134.1, 424/138.1, 139.1, 141.1
See application file for complete search history.

(56) References Cited

U.S. PATENT DOCUMENTS 3,996,345 A 12/1976 Ullman et al.
4,436,728 A 3/1984 Ribi et al.
4,474,893 A * 10/1984 Reading ..................... 436/547
4,722,840 A 2/1988 Valenzuela et al.
4,722,899 A * 2/1988 Hamaoka et al. ........ 435/172.2
4,726,947 A 2/1988 Shimada et al.
4,828,991 A 5/1989 Hanna, Jr. et al.
5,051,335 A 9/1991 Yoshida et al.
5,053,224 A 10/1991 Koprowski et al.
5,057,540 A 10/1991 Kensil et al.
5,077,284 A 12/1991 Loria et al.
5,106,738 A 4/1992 Hanna, Jr. et al.
5,160,723 A 11/1992 Welt et al.
5,171,568 A 12/1992 Burke et al.
5,180,814 A 1/1993 Hanna, Jr. et al.
5,183,756 A 2/1993 Schlom
5,200,316 A 4/1993 Elting et al.
5,227,471 A 7/1993 Wright, Jr.
5,244,801 A 9/1993 Tobi
5,407,684 A 4/1995 Loria et al.
5,585,089 A * 12/1996 Queen et al. ............ 424/133.1
5,608,039 A * 3/1997 Pastan et al. ............ 530/387.3
5,977,315 A * 11/1999 Chatterjee et al. ....... 530/387.2

FOREIGN PATENT DOCUMENTS

| | | | |
|---|---|---|---|
| EP | 0 141 783 | | 5/1985 |
| EP | 0329400 | | 8/1989 |
| EP | 0 438 803 | | 7/1991 |
| GB | 02017 | * | 7/1991 |
| GB | WO 91/09967 | * | 7/1991 |
| WO | WO 89/11537 | | 11/1989 |
| WO | WO 91/11465 | | 8/1991 |
| WO | WO 91/16924 | | 11/1991 |
| WO | WO 92/16231 | | 10/1992 |
| WO | WO 93/06233 | | 4/1993 |
| WO | WO 94/05329 | | 3/1994 |

OTHER PUBLICATIONS

Chatterjee et al. (1990) J. Immunol. 145:2758-65, Oct. 15, 1990.*
Sambrook et al. (1989) molecular Cloning, A Laboratory Manual; Cold Spr. Harbor Lab. Press.*
Cheetham et al Prot Engineering vol. 2(3) 170-172, 1988.*
Rudikoff et al Proc Natl Acad Sci USA vol. 79 1979, 1982.*
Panka et al Proc Natl Acad Sci USA vol. 85 3080-3084, May 1988.*
Seaver Genetic Engineering News vol. 14 No. 14 pp. 10 and 21, 1994.*
Seveir et al Clin Chem vol. 27 No. 11 1797-1806, 1981.*
Browning Cell vol. 72 847-857, Mar. 1993.*
Lewin Science vol. 237 1570, 1987.*
Reeck Cell vol. 50 667, 1987.*
Paul Fundamental Immunology p. 242, 1993.*
Taub, R et al. JBC, 264(1): 259-265, 1989.*
Stites, DP. Medical Immunology Appleton & Lange, Stamford, Connecticut, p. 51-52, 1997.*
Herbert et al., The Dictionary of Immunology A.P., 4th ed., p. 58, 1995.*
MPSRCH search report, 2003, us-08-579-916c48.rag, p. 6-8.*
Youvan, R et al, 1985, TichyR et al, 1989, or Tadros, R et al, 1985, GenBank Accession No: A21901, A33958, A22258, respectively, and MPSRCH search report, 2003, us-08-579-916c-48.rpr, p. 1-2.*
WO9321225-A, Accession No: AAR43352, and MPSRCH search report, 2003, us-08-579-916c-48.rag, p. 7.*
Roitt et al, 1998, Immunology, 4th ed, Mosby, London, p. 7.7-7.8.*
Holmes (Exp. Opin.Invest. Drugs, 2001, 10(3):511-519).*

(Continued)

*Primary Examiner*—Susan Ungar
*Assistant Examiner*—Minh-Tam Davis
(74) *Attorney, Agent, or Firm*—Morrison & Foerster LLP

(57) ABSTRACT

This invention provides compositions derived from the sequences encoding the variable light and/or variable heavy regions of monoclonal anti-idiotype antibody 3H1 and methods for using these compositions.

19 Claims, 32 Drawing Sheets

OTHER PUBLICATIONS

Bird et al, 1988, Science, 242: 423-426.*
Savage P, British Journal of Cancer, 1993, V68, N4 (Oct), p. 738-742.*
Posnett et al, 1988, J Biol Chem, 263: 1719-1725.*
Tam, 1989, Method Enz. 168: 7-15.*
Bowie et al (Science, 1990, 257 : 1306-1310).*
Roger, I et al, 1988, Bioscience Reports, 8(4):359-368.*
Stites, DP et al, eds, 1997, Medical Immunology, 9th ed, Appleton & Lange, Stamford, Connecticut, pp. 846-847.*
Takeda S et al, Nature (ENGLAND) Apr. 4-10, 1985, 314 (6010) p. 452-4.*
Gaida ret al., (1992), "A monoclonal anti-idiotypic antibody bearing the image of an epitope specific to the human carcinoembryonic antigen," *Int. J. Cancer* 51(3), 459-465.
Moraes et al., (1992) "Induction of an immune response through the idiotypic network with monoclonal anti-idiotype antibodies in the carcinoembryonic antigen system," *J. Cell Biochem* 50(3), 324-335.
Lindenmann, "Speculations on idiotypes and homobodies" *Annales D'Immunologie* (1973) 124C:171-184.
Jerne, "Towards a network theory of the immune system" *Ann. Immunol.* (1974) 125 C:373-389.
Herlyn et al., "Anti-idiotype immunization of cancer patients: Modulation of the immune response" *Proc. Natl. Acad. Sci. USA* (1987) 84:8055-8059.
Mittleman et al., "Human high molecular weight melanoma-associated antigen (HMW-MAA) mimicry by mouse anti-idiotypic monoclonal antibody MK2-23: Induction of humoral anti-HMW-MAA immunity and prolongation of survival in patients with stage IV melanoma" *Proc. Natl. Acad. Sci. USA* (1992) 89:466-470.
Chatterjee et al., "Antiidiotype (Ab2) vaccine therapy for cutaneous T-cell lymphoma" *Ann. N.Y. Acad. Sci.* (1993) 690:376-377.
Hansen et al., "Characterization of second-generation monoclonal antibodies against carcinoembryonic antigen" *Cancer* (1993) 71:3478-385.
Kuroki et al., "Biochemical characterization of 25 distinct carcinoembryonic antigen (CEA) epitopes recognized by 57 monoclonal antibodies and catergorized into seven groups in terms of domain structure of the CEA molecule" *Hybridoma* (1992) 11:391-407.
Goldenberg, "Monoclonal antobodies in cancer detection and therapy" *Am. j. Med.* (1993) 94:297-312.
Hinoda et al., "Internal image-bearing anti-idiotypic monoclonal antibodies" *Tumor Biol.* (1995) 16:48-55.
Losman et al., "Mimicry of a carcinoembryonic antigen epitope by a rat monoclonal anti-idiotype antibody" *Int. J. Cancer* (1994) 56:580-584.
Irvine et al., "Induction of delayed-type hypersensitivity responses by monoclonal anti-idiotypic antibodies to tumor cells expressing carcinoembryonic antigen and tumor-associated glycoprotein-72" *Cancer Immunol. Immuther.* (1993) 36;281-292.
Solin et al., "Immunoglobulin constant kappa gene alleles in twelve strains of mice" *Immunogenetics* (1993) 37:401-407.
Honjo et al., "Cloning and complete nucleotide sequence of mouse immunoglobulin $\gamma$1 chain gnen" *Cell* (1979) 18:559-568.
Koprowski et al., "Colorectal carcinoma antigens detected by hybridoma antibodies" *Somatic Cell Genet.* (1979) 5:957-972.
Mitchell, "A carcinoembryonic antigen (CES) specific monoclonal hybridoma antibody that reacts only with high-molecular-weight CEA" *Cancer Immunol. Immunother.* (1980) 10:1-5.
Takahashi et al., "Induction of $CD8^+$cytotoxic T cells by immunization with purified HIV-1 envelope protein in ISCOMS" *Nature* (1990 344:873-875.
Cheresh et al., "Biosynthesis and expression of the disialoganglioside $G_{D2}$, a revelant target antigen on small cell lung carcinoma for monoclonal antibody-mediated cytolysis" *Cancer Res.* (1986) 46:5112-5118.
Ey et al., "Isolation of pure $IgG_1$, $IgG_{2a}$ and $IgG_{2b}$ immunoglobulins from mouse serum using protein A-sepharose" *Immunochem,* (1978) 15:429-436.
Parham, "On the fragmentation of monoclonal IgG1, IgGa, and IgG2b from BALB/c mice" *J. Immunol.* (1983) 131:2895-2902.
Maloney et al., "Monoclonal anti-idiotype antibodies against the murine B cell lymphoma 38C13: Characterization and use as probes for the biology of the tumor *in vivo* and *in vitro* " *Hybridoma* (1985) 4:191-209.
Seon et al., "Monoclonal antibody SN2 defining a human T cell leukemia-associated cell surface glycoprotein" *J. Immunol.* (1984) 132:2089-2095.
Oi et al., "Immunoglobin-producing hybrid cells" *Selected Methods in Cellular Immunology* (1980) Mishell & Shiigi eds., W.H. Freeman and Company, pp. 351-372.
Hunter, "Stadardization of the chloramine-T method of protein iodination" *Proc. Soc. Exp. Biol. Med.* (1970) 133:989-992.
Bhattacharya et al., "Monoclonal antibodies recognizing tumor-associated antigen of human ovarian mucinous cystadenocarcinomas" *Cancer Res.* (1982) 42:1650-1654.
Engvall et al., "Enzyme-linked immunosorbent assay, ELISA" *J. Immunol.* (1972) 109:129-135.
Towbin et al., "Electrophoretic transfer of proteins from polyacrylamide gels to nitrocellulose sheets: Procedure and some applications" *Proc. Natl. Acad. Sci. USA* (1979) 76:4350-4354.
Viale et al., "Idiotypic replica of an anti-human tumor-associated antigen monoclonal antibody" *J. Immunol.* (1989) 143:4338-4344.
Mukerjee et al., "Generation of anti-anti-idiotype antibodies (Ab3) that recognize human breast cancer-associated antigen" *FASEB J.* (1992) 6:A2059. (abstract 6505).
Chattopadhyay et al., "Murine monoclonal anti-idiotype antibody breaks unresponsiveness and induces a specific antibody response to human melanoma-associated proteoglycan antigen in cynomolgus monkeys" *Proc. Natl. Acad. Sci. USA* (1992) 89:2684-2688.
Laemmli, "Cleavage of structural proteins during the assembly of the head of bacteriophage T4" *Nature* (1970) 227:680-685.
Hansen et al., "Solving the problem of antibody interference in commercial 'sandwich'-type immunoassays of carcinoembryonic antigen" *Clin. Chem.* (1989) 35:146-151.
Bhattacharya-Chatterjee et al., "Murine monoclonal anti-idiotype antibody as a potential network antigen for huma carcinoembryonic antigen" *J. Immunol.* (1990) 145:2758-2765.
Hawkins et al., "Plasmid vaccination against B-cell lymphoma" *Cancer Gene Therap.* (1994) 1:208.
Moss, "Vaccinia virus: A tool for research and vaccine development" *Science* (1991) 252:1662-1667.
Bhattacharya-Chatterjee et al., "Idiotypic antibody immunotherapy of cancer" *Cancer Immunol. Immunother.* (1994) 38:75-82.
Bhattacharya-Chatterjee et al., "Idiotype matching: A network antigen idiotype is expressed in sera of colon cancer patients" *Vaccine Res.* (1993) 2:283-290.
Bhattacharya-Chatterjee et al., "Anti-idiotype monoclonal antibodies as vaccines for human cancer" *Intern. Rev. Immunol.* (1991) 7:289-302.
Bhattacharya-Chatterjee et al., "Murine anti-idiotype (Id) monoclonal antibody (mAb) breaks tolerance and induces a specific antibody response to carcinoembryonic antigen (CEA) in colorectal cancer (CRC) patients" *FASEB J.* (1994) 8:A200 (abstrat No. 1156).
Foon et al., "Anti-idiotype antibodies: Novel therapeutic approach to cancer therapy" *Tumor Immunology and Cancer Therapy*, Goldfarb, R.H. et al., eds., (1994) Marcel Dekker, Inc. pp. 281-292.
Foon et al., "Immune response to the carcinoembryonic antigen in patients treated with an anti-idiotype antibody vaccine" *J. Clin. Invest.* (1995) 96:334-342.
Kohler et al., "Idiotype manipulation in disease management" *Adv. Exp. Med. Biol.* (1995) 383:117-122.
Chakraborty et al., "Preclinical evaluation in nonhuman primates of an anti-idiotype antibody that mimicks the carcinoembryonic antigen" *J. Immunother.* (1995) 18:95-103.
Bhattacharya-Chatterjee et al., "Syngeneic monoclonal anti-idiotype antibody related to human carcinoembryonic antigen" *Proceedings of the American Association for Cancer Research, 81st Annual Meeting of Cancer Research*, (1990) 31:279 (abstract No. 1651).
Bhattacharya-Chatterjee et al., "Idiotype matching: Level of expression of a network antigen idiotype in colon cancer patients' sera" *FASEB J.* (1991) 5:A1356 (abstract No. 5713).

Bhattacharya-Chatterjee et al., "Active immunotherapy of colorectal patients with murine monoclonal anti-idiotype antibody" *XVI International Cancer Congress* (Oct. 30, to Nov. 5, 1994) pp. 495-499.

Chakraborty et al., "Murine monoclonal anti-idiotype antibody induces a specific antibody response to human carcinoembryonic antigen (CEA) in cynomolgus monkeys" *FASEB J.* (1994) 8:A504 (abstract No. 2917).

Chatterjee et al., "Anti-idiotypic monoclonal antibodies: Novel approach to immunotherapy" *Handbook of Exp. Pharm.*, Chapter 16 (1994) 113:387-401.

Foon et al., "Murine anti-idiotype (Id) Monoclonal antibody (mAb) induces specific humoral responses to carcinoembryonic antigen (CEA) in colorectal cancer (CRC) patients" *Proc. Ann. Mtg. Am. Soc. Clin. Oncol.* (ASCO) (Abstract Submission Form) (1994) 1 page total.

Mukerjee et al., Generation of monoclonal anti-anti-idiotype antibodies (Ab3) that recognize human carcinoembryonic antigen (CEA). *FASEB J.* (1990) 4:A1951 (abstract No. 1497).

Adetugbo, "Evolution of immunoglobulin subclasses" *J. Biol. Chem.* (1978) 253:6068-6075.

Hieter et al., "Cloned human and mouse kappa immunoglobulin constant and J region genes conserve homology in functional segments" *Cell* (1980) 22:197-207.

Antibody 3H1 Heavy Chain DNA sequence; 3H1 Heavy Chain Protein translation; and GenBank search of nucleotide and protein sequence. Date of search: Nov. 29, 1995, 51 pages total.

Antibody 3H1 Light Chain DNA sequence; 3H1 Light Chain Protein translation; and GenBank search of nucleotide and protein sequence. Date of search: Nov. 29, 1995, 45 pages total.

Horn et al., "Cancer gene therapy using plasmid DNA: Purification of DNA for human clinical trials" *Human Gene Therapy* (1995) 6:565-573.

Flexner et al., "Attenuation of live recombinant vaccinia virus vectors by expression of human Interleukin-2" *New chemical and genetic approaches to vaccination: Prevention of AIDS and other viral, bacterial and parasitic diseases, Vaccines 88* (1988) Ginsberg et al., ed., Cold Spring Harbor Laboratory, New York, pp. 179-184.

Cockett et al., "High level expression of tissue inhibitor of metalloproteinases in Chinese hamster ovary cells using glutamine synthetase gene amplification" *Bio/Technology* (1990) 8:662-667.

Paxton et al., "Sequence analysis of carcinoembryonic antigen: Identification of glycosylation sites and homology with the immunoglobulin supergene family" *Proc. Natl. Acad. Sci. USA* (1987) 84:920-924.

Oikawa et al., "Primary structure of human carcinoembryonic antigen (CEA) deduced from cDNA sequence" *Biochem. Biophys. Res. Commun.* (1987) 142:511-518.

Dohlsten et al., "Monoclonal antibody-superantigen fusion proteins: Tumor-specific agents for T-cell-based tumor therapy" *Proc. Natl. Acad. Sci. USA* (1994)91:8945-8949.

Bird et al., "Single-chain antigen-binding proteins" *Science* (1988) 242:423-426.

Posnett, "A novel method for producing anti-peptide antibodies" *J. Biol. Chem.* (1988) 263:1719-1725.

Tam, "High-density multiple antigen-peptide system for preparation of antipeptide antibodies" *Meth. Enzymol.* (1989) 168:7-15.

Merrifield, "Solid phase peptide synthesis. I. The synthesis of a tetrapeptide" *J. Am. Chem. Soc.* (1963) 85:2149-2154.

Fielder et al., "High level production and long-term storage of engineered antibodies in transgenic tobacco seeds" *Biotechnol.* (1995) 13:1090-1093.

Herlyn et al., "Monoclonal anticolon carcinoma antibodies in complement-dependent cytotoxicity" *Int. J. Cancer* (1981) 27:769-774.

Kantor et al., "Antitumor activity and immune responses induced by a recombinant carcinoembryonic antigen0Vaccinia virus vaccine" *J. Natl. Cancer Inst.* (19920 84:1084-1091.

Tang et al., "Genetic immunization is a simple method for eliciting an immune response" *Nature* (1992) 356:152-154.

Spooner et al., "DNA vaccination for cancer treatment" *Gene Therapy* (1995) 2;173-180.

Wang et al., "Immunization by direct DNA inoculation induces rejection of tumor cell challenge" *Human Gene Therapy* (1995) 6:407-418.

Barry et al., "Protection against mycoplasma infection using expression-library immunization" *Nature* (1995) 377:632-635.

Altschul et al. "Basic local alignment search tool" *J. Mol. Biol.* (1990) 215:403-410.

Hruby et al., "Fine structure analysis and nucleotide sequence of the Vaccinia virus thymidine kinase gene" *Proc. Natl. Acad. Sci. USA* (1983) 80:3411-3415.

Cochran et al., "*In vitro* mutagenesis of the promoter region for a Vaccinia virus gene; Evidence for tandem early and late regulatory signals" *J. Virol.* (1985) 54:30-37.

Mackett et al., "Vaccinia virus: A selectable eukaryotic cloning and expression vector" *Proc. Natl. Acad. Sci. USA* (1982) 79:7415-7419.

Jaffee et al., "High efficiency gene transfer into primary human tumor explants without cell selection" *Cancer Res.* (1993) 53:2221-2226.

Blakenstein et al., "Cancer vaccines in gene therapy" *Gene Therapy* (1996)3:95-96.

McBride et al., "Induction of tolerance to a murine fibrosarcoma in two zones of dosage—the involvement of suppressor cells" *Br. J. Cancer* (1986) 53:707-711.

* cited by examiner

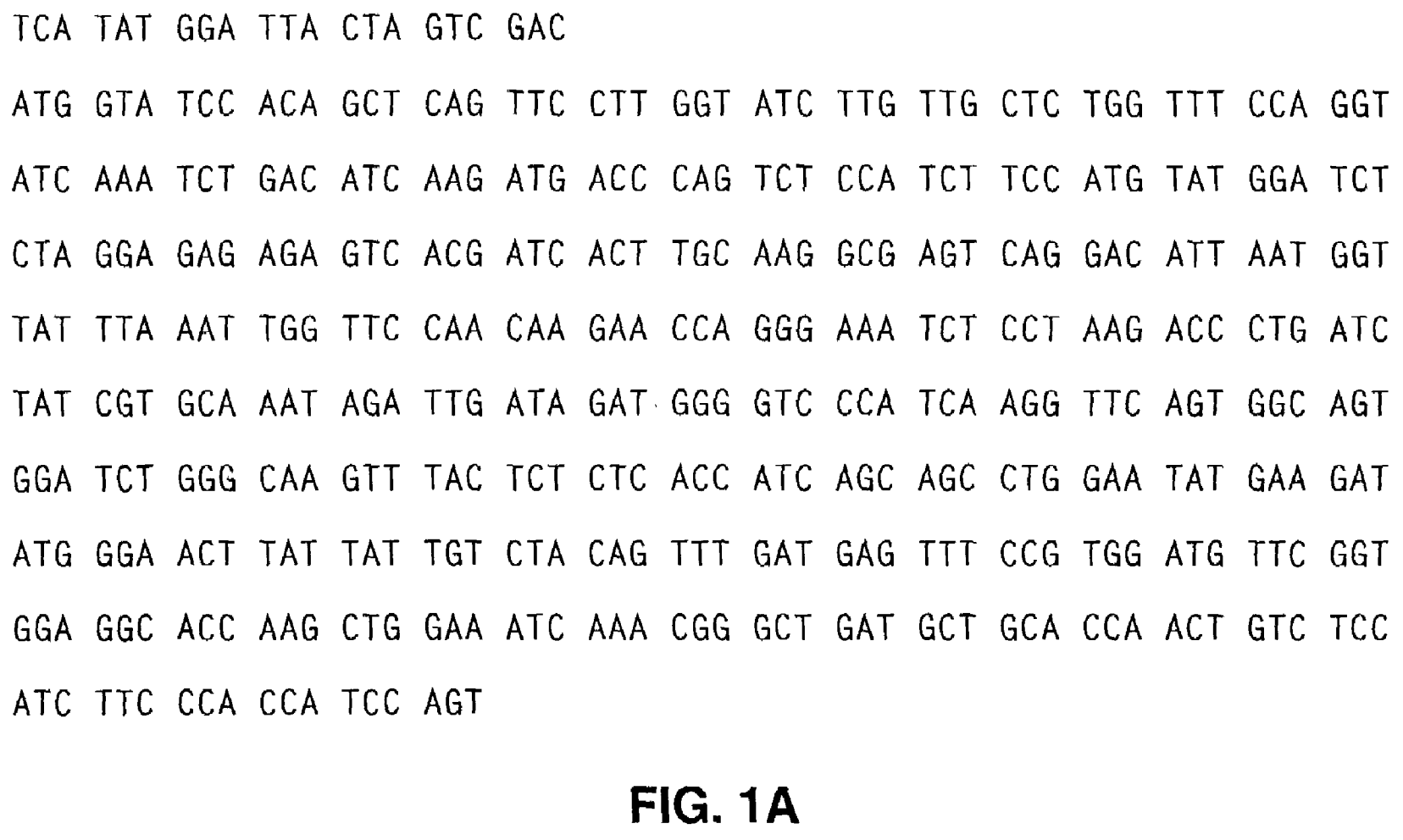

TCA TAT GGA TTA CTA GTC GAC

ATG GTA TCC ACA GCT CAG TTC CTT GGT ATC TTG TTG CTC TGG TTT CCA GGT

ATC AAA TCT GAC ATC AAG ATG ACC CAG TCT CCA TCT TCC ATG TAT GGA TCT

CTA GGA GAG AGA GTC ACG ATC ACT TGC AAG GCG AGT CAG GAC ATT AAT GGT

TAT TTA AAT TGG TTC CAA CAA GAA CCA GGG AAA TCT CCT AAG ACC CTG ATC

TAT CGT GCA AAT AGA TTG ATA GAT GGG GTC CCA TCA AGG TTC AGT GGC AGT

GGA TCT GGG CAA GTT TAC TCT CTC ACC ATC AGC AGC CTG GAA TAT GAA GAT

ATG GGA ACT TAT TAT TGT CTA CAG TTT GAT GAG TTT CCG TGG ATG TTC GGT

GGA GGC ACC AAG CTG GAA ATC AAA CGG GCT GAT GCT GCA CCA ACT GTC TCC

ATC TTC CCA CCA TCC AGT

FIG. 1A

Met Val Ser Thr Ala Gln Phe Leu Gly Ile Leu Leu Leu Trp Phe Pro

Gly Ile Lys Ser Asp Ile Lys Met Thr Gln Ser Pro Ser Ser Met Tyr

Ala Ser Leu Gly Glu Arg Val Thr Ile Thr Cys Lys Ala Ser Gln Asp

Ile Asn Gly Tyr Leu Asn Trp Phe Gln Gln Glu Pro Gly Lys Ser Pro

Lys Thr Leu Ile Tyr Arg Ala Asn Arg Leu Ile Asp Gly Val Pro Ser

Arg Phe Ser Gly Ser Gly Ser Gly Gln Val Tyr Ser Leu Thr Ile Ser

Ser Leu Glu Tyr Glu Asp Met Gly Thr Tyr Tyr Cys Leu Gln Phe Asp

Glu Phe Pro Trp Met Phe Gly Gly Gly Thr Lys Leu Glu Ile Lys Arg

Ala Asp Ala Ala Pro Thr Val Ser Ile Phe Pro Pro Ser Ser

FIG. 1B

AGTCATATGGATTGGGAATTC

ATG GAA TGG AGC TGG GTC ATT CTC TTC CTC CTG TCA GGA ACT GCA GGT

GTC CAC TCT GAG GTC CAG CTG CAA CAG TCT GGA CCT GAG CTG GTG AAG CCT

GGA GCT TCA CTG AAG ATT TCC TGC GAG GCT TCT GGT TAC TCA CTC ACT GCC

TAC ACC ATG AAC TGG GTG AAG CAG AGC CAT GGA AAG AGC CTT GAG TGG GTT

GGG CTG ATT AAT CCT TTC AGT GGT GAT ACT AAC TAC AGC CAG AAA TTC ACG

GGC AAG GCC ACA TTA ACT GTA GAC AGG TCA TCC AGC ACA GCC TAC ATG GAG

CTC CTC AGT CTG ACA TCT GAG GAC TCT GCA GTC TAT TAC TGT GTC ATT ACT

CCG GTT CCC TAC TGG TAC TTC GAT GTC TGG GGC GCA GGG ACC ACG GTC ACC

GTC TCC TCA GCC AAA ACG ACA CCC CCA TCC GTC TAT

FIG. 2A

Met Glu Trp Ser Trp Val Ile Leu Phe Leu Leu Ser Gly Thr Ala Gly

Val His Ser Glu Val Gln Leu Gln Gln Ser Gly Pro Glu Leu Val Lys

Pro Gly Ala Ser Leu Lys Ile Ser Cys Glu Ala Ser Gly Tyr Ser Leu

Thr Ala Tyr Thr Met Asn Trp Val Lys Gln Ser His Gly Lys Ser Leu

Glu Trp Val Gly Leu Ile Asn Pro Phe Ser Gly Asp Thr Asn Tyr Ser

Gln Lys Phe Thr Gly Lys Ala Thr Leu Thr Val Asp Arg Ser Ser Ser

Thr Ala Tyr Met Glu Leu Leu Ser Leu Thr Ser Glu Asp Ser Ala Val

Tyr Tyr Cys Val Ile Thr Pro Val Pro Tyr Trp Tyr Phe Asp Val Trp

Gly Ala Gly Thr Thr Val Thr Val Ser Ser Ala Lys Thr Thr Pro Pro

Ser Val Tyr

FIG. 2B

DIKMTQSPSSMYASLGERVTITC - FRAMEWORK #1

KASQDINGYLN - CDR-1

WFQQEPGKSPKTLIY - FRAMEWORK #2

RANRLID - CDR-2

GVPSRFSGSGSGQVYSLTISSLEYEDMGTYYC - FRAMEWORK #3

LQFDEFPWM - CDR-3

FGGGTKLEIK - FRAMEWORK #4

FIG. 3A

EVQLQQSGPELVKPGASLKISCEASGYSLT- FRAMEWORK #1

AYTMN - CDR-1 [COMPLEMENTARITY DETERMING REGION, CDR]

WVKQSHGKSLEWVG - FRAMEWORK #2

LINPFSGDTNYSQKFTG - CDR-2

KATLTVDRSSSTAYMELLSLTSEDSAVYYCVI - FRAMEWORK #3

TPVPYWYFDV - CDR-3

WGAGTTVTVSS - FRAMEWORK #4

FIG. 3B

```
109 110                 115                 120                 125
GCT GAT GCT GCA CCA ACT GTA TCC ATC TTC CCA CCA TCC AGT GAG CAG TTA ACA TCT GGA  C
--- --- --- --- --- --- --- --- --- --- --- --- --- --- --- --- --- --- --- ---  CE
--- --- --- --- --- --- --- --- --- --- --- --- --- --- --- --- --- --- --- ---  CBA
--- --- --- --- --- --- --- --- --- --- --- --- --- --- --- --- --- --- --- ---  RIII
--- --- --- --- --- --- --- --- --- --- --- --- --- --- --- --- --- --- --- ---  DBA/2
--- --- --- --- --- --- --- --- --- --- --- --- --- --- --- --- --- --- --- ---  C57BL
--- --- --- --- --- --- --- --- --- --- --- --- --- --- --- --- --- --- --- ---  A/J
--- --- --- --- --- --- --- --- --- --- --- --- --- --- --- --- --- --- --- ---  NZB
--- --- --- --- --- --- --- --- --- --- --- --- --- --- --- --- --- --- --- ---  C58
--- --- --- --- --- --- --- --- --- --- --- --- --- --- --- --- --- --- --- ---  AKR
↑↑- --- x-- --- --- --- --- --- --- --- --- --- --- --- --- --- --- --- --- ---  PL
--- --- --- --- --- --- --- --- --- --- --- --- --- --- --- --- --- --- --- ---  SJL
--- --- --- --- --- --- --- --- --- --- --- --- --- --- --- --- --- --- --- ---  M. spretus
--- --- --- --- --- --- --- --T --- --- --- --- --- -CG --A --- --- G-- A-- ---  LOU
--- --- --- --- --- --- --- --- --- --- --- --- --- -TG --A --- --- --- --- ---  DA
                                                                       MKCP-45
    130                 135                 140                 145
GGT GCC TCA GTC GTG TGC TTC TTG AAC AAC TTC TAC CCC AAA GAC ATC AAT GTC AAG TGG  CE
--- --- --- --- --- --- --- --- --- --- --- --- --- --- --- --- --- --- --- ---  CE
--- --- --- --- --- --- --- --- --- --- --- --- --- --- --- --- --- --- --- ---  CBA
--- --- --- --- --- --- --- --- --- --- --- --- --- --- --- --- --- --- --- ---  RIII
--- --- --- --- --- --- --- --- --- --- --- --- --- --- --- --- --- --- --- ---  DBA/2
--- --- --- --- --- --- --- --- --- --- --- --- --- --- --- --- --- --- --- ---  C57BL
--- --- --- --- --- --- --- --- --- --- --- --- --- --- --- --- --- --- --- ---  A/J
--- --- --- --- --- --- --- --- --- --- --- --- --- --- --- --- --- --- --- ---  NZB
--- --- --- --- --- --- --- --- --- --- --- --- --- --- --- --- --- --- --- ---  C58
--- --- --- --- --- --- --- --- --- --- --- --- --- --- --- --- --- --- --- ---  AKR
--- --- --- --- --- --- --- --- --- --- --- --- --- --- -x- --- --- --- --- ---  PL
--- --- --- --- --- --- --- --- --- --- --- --- --- -G- --- --- --- --- --- ---  SJL
--- --- --- --- --- --- --- --- --- --- --- --- --- -G- --- --- --- --- --- ---  M. spretus
--- --- --- --- --- --- C-- A-- --- --- --- --T --- -G- --- --- -G- --- --- ---  LOU
--- --- A-- --- --- --- --- G-- --- --- --- --T --- -G- --- --- -G- --- --- ---  DA
```

FIG. 4B

```
              MKCP-45->
    150                     155                     160                     165
AAG ATT GAT GGC AGT GAA CGA CAA AAT GGC GTC CTG AAC AGT TGG ACT GAT CAG GAC AGC  BALB/c
--- --- --- --- --- --- --- --- --- --- --- --- --- --- --- --- --- --- --- ---  CE
--- --- --- --- --- --- --- --- --- --- --- --- --- --- --- --- --- --- --- ---  CBA MK
--- --- --- --- --- --- --- --- --- --- --- --- --- --- --- --- --- --- --- ---  RIII
--- --- --- --- --- --- --- --- --- --- --- --- --- --- --- --- --- --- --- ---  DBA/2
--- --- --- --- --- --- --- --- --- --- --- --- --- --- --- --- --- --- --- ---  C57BL
--- --- --- --- --- --- --- --- --- --- --- --- --- --- --- --- --- --- --- ---  A/J
--- --- --- --- --- --- --- --- --- --- --- --- --- --- --- --- --- --- --- ---  NZB
--- --- --- --- --- --- --- --- --- --- --↑ ↑-- xxx --- --- --- --- --- --- ---  C58
--- --- --- --- --- --- --- --- --- --- --- --- --- --- --- --- --- --- --- ---  AKR
--- --- --- --- --- --- --- --- --- --- --- --- --- --- --- --- --- --- --- ---  PL
--- --- --- --- --- --- --- --- --- --- --T --- --- --- --- --- --- --- --- ---  SJL
--- --- --- --- --- --- --- --- --- --- --T --- --- --- --- --- --- --- --- ---  M. spretus
--- --- --- --- --- -C- --- --- -G- G-- --T --- G-- --- GTT --- --- --- --- ---  LOU
--- --- --- --- --- --- --- -A- -G- G-- --T --- G-- --- GTT --- --- --- --- ---  DA
    170                     175                     180                     185
AAA GAC AGC ACC TAC AGC ATG AGC AGC ACC CTC ACG TTG ACC AAG GAC GAG TAT GAA CGA  BALB/c
--- --- --- --- --- --- --- --- --- --- --- --- --- --- --- --- --- --- --- ---  CE
--- --- --- --- --- --- --- --- --- --- --- --- --- --- --- --- --- --- --- ---  CBA
--- --- --- --- --- --- --- --- --- --- --- --- --- --- --- --- --- --- --- ---  RIII
--- --- --- --- --- --- --- --- --- --- --- --- --- --- --- --- --- --- --- ---  DBA/2
--- --- --- --- --- --- --- --- --- --- --- --- --- --- --- --- --- --- --- ---  C57BL
--- --- --- --- --- --- --- --- --- --- --- --- --- --- --- --- --- --- --- ---  A/J
--- --- --- --- --- --- --- --- --- --- --- --- --- --- --- --- --- --- --- ---  NZB
--- --- --- --- --- --- --- --- --- --- --- --- --- --- --- --- --- --- --- ---  C58
--- --- --- --- --- --- --- --- --- --- --- --- --- --- --- --- --- --- --- ---  AKR
--- --- --- --- --- --- --- --- --- --- --- --- --- --- --- --- --- --- --- ---  PL
--- --- --- --- --- --- --- --- --- --- --- --A --- --- --- --- --- --- --- ---  SJL
--- --- --- --- --- --- --- --- --- --- --- --A --- --- --- --- --- --- --- ---  M. spretus
--- --- --- --G --- --- --- --- --- --- --- T-- --- --- --- -CT --C --- --- A-T  LOU
--- --- --- --G --- --- --- --- --- --- --- T-- --- --- --- -TT --A --- --- A-G  DA
```

FIG. 4C

```
    190                 195                 200                 205
CAT AAC AGC TAT ACC TGT GAG GCC ACT CAC AAG ACA TCA ACT TCA CCC ATT GTC AAG AGC  BALB/c
--- --- --- --- --- --- --- --- --- --- --- --- --- --- --- --- --- --- --- ---  CE
--- --- --- --- --- --- --- --- --- --- --- --- --- --- --- --- --- --- --- ---  CBA
--- --- --- --- --- --- --- --- --- --- --- --- --- --- --- --- --- --- --- ---  RIII
--- --- --- --- --- --- --- --- --- --- --- --- --- --- --- --- --- --- --- ---  DBA/2
--- --- --- --- --- --- --- --- --- --- --- --- --- --- --- --- --- --- --- ---  C57BL
--- --- --- --- --- --- --- --- --- --- --- --- --- --- --- --- --- --- --- ---  A/J
--- --- --- --- --- --- --- --- --- --- --- --- --- --- --- --- --- --- --- ---  NZB
--- --- --- --- --- --- --- --- --- --- --- --- --- --- --- --- --C --- --- ---  C58
--- --- --- --- --- --- --- --- --- --- --- --- --- --- --- --- --C --- --- ---  AKR
--- --- --- --- --- --- --- --- --- --- --- --- --- --- --- --- --C --- --- ---  PL
--- --- --- --- --- --- --- --- --- --- --- --- --- --- --- --- --C --- --- ---  SJL
--- --- --- --- --- --- --- --- --- --- --- --- --- --- --- --- --- --- --- ---  M. spretus
--- --- CT- --- --- - - --- -TT GT- --T --- --- --- T-C --- --- G-C --- --- ---  LOU
--- --- CT- --- --- --- --- -TT GT- --T --- --- --- T-C --- --- G-C --- --- ---  DA
                                                            <-MKC-4
                                              <-MKC-1B
                                        <-MKC-1
```

FIG. 4D

```
     210             214        +10        +20        +30        +40        +50    +56
TTC  AAC AGG AAT GAG TGT TAGAGACAAA GGTCCTGAGA CGCCACCACC AGCTCCCCAG CTCCATCCTA TCTTCC BALB/c
---  --- --- --- --- --- ---------- --                                                CE
---  --- --- --- --- --- ----------                                                   CBA
---  --- --- --- --- --- ----------                                                   RIII
---  --- --- --- --- --- ----------                                                   DBA/2
---  --- --- --- --- --- ---------- --                                                C57BL
---  --- --- --- --- --- ----------                                                   A/J
---  --- --- --- --- --- ---------- ---                                               NZB
---  --- --- --- -↑- -X- ----------                                                   C58
---  --- --- --- --- --- ----------                                                   AKR
---  --- --- --- --- --- ----------                                                   PL
---  --- --- --- --- --- -----C----                                                   SJL
---  --- --- --- --- --- -----C---- ---------- ---------- ---------- ---------- ------ M.spretus
---  --- --- --- --- - - ----CC---- ---------G T-----T.. .--------- ----T---A- ------ LOU
---  --- --- --- --- --- ----CC---- ---------G T-----T.. .--------- T---T---A- ------ DA
```

FIG. 4E

```
                20        40        60        80
                 .         .         .         .
                                                                                               A
0   TCGGGGACATGGGAAGGGTGCAAAAGTAGCGGCCTTCTAGAAGGTTTGGACCTGTCCTGTCCTGTCCGACAGTGTAATCACATATACTTTTTCTTGTAGC

                      T                         N     A  S  Q
      K  T  T  P  P  S  V  Y  P  L  A  P  G  S  A  A  Q  T  V  S  M  V  T  L  G  C  L  V  K  G  Y  F  P
100 CAAAACGACACCCCCATCTGTCTATCCACTGGCCCCTGGATCTGCTGCCCAAACTAACTCCATGGTGACCCTGGGATGCCTGGTCAAGGGCTATTTCCCT

     E  P  V  T  V  T  W  N  S  G  S  L  S  S  G  V  H  T  F  P  A  V  L  Q  S  D  L  Y  T  L  S  S  S
200 GAGCCAGTGACAGTGACCTGGAACTCTGGATCCCTGTCCAGCGGTGTGCACACCTTCCCAGCTGTCCTGCAGTCTGACCTCTACACTCTGAGCAGCTCAG

       S        T                                      A  P
    V  T  V  P  S  S  P  R  P  S  E  T  V  T  C  N  V  A  H  P  A  S  S  T  K  V  D  K  K  I
300 TGACTGTCCCCTCCAGCCCTCGGCCCAGCGAGACCGTCACCTGCAACGTTGCCCACCCGGCCAGCAGCACCAAGGTGGACAAGAAAATTGGTGAGAGGAC

400 ATATAGGGAGGAGGGGTTCACTAGAAGTGAGGCTCAAGCCATTAGCCTGCCTAAACCAACCAGGCTGGACAGCCAACCAACCAGGAAATGGATCTCAGCC

500 CAGAAGATCAAAAGTTGTTCTTCTCCCTTCTGGAGATTTCTATGTCCTTTACAACTCAATTGGTTAATATCCTGGGTTGGAGTCCCACACATCTTGACAA

600 ACAGAGACAAATTTGAGTATCACCAGCCAAAAGTCATACCCAAAAACAGCCTGGCATGACCACACACCAGACTCAAACTTACCCTACCTTTATCCTGGTG

                                                           V  P  R  D  C  G  C  K  P  C  I  C  T
700 GCTTCTCATCTCCAGACCCCAGTAACACATAGCTTTCTCTCCACAGTGCCCAGGGATTGTGGTTGTAAGCCTTGCATATGTACAGGTAAGTCAGTGGCCT

                                                                                            V  P  E  V  S  S
800 TCACCTGACCCAGATGCAACAAGTGGCAATGTTGGAGGGTGGCCAGGTATTGACCTATTTCCACCTTTCTTCTTCATCCTTAGTCCCAGAAGTATCATCT
```

FIG. 5A

```
                                    T    L     V
      V  F  I  F  P  P  K  P  K  D  V  L  T  I  T  L  T  P  K  V  T  C  V  V  V  D  I  S  K  D  D  P  E
900   GTCTTCATCTTCCCCCCAAAGCCCAAGGATGTGCTCACCATTACTCTGACTCCTAAGGTCACGTGTGTTGTGGTAGACATCAGCAAGGATGATCCCGAGG

                               N                                                                V     A
      V  Q  F  S  W  F  V  D  D  V  E  V  H  T  A  Q  T  Q  P  R  E  E  Q  F  N  S  T  F  R  S  V  S  E  L
1000  TCCAGTTCAGCTGGTTTGTAGATGATGTGGAGGTGCACACAGCTCAGACGCAACCCCGGGAGGAGCAGTTCAACAGCACTTTCCGCTCAGTCAGTGAACT

       P  I  M  H  Q  D  W  L  N  G  K  E  F  K  C  R  V  N  S  A  A  F  P  A  P  I  E  K  T  I  S  K  T
1100  TCCCATCATGCACCAGGACTGGCTCAATGGCAAGGAGTTCAAATGCAGGGTCAACAGTGCAGCTTTCCCTGCCCCCATCGAGAAAACCATCTCCAAAACC

      K
1200  AAAGGTGAGAGCTGCAGTGTGTGACATAGAAGCTGCAATAGTCAGTCCATAGACAGAGCTTGGCATAACAGACCCCTGCCCTGTTCGTGACCTCTGTGCT

                                 K     R
                              G  R  P  K  A  P  Q  V  Y  T  I  P  P  P  K  E  Q  M  A  K  D  K  V  S  L
1300  GACCAATCTCTTTACCCACCCACAGGCAGACCGAAGGCTCCACAGGTGTACACCATTCCACCTCCCAAGGAGCAGATGGCCAAGGATAAAGTCAGTCTGA

                                                           S  D        A  P                             D
      T  C  M  I  T  D  F  F  P  E  D  I  T  V  E  W  Q  W  N  G  Q  P  A  E  N  Y  K  N  T  Q  P  I  M  N
1400  CCTGCATGATAACAGACTTCTTCCCTGAAGACATTACTGTGGAGTGGCAGTGGAATGGGCAGCCAGCGGAGAACTACAAGAACACTCAGCCCATCATGAA
```

FIG. 5B

```
                D
       T  N  G  S  Y  F  V  Y  S  K  L  N  V  Q  K  S  N  W  E  A  G  N  T  F  T  C  S  V  L  H  E  G  L
1500 CACGAATGGCTCTTACTTCGTCTACAGCAAGCTCAATGTGCAGAAGAGCAACTGGGAGGCAGGAAATACTTTCACCTGCTCTGTGTTACATGAGGGCCTG

      H  N  H  H  T  E  K  S  L  S  H  S  P  G  K term
1600 CACAACCACCATACTGAGAAGAGCCTCTCCCACTCTCCTGGTAAATGATCCCAGTGTCCTTGGAGCCCTCTGGTCCTACAGGACTCTGACACCTACCTCC

                                              .poly A
1700 ACCCCTCCCTGTATAAATAAAGCACCCAGCACTGCCTTGGGACCCTGCAATAACGTCCTGGTGATTTCTGAGATGTAGAGTCTAGCTAGGTCATGGAATG
```

FIG. 5C

| PEPTIDES | SEQUENCE | AMINO ACID NO. IN 3H | ALIGNMENT WITH CEA |
|---|---|---|---|
| HCD-1 | LTAYTMNWV | $V_L$ 29-37 | LTAYTMNWV<br>:\|\|: :<br>*ATPGPAYSGREII*<br>60 |
| LCO-1 | KASQDINGYLN | $V_L$ 24-34 | KASQDINGYLN<br>\| \|\|\| :<br>**PQYSWRINGIPQQHT*<br>590 |
| LCD-2 | TLTYRANRLIDGV | $V_L$ 46-58 | TLIYRANRLIDGV<br>\|\|\|\|<br>**SNPPAQYSWLIDGNIQQ*<br>410 |
| HFW-1 | PELVKP | $V_L$ 9-14 | PELVKP<br>\|\|\| \|\|<br>**FRVYPELPKPSISSNNSKPV*<br>110 |
| LFW-1 | GERV | $V_L$ 16-19 | YASIGERVTITCKAS<br>\|\|\|\|<br>*SWYKGERVDGNRQII*<br>35 |

Alignment with 3H1 sequences in reverse orientation

| | | | |
|---|---|---|---|
| HCO-2R | GTFKQSYNTDGSFPNIL | $V_L$ 66-50 | GTFKQSYNTDGSFPNIL<br>\|\|\| \|\| :<br>**FVNGTFQQSTQELFIPNIT*<br>245 |
| LCD-1R | NLYGNIDQSAK | $V_L$ 34-24 | NLYGNIDQSAK<br>\|\|\|<br>**LDVLYGPDTPIIS*<br>560 |
| HCD-1R | NMYA | $V_L$ 35-31 | NMTYA<br>\| \|\|\|<br>**PNNNGTYACFVSNL*<br>615 |

FIG. 19A

```
                    L I D G   P        3H1 VL CDR 2
                    | | | |   |
                    F V N   T F     S  CEA repeat I
S N P P A Q Y S W L I D G N I Q Q H  CEA repeat II
      S P         R       I P          CEA repeat III
:   : |   :   :         | | |   | |
T S S S R D V T L T A K G T F K Q S  3H1 VL near CDR 2 (reverse)
              |     | | |
V T I T C K A S Q D I N G Y L N W    3H1 VL near CDR 1
```

FIG. 19B

MURINE MONOCLONAL ANTI-IDIOTYPE ANTIBODY 3H1 SEQUENCES FOR HUMAN CARCINOEMBRYONIC ANTIGEN

CROSS-REFERENCE TO RELATED APPLICATIONS

This application is a continuation-in-part of U.S. Ser. No. 08/365,484 filed Dec. 28, 1994, now abandoned, which is incorporated by reference herein in its entirety.

TECHNICAL FIELD

This invention relates to monoclonal anti-idiotype antibodies. More specifically, it relates to polynucleotide and polypeptide sequences for an anti-idiotype antibody 3H1, which escapes immune tolerance and elicits an immune response to an epitope of carcinoembryonic antigen (CEA).

BACKGROUND OF THE INVENTION

In spite of extensive medical research and numerous advances, cancer remains the second leading cause of death in the United States. Colorectal cancer is the third most common cancer and the second leading cause of cancer deaths. While the traditional modes of therapy, such as surgery, radiotherapy and chemotherapy, are widely used and are in many instances successful, the still existing high death rate from cancers such as colorectal compels the need for alternative modes of therapy.

The immunotherapy of human cancer using tumor cells or tumor-derived vaccines has been disappointing for several reasons. It has been consistently difficult to obtain large quantities or purified tumor-associated antigens which are often chemically ill-defined and difficult to purify. In addition, there remains the problem of immunobiological response potential against tumor antigens, or in other words, the question of whether a cancer patient can effectively mount an immune response against his or her tumor. Tumor-associated antigens (TAA) are often a part of "self" and usually evoke a very poor immune response in a tumor-bearing host due to tolerance to the antigens, such as T cell-mediated suppression. Immunobiologists have learned that a poor antigen (in terms of eliciting an immune response) can be turned into a strong antigen by changing the molecular environment. Changes of hapten carrier allow T cell helper cells to become active, making the overall immune response stronger. Thus, changing the carrier can also turn a tolerogenic antigen into an effective antigen. McBridge et al. (1986) *Br. J. Cancer* 53:707. Often the immunological status of a cancer patient is suppressed such that the patient is only able to respond to certain T-dependent antigens and not to other antigen forms. From these considerations, it would make sense to introduce molecular changes into the tumor associated antigens before using them as vaccines. Unfortunately, this is impossible to accomplish for most tumor antigens, because they are not well defined and are very hard to purify.

The network hypothesis of Lindemann ((1973) *Ann. Immunol.* 124:171–184) and Jerne ((1974) *Ann. Immunol.* 125:373–389) offers an elegant approach to transform epitope structures into idiotypic determinants expressed on the surface of antibodies. According to the network concept, immunization with a given tumor-associated antigen will generate production of antibodies against this tumor-associated antigen, termed Ab1; this Ab1 is then used to generate a series of anti-idiotype antibodies against the Ab1, termed Ab2. Some of these Ab2 molecules can effectively mimic the three-dimensional structure of the tumor-associated antigen identified by the Ab1. These particular anti-idiotypes called Ab2β fit into the paratopes of Ab1, and express the internal image of the tumor-associated antigen. The Ab2β can induce specific immune responses similar to those induced by the original tumor-associated antigen and can, therefore, be used as surrogate tumor-associated antigens. Immunization with Ab2β can lead to the generation of anti-anti-idiotype antibodies (Ab3) that recognize the corresponding original tumor-associated antigen identified by Ab1. Because of this Ab1-like reactivity, the Ab3 is also called Ab1' to indicate that it might differ in its other idiotopes from Ab1.

A potentially promising approach to cancer treatment is immunotherapy employing anti-idiotype antibodies. In this form of therapy, an antibody mimicking an epitope of a tumor-associated protein is administered in an effort to stimulate the patient's immune system against the tumor, via the tumor-associated protein. WO 91/11465 describes methods of stimulating an immune response in a human against malignant cells or an infectious agent using primate anti-idiotype antibodies. However, not all anti-idiotype antibodies can be used in therapeutic regimens against tumors. Moreover, since different cancers have widely varying molecular and clinical characteristics, it has been suggested that anti-idiotype therapy should be evaluated on a case by case basis, in terms of tumor origin and antigens express.

Anti-Id monoclonal antibodies structurally resembling tumor-associated antigens have been used as antigen substitutes in cancer patients. Herlyn et al. (1987) *PNAS* 84:8055–8059; Mittleman et al. (1992) *PNAS* 89:466–470; Chatterjee et al. (1993) *Ann. N.Y. Acad.* 690:376–278. It has been proposed that the anti-Id provides a partial analog of the tumor-associated antigen in an immunogenic context.

Carcinoembryonic antigen (CEA) is a 180,000-kiloDalton glycoprotein tumor-associated antigen present on endodermally-derived neoplasms of the gastrointestinal tract, such as colorectal and pancreatic cancer, as well as other adenocarcinomas such as breast and lung cancers. CEA is also found in the digestive organs of the human fetus. Circulating CEA can be detected in the great majority of patients with CEA-positive tumors. Specific monoclonal antibodies have been raised against CEA and some have been radiolabeled for diagnostic and clinical studies. Hansen et al. (1993) *Cancer* 71:3478–3485; Karoki et al. (1992) *Hybridoma* 11:391–407; Goldenberg (1993) *Am. J. Med.* 94:297–312. As with most tumor-associated antigens which are seen as self-antigens by the immune system, cancer patients are immunologically "tolerant" to CEA, possibly due to its oncofetal origin. Studies to date on patients with CEA-positive tumors have not demonstrated the ability to generate immunity to CEA. Thus, immunotherapy based on CEA has heretofore not been possible.

CEA nonetheless is an excellent tumor-associated antigen for active immunotherapy with anti-idiotype antibody. CEA is typically present at high levels on the tumor cell surface. CEA is also one of the most well-characterized antigens, as its gene sequence is known and its three dimensional structures have been identified. CEA is a member of the immunoglobulin supergene family located on chromosome 19 which is thought to be involved in cell-cell interactions.

Inasmuch as some of the epitopes on CEA are shared by normal tissues, immunization with intact CEA molecule might trigger potentially harmful autoimmune reactions. An immune reaction against a tumor associated epitope, on the other hand, would be desirable. A number of investigators have generated anti-idiotype antibodies in rats, mice, baboons and humans that mimic CEA. See, e.g., Hinoda et al. (1995) *Tumor Biol.* 16:48–55; Losman et al. (1994) *Int. J. Cancer* 56:580–584*; Irvine* et al. (1993) *Cancer Immunol. Immunother.* 3:281–292. However, given the size of CEA (and likely numerous epitopes), and the fact that CEA is expressed on some normal tissues, it was not known whether anti-idiotype antibodies would be effective in eliciting an anti-CEA response that effects anti-tumor immunity.

Carcinomas of the gastrointestinal tract are often not curable by standard therapies. Thus, new therapeutic approaches for this disease are needed. The present invention overcomes the deficiencies in the prior art by providing polynucleotide and polypeptide sequences for a monoclonal anti-idiotype antibody (3H1) which escapes immune tolerance and induces an anti-CEA immune response in gastrointestinal cancer patients with advanced disease.

All references cited herein, both supra and infra, are hereby incorporated by reference in their entirety.

DISCLOSURE OF THE INVENTION

This invention encompasses polypeptides comprising at least a portion of a variable region of an anti-idiotype antibody 3H1 and polynucleotides encoding these polypeptides. The invention also includes pharmaceutical compositions and vaccines comprising 3H1 polypeptides and 3H1 polynucleotides. Also included in the present invention are diagnostic kits and methods of using 3H1 polypeptides and 3H1 polynucleotides, including methods of treating CEA-associated tumors.

Further, an object of the invention is to provide a composition and method of use of anti-idiotype (anti-Id) monoclonal 3H1 polynucleotides and polypeptides to induce anti-tumor immunity in patients with CEA-associated disease, such as gastrointestinal cancer.

Accordingly, in one aspect, the invention encompasses polynucleotides encoding a polypeptide having immunological activity of monoclonal anti-idiotype antibody 3H1, wherein the polynucleotide is comprised of a sequence encoding a sequence of at least 5 amino acids of a variable light chain of 3H1. In another aspect, the invention encompasses an isolated polynucleotide encoding a polypeptide having immunological activity of monoclonal anti-idiotype antibody 3H1, wherein the polynucleotide is comprised of a sequence encoding a sequence of at least 5 amino acids of a variable heavy chain of 3H1.

In another aspect, the invention provides polynucleotides that hybridize to a polynucleotide comprised of a nucleotide sequences encoding a portion of light chain variable region of 3H1, wherein the polynucleotide is comprised of at least 10 contiguous nucleotides of SEQ. ID. NO:1. The invention also provides polynucleotides that hybridize to a polynucleotide comprised of a nucleotide sequence encoding a portion of heavy chain variable region of 3H 1, wherein the polynucleotide is comprised of at least 10 contiguous nucleotides of SEQ. ID. NO:3.

Another aspect of the invention is cloning and expression vectors comprising the polynucleotides of the invention. Also included are host cells comprising the polynucleotides of the invention.

In another aspect, plasmids are provided that comprise a polynucleotide encoding 3H1 light chain region and heavy chain region. These plasmids are designated ATCC 97394 and 97395 respectively.

Another aspect of the invention are polypeptides having immunological activity of monoclonal anti-idiotype antibody 3H1, wherein the polypeptides comprise a sequence of at least about 5 amino acids of a variable light chain amino acid sequence of 3H 1, and wherein the polypeptide does not consist of an amino acid sequence identical to that of intact 3H1. In another aspect, polypeptides are provided that comprise a sequence of at least 5 amino acids of a variable heavy chain amino acid sequence of 3H1, and wherein the polypeptides do not consist of an amino acid sequence identical to that of intact 3H1.

In another aspect, 3H1 polypeptides are provided that contain a region of homology to CEA.

In another aspect, the invention provides fusion polypeptides comprising at least 10 contiguous amino acids of SEQ ID NO:2 and at least 10 contiguous amino acids of SEQ ID NO:4. Also included in the invention are polymeric 3H1 polypeptides.

In another aspect, the invention includes pharmaceutical compositions and vaccines comprising an effective amount of 3H1 polypeptide(s) or 3H1 polynucleotide(s).

In another aspect, the invention also provides diagnostic kits comprising 3H1 polypeptide(s) or 3H1 polynucleotide(s) in suitable packaging.

In another aspect, the invention provides methods of inducing an anti-CEA immune response comprising administering 3H1 polynucleotide(s) or polypeptide(s) to an individual.

In another aspect, the invention provides methods of stimulating a T cell responce in an individual having CEA-associated disease, comprising the step of administering 3H1 polypeptide(s).

In another aspect, methods are provided for detecting an antibody that binds to 3H1 in a biological sample. These methods entail the steps of contacting antibody from the sample obtained from an individual with a 3H1 polypeptide under conditions that permit formation of a stable antigen-antibody complex and detecting stable complex formed, if any.

In another aspect, the invention encompasses 3H1 heavy and light chain fragments and polynucleotides encoding the heavy and light chain fragments selected from the group consisting of 3H1 heavy chain nucleotides, 3H1 heavy chain amino acids, 3H1 light chain nucleotides, 3H1 light chain amino acids and similar functionally equivalent sequences thereof having 1 to 5 additional nucleotides or amino acids.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized, the invention is capable of modifications within the skill of the relevant art without departing from the spirit and scope of the invention.

BRIEF DESCRIPTION OF THE DRAWINGS

FIGS. 1A–B depicts the cDNA sequence (SEQ ID NO:1; FIG, 1A) and the amino acid sequence (SEQ ID NO:2; FIG. 1B) of the light chain variable region of 3H1 and adjoining residues.

FIGS. 2A–B depicts the cDNA sequence (SEQ ID NO:3; FIG. 2A) and the amino acid sequence (SEQ ID NO:4; FIG. 2B) of the heavy chain variable region of 3H1 and adjoining residues.

FIG. 3 depicts the amino acid sequences of the light chain variable region (SEQ ID NO:5; FIG. 3A) and the heavy chain variable region (SEQ ID NO:6; FIG. 3B) of 3H1. FIG.

3A depicts the light chain variable region, which consists of 4 framework regions, depicted in SEQ ID NOs: 51, 52, 53, and 55 (Framework regions 1, 2, 3, and 4, respectively), and 3 CDRs, depicted in SEQ ID NOs: 14, 50, and 54 (CDRs 1, 2, and 3, respectively). FIG. 3B depicts the heavy chain variable region, which consists of 4 framework regions, depicted in SEQ ID NOs: 56, 58, 60, and 62 (Framework regions 1, 2, 3, and 4, respectively), and 3 CDRs, depicted in SEQ ID NOs: 57, 59, and 61 (CDRs 1,2, and 3, respectively).

FIG. 5 depicts two allotypes of the mouse immunoglobulin heavy chain. The germ-line DNA sequence from newborn mice is shown (SEQ. ID NO:8), along with the encoded protein (SEQ. ID NO:9). Shown in the line above is another protein sequence obtained from the mouse myeloma MOPC 21 (SEQ. ID NO:10). Other naturally occurring allotypes are possible. The figure is excerpted from Honjo et al. (1979) *Cell* 18:559–568, which is hereby incorporated herein by reference.

FIG. 19 (SEQ ID NO:12 through SEQ ID NO:34) depicts selected amino acid sequence comparisons between the light and heavy chain variable regions of 3H1 and CEA. Matching amino acids are denoted by a solid line.

MODES FOR CARRYING OUT THE INVENTION

Figure 4A:
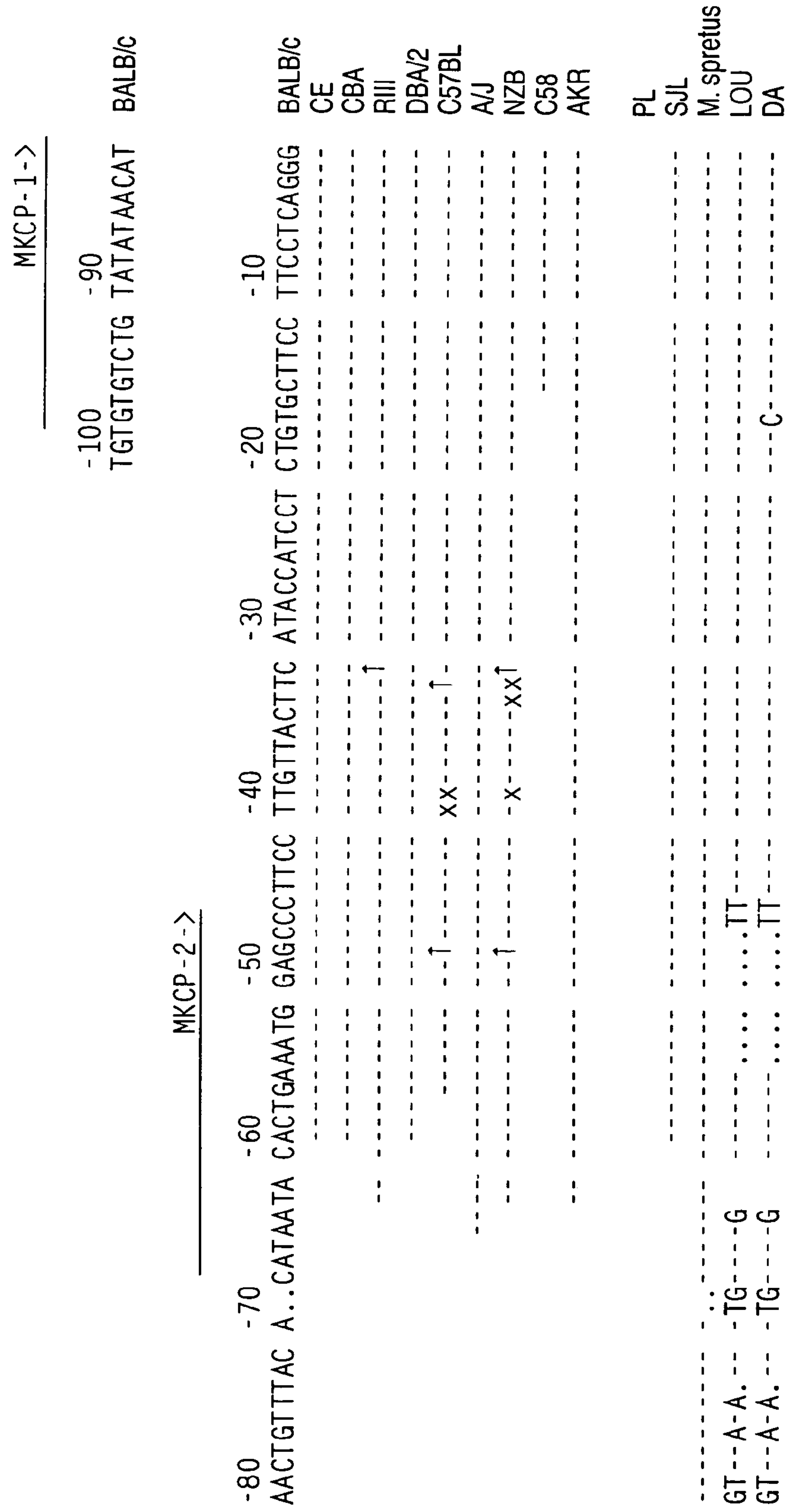
FIG. 4 depicts mouse and rat immunoglobulin kappa chain gene sequences, comparing the sequences within the kappa chain constant region for different strains and highlighting allotypic differences. Included are kappa chain constant region sequences for SEQ ID NO: 7, 63–67, respectively. The four genetic allotypes encode two protein allotypes. Other naturally occurring allotypes are possible. The figure is excerpted from Solin et al. (1993) Immunogenetics 37:401–407, which is hereby incorporated herein by reference.

We have discovered a polynucleotide sequence encoding the variable regions of an anti-idiotype antibody 3H1 and the polypeptide fragments of 3H1 encoded thereby. Thus, the present invention encompasses polynucleotide sequences encoding the anti-idiotype antibody 3H1 and functionally equivalent fragments thereof, polypeptide fragments of 3H1, recombinant methods for producing these 3H1 polynucleotides and polypeptides, pharmaceutical and vaccine compositions comprising 3H1 polynucleotides and polypeptides, diagnostic kits comprising 3H1 polynucleotides and polypeptides and methods using 3H1 polypeptides and/or 3H1 polynucleotides.

These polypeptides and polynucleotides are useful for assessment and treatment of CEA-associated disease, such as colorectal cancer. These and other uses of 3H1 polynucleotides and 3H1 polypeptides of this invention will be discussed in more detail below.

Cancer patients are often immunosuppressed and tolerant to some tumor associated antigens (TAA). Triggering an active immune response to such TAA represents an important challenge in cancer therapy. The present inventors use a network theory approach to vaccine therapy using internal image antigens. Immunization with a given antigen generates the production of antibodies against the antigen. As used herein, "Ab1" represents anti-tumor monoclonal antibody; "Ab2" represents anti-idiotypic monoclonal antibody; and "Ab3" represents anti-anti-idiotypic monoclonal antibody.

We have cloned and isolated a cDNA sequence encoding the variable regions of 3H1. 3H1 is a murine monoclonal anti-idiotype (Id) antibody (Ab2) which appears to mimic a distinct and specific epitope of the 180,000 mw carcinoembryonic antigen (CEA). 3H1 effectively escapes immune tolerance to CEA and elicits an immune response in patients with advanced CEA associated disease (such as colorectal cancer). 3H1 has also been shown to elicit an immune response in all species tested, including mice, rabbits, and monkeys. While not wishing to be bound by any one theory, one explanation is that the 3H1 combining site may present a region that at least partly resembles an epitope in CEA in the context of one or more other epitopes which render it more immunogenic. The epitope of CEA which resembles that of 3H1 is identified by the anti-CEA mAb 8019 (Ab1), which recognizes a distinct and specific epitope on CEA, and was used to immunize syngeneic BALB/c mice for the production of anti-Id mAb 3H1. A complete description of 3H1, including its generation and characterization, is found in commonly-owned patent application Ser. No. 08/579,940 (Example 1).

The useful materials and processes of the present invention are made possible by the provision of the polynucleotide sequences encoding 3H1. These sequences allow for design of polypeptides which can be useful, for example, as vaccines for treatment of CEA-associated disease or as reagents for detecting the presence of Ab1 and/or Ab3. In addition, these sequences allow the design of polynucleotides which are useful as probes and primers for the detection and amplification of target regions of 3H1, as well as 3H1 polynucleotides that are useful as vaccines.

Definitions

"3H1" is an anti-idiotype antibody (Ab2) which contains an epitope that at least partially resembles a distinct and specific epitope of the 180,000 m.w. carcinoembryonic antigen (CEA) primarily expressed in high density by human pancreatic and colonic tumor cells. The generation and characterization of 3H1 is described infra in Example 1. Different biological functions are associated with 3H1, including, but not limited to, binding to Ab1 and/or Ab3 and an ability to induce an immune response (humoral and/or cellular) against CEA. Unless otherwise specified, the term "intact 3H1" refers to the amino acid sequence of the entire molecule of 3H1. A "fragment" of 3H1 is a portion of 3H1.

As used herein, "immunological activity" of 3H1 refers to any of the following activities: (a) ability to bind Ab1 (8019); (b) ability to elicit a specific immune response, particularly an antibody (humoral) response, and/or a T cell response, and the effector functions that result therefrom. T cell response includes T helper cell function, cytotoxic T cell function, inflammation inducer T cells, and T cell suppression. Immunological activity is measurable by using standard methods known in the art, such as radioimmunoassay (RIA), enzyme-linked immunoabsorbant assay (ELISA), complement fixation, opsonization, detection of T cell proliferation, and various $^{51}$Cr release assays. These methods are described, inter alia, herein.

3H1 "activity", "function(s)", or "characteristic(s)" are used interchangeably and refer to various features of 3H1. Examples of 3H1 function(s) include, but are not limited to, binding to Ab1 and/or Ab3, inducing Ab3 and/or inducing a cellular immune response, preferably an anti-CEA response, and amelioration or palliation of CEA-associated disease.

As used herein, a "polynucleotide" is a polymeric form of nucleotides of any length, which contain deoxyribonucleotides, ribonucleotides, and/or their analogs. The terms "polynucleotide" and "nucleotide" as used herein are used interchangeably. Polynucleotides may have any three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double-stranded form and each of two complementary single-stranded forms known or predicted to make up the double stranded form.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. Analogs of purines and pyrimidines are known in the art, and include, but are not limited to, aziridinylcytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudoruacil, 5-pentynyluracil and 2,6-diaminopurine. The use of uracil as a substitute for thymine in a deoxyribonucleic acid is also considered an analogous form of pyrimidine.

If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications included in this definition are, for example, "caps", substitution of one or more of the naturally occurring nucleotides with an analog, internucleotide modifications such as, for example, those with uncharged linkages (e.g., methyl phosphonates, phosphotriesters, phosphoamidates, Carbarmates etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s).

Further, any of the hydroxyl groups ordinarily present in the sugars may be replaced by phosphonate groups, phosphate groups, protected by standard protecting groups, or activated to prepare additional linkages to additional nucleotides, or may be conjugated to solid supports. The 5' and 3' terminal OH groups can be phosphorylated or substituted with amines or organic capping group moieties of from 1 to 20 carbon atoms. Other hydroxyls may also be derivatized to standard protecting groups.

Polynucleotides can also contain analogous forms of ribose or deoxyribose sugars that are generally known in the art, including, but not limited to, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside.

As noted above, one or more phosphodiester linkages may be replaced by alternative linking groups. These alternative linking groups include, but are not limited to, embodiments wherein phosphate is replaced by P(O)S ("thioate"), P(S)S ("dithioate"), (O)$NR_2$ ("amidate"), P(O)R, P(O)OR', CO or $CH_2$ ("formacetal"), in which each R or R' is independently H or substituted or unsubstituted alkyl (1–20 C) optionally containing and ether (—O—) linkage, aryl, alkenyl, cycloalky, cycloalkenyl or araldyl. Not all linkages in a polynucleotide need be identical.

Although conventional sugars and bases will be used in applying the method of the invention, substitution of analogous forms of sugars, purines and pyrimidines can be advantageous in designing a final product, as can alternative backbone structures like a polyamide backbone.

A "fragment" (also called a "region") of a 3H1 polynucleotide (i.e., a polynucleotide encoding 3H1) is a portion of a 3H1 polynucleotide sequence and has at least 10 polynucleotides. Preferred fragments are comprised of a region encoding at least 5 contiguous amino acids of a variable region of 3H1, more preferably, at least 10 contiguous amino acids of a variable region, and even more preferably at least 15 contiguous amino acids of a variable region.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

A polypeptide "fragment" (also called a "region") of 3H1 is a portion of the amino acid sequence of 3H1 and has at least 5 amino acids. Preferably a fragment of 3H1 is comprised of at least 4 contiguous amino acids of a variable region of 3H1, more preferably at least 5 amino acids, and even more preferably about 10 amino acids. For purposes of this invention, a fragment of 3H1 can be identified and characterized by any of the following functions: (a) homology to CEA; (b) ability to bind Ab1 or Ab3; (c) ability to elicit an immune response, preferably an immune response that is anti-CEA; (d) ability to effect amelioration, delay, prevention, or slowing of CEA-associated tumors and/or amelioration or palliation of the associated disease state. Items (b), (c), or (d) fall within the term "immunologically reactive". A 3H1 fragment can have any, more than one, or all of the above identified functions. Methods for determining these functions (a) through (d) will be described below.

A 3H1 polypeptide which is "homologous" to CEA or "shares homology" with CEA means that, when the amino acid sequences of CEA and a 3H1 polypeptide are aligned in any manner, including in the same or reverse orientation with respect to each other, at least 2, preferably 3, more preferably 4, contiguous amino acids within the polypeptide match with CEA. Because functional peptide fragments can be very small for purposes of this invention, only a few amino acids may match (for example, the requisite number of contiguous amino acids required for a binding site and/or antigen presentation can be as few as 2 to 5 amino acids). A 3H1 polypeptide that "contains a region of homology" to CEA shares homology to CEA within its amino acid sequence, as defined above.

A "fusion polypeptide" is a polypeptide comprising regions in a different position in the sequence than occurs in nature. The regions may normally exist in separate proteins and are brought together in the fusion polypeptide; or they may normally exist in the same protein but are placed in a new arrangement in the fusion polypeptide.

As used herein, an "immune response" refers to a humoral response, a cellular response or both.

A "functionally equivalent fragment" of a 3H1 polypeptide or polynucleotide preserves at least one property and/or function of the 3H1 polypeptide or polynucleotide. For example, the sequences may be varied by adding additional nucleotides or peptides as known in the art, such that the functionality of the sequence to induce immunity is not altered. Other examples are deletion and/or substitution of sequences. Alternatively, the sequences can be varied by substituting nucleotides or amino acids, or a combination of addition, deletion, or substitution. As is evident to one of skilled in the art, functionality of a polypeptide sequence to induce immunity includes other characteristics and/or activities of the sequence, such as binding to Ab1 and/or Ab3. Further, it is evident to one skilled in the art that "inducing immunity" includes any aspect of the immune response, such as a humoral response or cellular response. It is also clear that functionality of a polynucleotide sequence depends in part upon its intended use, and any functionality that is preserved in a fragment of a polynucleotide satisfies this definition. For instance, a "functionally equivalent fragment" of a 3H1 polynucleotide can be one in which an ability to hybridize is preserved, as the desired polynucleotide can be used as a probe. Alternatively, a "functionally equivalent fragment" of a 3H1 polynucleotide can mean that the polynucleotide encodes a fragment of 3H1 (which includes a portion of the variable region) that has a function associated with intact 3H1, and preferably a function associated with inducing anti-CEA immunity. A functionally equivalent fragment of a 3H1 polypeptide or polynucleotide can have the same, enhanced, or decreased function when compared to the 3H1 polypeptide or polynucleotide. Other functions of 3H1 have been listed above. A functionally equivalent fragment has at least 5 nucleotides or at least 5 amino acids, preferably has at least 10 nucleotides or at least 10 amino acids, even more preferably has at least 20 nucleotides or at least 20 amino acids.

A "cell line" or "cell culture" denotes higher eukaryotic cells gown or maintained in vitro. It is understood that the descendants of a cell may not be completely identical (either morphologically, genotypically, or phenotypically) to the parent cell.

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication nucleic acid, and expression vectors that function for transcription and/or translation of the DNA or RNA. Also included are vectors that provide more than one of the above functions.

A "host cell" includes an individual cell or cell culture which can be or has been a recipient for vector(s) or for incorporation of nucleic acid molecules and/or proteins. Host cells include progeny of a single host cell, and the progeny may not necessarily be completely identical (in morphology or in terms of total DNA complement) to the original parent cell due to natural, accidental, or deliberate mutation. A host cell includes cells transfected in vivo with a polynucleotide(s) of this invention.

"Expression vectors" are defined as polynucleotides which, when introduced into an appropriate host cell, can be transcribed and translated into a polypeptide(s). An "expression system" usually connotes a suitable host cell comprised of an expression vector that can function to yield a desired expression product.

A "signal sequence" is a short amino acid sequence that directs newly synthesized secretory or membrane proteins to and through cellular membranes such as the endoplasmic reticulum. Signal sequences are typically in the N-terminal portion of a polypeptide and are cleaved after the polypeptide has crossed the membrane.

The term "recombinant" polynucleotide as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

An "isolated" polynucleotide or polypeptide is one that is substantially free of the materials with which it is associated in nature. By substantially free is meant at least 50%, preferably at least 70%, more preferably at least 80%, and even more preferably at least 90% free of the materials with which it is associated in nature.

A "vaccine" is a pharmaceutical composition for human or animal use, which is administered with the intention of conferring the recipient with a degree of specific immunological reactivity against a particular target, or group of targets. The immunological reactivity may be antibodies or cells (particularly B cells, plasma cells, T helper cells, and cytotoxic T lymphocytes, and their precursors) that are immunologically reactive against the target or any combination thereof. For purposes of this invention, the target is tumor associated antigen CEA or any tumor related antigen bound by 3H1. The immunological reactivity may be desired for experimental purposes, for treatment of a particular condition, for the elimination of a particular substance, or for prophylaxis.

A biological "sample" encompasses a variety of sample types obtained from an individual and is typically used in a diagnostic procedure or assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, and cell lysates.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, preventing occurrence or recurrence of disease, delay or slowing of disease progression, amelioration or palliation of the disease state, and remission (whether partial or total), whether detectable or undetectable. "Treatment" can also mean prolonging survival as compared expected survival if not receiving treatment.

An "effective amount" is an amount sufficient to effect beneficial or desired clinical results. An effective amount can be administered in one or more administrations. For purposes of this invention, an effective amount of a 3H1 polynucleotide or polypeptide is an amount of 3H1 that is sufficient to induce an immune response, particularly an anti-CEA response. In terms of treatment, an "effective amount" of 3H1 polynucleotide or polypeptide is amount that is sufficient to palliate, ameliorate, stabilize, reverse or slow the progression of the CEA-associated disease state. Detection and measurement of these indicators of efficacy are discussed below.

An "individual" is a vertebrate, preferably a mammal, more preferably a human. Mammals include, but are not limited to, farm animals, sport animals, and pets.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991).

These techniques are applicable to the production of the polynucleotides and polypeptides of the invention, and, as such, are to be considered when contemplating these inventive aspects. Particularly useful systems for individual aspects will be discussed below.

3H1 Polynucleotides

The invention encompasses polynucleotides encoding the anti-idiotype antibody 3H1 or fragments of 3H1. These polynucleotides are isolated and/or produced by chemical and/or recombinant methods, or a combination of these methods. Unless specifically stated otherwise, the terms "polynucleotides" or "3H1 polynucleotides" shall include all embodiments of the polynucleotides of this invention.

The 3H1 polynucleotides of this invention are useful as probes, primers, in expression systems, and in pharmaceutical preparations, including vaccines. Especially useful applications of the polypeptides will be discussed below.

In one embodiment, the present invention provides a polynucleotide sequence encoding a polypeptide having immunological activity of a variable region of the light or heavy chain of 3H1 that contain at least a portion of a variable region of 3H1. In another embodiment, an isolated polynucleotide encoding a polypeptide having immunological activity of 3H1 is provided, wherein the polynucleotide is comprised of a sequence encoding a sequence of at least 5 amino acids of a variable light chain of 3H1. In another embodiment, an isolated polynucleotide encoding a polypeptide having immunological activity of 3H1 is provided, wherein the polynucleotide is comprised of a sequence encoding a of at least 5 amino acids of a variable heavy chain of 3H1.

The invention also provides 3H1 polynucleotides that are depicted in FIGS. 1 and 2. In one embodiment, an isolated polynucleotide encoding a polypeptide having immunological activity of 3H1 is provided, wherein the polynucleotide is comprised of a sequence encoding a sequences of at least 5 amino acids of a variable light chain of 3H1, and the variable light chain amino acid sequence is depicted in FIG. 1B (SEQ ID NO:2). In another embodiment, an isolated polynucleotide encoding a polypeptide having immunological activity of 3H1 is provided, wherein the polynucleotide is comprised of a sequence encoding a sequence of at least 5 amino acids of a variable heavy chain of 3H1, and the variable heavy chain amino acid sequence is depicted in FIG. 2 (SEQ. ID. NO:3). FIG. 1 depicts the nucleotide sequence (SEQ ID NO:1) and derived amino acid sequence (SEQ ID NO:2) of the variable region of the light chain of 3H1. FIG. 2 depicts the nucleotide sequence (SEQ ID NO:3) and derived amino acid sequence (SEQ ID NO:4) of the variable region of the heavy chain of 3H1. The nucleotide sequence of SEQ ID NO:1 is 447 base pairs and was obtained from clones as described in Example 2. The polynucleotide sequence of SEQ ID NO:3 is 462 base pairs and was obtained as described in Example 2.

In another embodiment, the invention encompasses a polynucleotide encoding a portion of the 3H1 light chain variable region, comprising at least about 70 consecutive nucleotides, preferably at least about 80 consecutive nucleotides, more preferably at least about 100 consecutive nucleotides, even more preferably at least about 150 nucleotides of SEQ ID NO:1. The invention also encompasses a polynucleotide encoding a portion of the 3H1 light chain variable region, comprising at least about 25 consecutive nucleotides, preferably at least about 30 consecutive nucleotides, even more preferably at least about 35 consecutive nucleotides of the CDR1 encoding sequence thereof. The invention also encompasses a polynucleotide encoding a portion of the 3H1 light chain variable region, comprising at least about 20 consecutive nucleotides, preferably at least about 25 consecutive nucleotides, even more preferably at least about 35 consecutive nucleotides of the CDR2 or CDR3 encoding sequence thereof.

In another embodiment, the invention encompasses a polynucleotide encoding a portion of the 3H1 heavy chain variable region, comprising at least about 70 consecutive nucleotides, preferably at least about 80 consecutive nucleotides, more preferably at least about 100 consecutive nucleotides, even more preferably at least about 150 nucleotides of SEQ ID NO:3. The invention also encompasses a polynucleotide encoding a portion of the 3H1 light chain variable region, comprising 15 consecutive nucleotides of the CDR1 encoding sequence thereof. The invention also encompasses a polynucleotide encoding a portion of the 3H1 light chain variable region, comprising at least about 20 consecutive nucleotides, preferably at least about 25 consecutive nucleotides, even more preferably at least about 35 consecutive nucleotides of the CDR2 or CDR3 encoding sequence thereof.

In another embodiment, the invention includes isolated 3H1 polynucleotides encoding a polypeptide having immunological activity of 3H1, wherein the polypeptide encodes at least 5 amino acids of a variable light chain of 3H1 as depicted in SEQ. ID. NO:2. In another embodiment, the invention includes isolated 3H1 polynucleotides encoding a polypeptide having immunological activity of 3H1, wherein the polynucleotide encodes at least 5 amino acids of a variable heavy chain of 3H1 as depicted in SEQ. ID. NO:4. The polynucleotide sequence may be similar to those depicted in SEQ ID NO:1 (FIG. 1) or SEQ ID NO:3 (FIG. 2) with minor changes designed to optimize codon usage or stability or may vary significantly. It is within the skill of one in the art, given the amino acid sequence in SEQ ID NO:2 or SEQ ID NO:4, to design such polynucleotides.

In another embodiment, the invention encompasses any of the above-described 3H1 polynucleotides, wherein the polynucleotide(s) encodes at least five amino acids of a complementarity defining region (CDR). CDRs are discussed below.

The plasmids containing cDNAs for the light and heavy chain variable regions of 3H1 (along with a portion of the constant region) have been deposited with the American Type Culture Collection (ATCC), 12301 Parklawn Drive, Rockville, Md., U.S.A. 20852 on Dec. 21, 1995 under the provisions of the Budapest Treaty for the International Recognition of the Deposit of Microorganisms for the purposes of Patent Procedure. They were accorded Accession Nos. 97394 and 97395, specifically. These deposits are made for convenience only, in that the sequence information and the teachings provided herein fully enable the claimed embodiments of the invention.

The invention includes modifications to the 3H1 polynucleotides described above such as deletions, substitutions, additions, or changes in the nature of any nucleic acid moieties. A "modification" is any difference in nucleotide sequence as compared to a polynucleotide shown herein to encode a 3H1 polypeptide fragment, and/or any difference in terms of the nucleic acid moieties of the polynucleotide(s). Such changes can be useful to facilitate cloning and modifying expression of 3H1 polynucleotides. Such changes also can be useful for conferring desirable properties to the polynucleotide(s), such as stability. The definition of polynucleotide provided herein gives examples of these modifications.

The invention encompasses 3H1 polynucleotides including fill-length (unprocessed), processed, coding, non-coding or portions thereof, provided that these polynucleotides contain a region encoding at least a portion of a variable region of 3H1. Also embodied are the mRNA and cDNA sequences and fragments thereof that include a portion of the variable region encoding segment.

The invention also encompasses polynucleotides encoding for functionally equivalent variants and derivatives of 3H1 and functionally equivalent fragments thereof which may enhance, decrease or not significantly affect properties of the polypeptides encoded thereby. These functionally equivalent variants, derivatives, and fragments display the ability to induce an immune response, preferably an anti-CEA immune response. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Nucleotide substitutions that do not alter the amino acid residues encoded can be useful for optimizing gene expression in different systems. Suitable substitutions are known to those of skill in the art and are made, for instance, to reflect preferred codon usage in the particular expression systems. In another example, alternatively spliced polynucleotides can give rise to a functionally equivalent fragment or variant of 3H1. Alternatively processed polynucleotide sequence variants are defined as polynucleotide sequences corresponding to mRNAs that differ in sequence for one another but are derived from the same genomic region, for example, mRNAs that result from: 1) the use of alternative promoters; 2) the use of alternative polyadenylation sites; or 3) the use of alternative splice sites.

The 3H1 polynucleotides of the invention also include polynucleotides encoding other 3H1 fragments. The polynucleotides encoding 3H1 fragments are useful, for example, as probes, therapeutic agents, and as a template for encoding various functional and/or binding domains of 3H1. Accordingly, the invention includes a polynucleotide that hybridizes to a polynucleotide comprised of a nucleotide sequence encoding a portion of light chain variable region of 3H1, wherein the polynucleotide is comprised of at least 10 contiguous nucleotides of SEQ. ID. NO:1. In another embodiment, the invention includes a polynucleotide that hybridizes to a polynucleotides comprised of a nucleotide sequence encoding a portion of heavy chain variable region of 3H1, wherein the polynucleotide is comprised of at least 10 contiguous nucleotides of SEQ. ID. NO:3. A fragment of this approximate size could encode for a binding site for an Ab1 or Ab3 antibody. In another embodiment, the 3H1 polynucleotide fragments comprise about 15, preferably 20, even more preferably 30 bases of the sequence depicted in FIG. 1 (SEQ ID NO:1) or FIG. 2 (SEQ ID NO:3). Suitable fragments are those which hybridize specifically to 3H1 DNA or RNA such that they are effective as primers or probes. The primers are particularly useful in the polymerase chain reaction (PCR).

Hybridization reactions can be performed under conditions of different "stringency". Conditions that increase stringency of a hybridization reaction of widely known and published in the art. See, for example, Sambrook and Maniatis. Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water.

"$T_m$" is the temperature in degrees Centigrade at which 50% of a polynucleotide duplex made of complementary strands hydrogen bonded in antiparallel direction by Watson-Crick base pairing dissociates into single strands under conditions of the experiment. $T_m$ may be predicted according to a standard formula, such as:

$$T_m=81.5+16.6\log[Na^+]+0.41(\%\,G/C)-0.61(\%\,F)-600/L$$

where $[Na^+]$ is the cation concentration (usually sodium ion) in mol/L; (% G/C) is the number of G and C residues as a percentage of total residues in the duplex; (% F) is the percent formamide in solution (wt/vol); and L is the number of nucleotides in each strand of the duplex.

Useful 3H1 polynucleotides encoding fragments of 3H1 can be obtained by generating polynucleotide fragments (based on SEQ ID NO:1 in FIG. 1 or SEQ ID NO:3 in FIG. 2, for example) and testing the polypeptides encoded thereby for the function of interest. Alternatively, given a desired 3H1 polypeptide, a polynucleotide sequence could be derived from the amino acid sequence of the 3H1 polypeptide. For example, 3H1 polypeptides can be tested for their ability to bind Ab1 and/or Ab3, or to elicit an immune response. Assays for these various functions are discussed below.

The invention also includes polynucleotides encoding 3H1 derivatives or variants which contain one or more 3H1 polypeptides, such as polynucleotides encoding scFv, polymers, fusion proteins, and chimeras. These forms of 3H1 are discussed below.

The invention also provides polynucleotides covalently linked with a detectable label. Such polynucleotides are useful, for example, as probes for detection of related nucleotide sequences.

Preparation of 3H1 Polynucleotides

The polynucleotides of this invention can be obtained using chemical synthesis, recombinant methods, or PCR.

Methods of chemical polynucleotide synthesis are well known in the art and need not be described in detail herein. One of skill in the art can use the sequences provided herein and a commercial DNA synthesizer to produce a desired DNA sequence.

For preparing 3H1 polynucleotides using recombinant methods, a polynucleotide comprising a desired sequence can be inserted into a suitable vector, and the vector in turn can be introduced into a suitable host cell for replication and amplification. Polynucleotides may be inserted into host cells by any means known in the art. Cells are transformed by introducing an exogenous polynucleotide by direct uptake, endocytosis, transfection, f-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as *PCR: The Polymerase Chain Reaction*, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), for example.

If used as a vaccine, plasmids containing 3H1 polynucleotides are prepared as described by Horn et al. ((1995) *Human Gene Therapy* 6:565–573) which produces a pharmaceutical grade plasmid DNA suitable for administration.

Cloning and Expression Vectors Comprising a 3H1 Polynucleotide

The present invention further includes a variety of vectors having cloned therein 3H1 polynucleotide(s). These vectors can be used for expression of recombinant polypeptides as well as a source of 3H1 polynucleotides. Cloning vectors can be used to obtain replicate copies of the 3H1 polynucleotides they contain, or as a means of storing the polynucleotides in a depository for future recovery. Expression vectors (and host cells containing these expression vectors) can be used to obtain polypeptides produced from the polynucleotides they contain. They may also be used where it is desirable to express 3H1 polypeptides in an individual and thus have intact cells capable of synthesizing the polypeptide, such as in gene therapy. Suitable cloning and expression vectors include any known in the art, e.g., those for use in bacterial, mammalian, yeast and insect expression systems. Specific vectors and suitable host cells are known in the art and need not be described in detail herein. For example, see Gacesa and Ramji, *Vectors*, John Wiley & Sons (1994).

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins substances, e.g., ampicillin, neomycyin, methotrexate, etc.; (b) complement auxotrophic deficiencies; or (c) supply critical nutrients not available from complex media. The choice of the proper marker gene will depend on the host cell, and appropriate genes for different hosts are known in the art. Cloning and expression vectors also typically contain a replication system recognized by the host.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide encoding a 3H1 polypeptide of interest. The polynucleotide encoding the 3H1 polypeptide is operatively linked to suitable transcriptional controlling elements, such as promoters, enhancers and terminators. For expression (i.e., translation), one or more translational controlling elements are also usually required, such as ribosome binding sites, translation initiation sites, and stop codons. These controlling elements (transcriptional and translational) may be derived from 3H1 nucleotides (i.e., the 3H1 gene), or they may be heterologous (i.e., derived from other genes and/or other organisms). A polynucleotide sequence encoding a signal peptide can also be included to allow a 3H1 polypeptide to cross and/or lodge in cell membranes or be secreted from the cell. A number of expression vectors suitable for expression in eukaryotic cells including yeast, avian, and mammalian cells are known in the art. One example of an expression vector is pcDNA3 (Invitrogen, San Diego, Calif., in which transcription is driven by the cytomegalovirus (CMV) early promoter/enhancer. This vector also contains recognition sites for multiple restriction enzymes for insertion of the 3H1 polynucleotide of interest. Another example of an expression vector (system) is the baculovirus/insect system.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (where the vector is an infectious agent, such as vaccinia virus, which is discussed below). The choice of means of introducing vectors or 3H1 polynucleotides will often depend on the host cell.

Once introduced into a suitable host cell, for example, *E. coli* or COS-7, expression of a 3H1 polypeptide(s) can be determined using any of the assays described herein. For example, presence of 3H1 polypeptide can be detected by RIA or ELISA of the culture supernatant (if the 3H1 polypeptide(s) is secreted) or cell lysates.

A particularly useful expression vector for 3H1 polynucleotides is a vaccinia virus comprised of a 3H1 polynucleotide sequence, which can also be used in vaccine preparations. Moss (1991) *Science* 252:1662–1667. To introduce polynucleotide sequences encoding 3H1 polypeptide, including 3H1 polypeptide fragments, into vaccinia, the polynucleotide sequence of interest is first inserted into a plasmid containing a vaccinia virus promoter with flanking sequences homologous to vaccinia DNA inessential for replication. Plasmid-containing cells are then infected with vaccinia, which leads to a low level of homologous recombination between plasmid and virus, with resultant transfer of the vaccinia promoter and 3H1 polypeptide-encoding polynucleotide sequence into the vaccinia virus genome. Typically, the 3H1 polynucleotide is inserted into the viral tk (thymidine kinase) gene. Insertion into the tk site attenuates the virus more than 10,000 fold compared to wild type (Flexner et al. (1980) *Vaccine* 88 (Cold Spring Harbor Laboratory), 179–184). Recombinant virus is identified by the $tk^-$ phenotype. Preferably, expression of the 3H1 polynucleotide is under the control of the vaccinia early/late promoter (7.5 K), whereby the resultant 3H1 polypeptides can be expressed in infected cells throughout the life cycle of the virus. However, other promoters known in the art can be used, such as pH6, synthetic promoters, SV40 promoters or promoters from adenovirus. Expression of the 3H1 polypeptide(s) occurs in cells infected with the recombinant vaccinia or individuals which are immunized with the live recombinant vaccinia virus. Construction of a vaccinia vector for expression of 3H1 polypeptides is provided in Example 4. Any one of several strains of vaccinia can be used, including, but not limited to, WR, ALVAC, and NYVAC. The ALVAC and NYVAC strains are used to infect avian cells.

A vaccinia vector of this invention can contain one or more polynucleotides encoding a 3H1 polypeptide(s). It can also contain polynucleotide sequences encoding other polypeptides that enhance, facilitate, or modulate the desired result, such as lymphokines, including, but not limited to, IL-2, IL-4 and GM-CSF. A preferred lymphokine is GM-CSF. If GM-CSF is used, it is also preferable to eliminate AU-rich elements from the 3' untranslated regions of RNA transcripts and/or eliminate sequences in the 5' untranslated region that are capable of forming a hairpin loop by recombinant methods. Also encompassed by this invention are vaccinia vectors encoding for recombinant 3H1 variants containing 3H1 polypeptides, such as scFvs, chimeras, and polymers (described below).

Host Cells Transformed with 3H1 Polynucleotides

Another embodiment of this invention are host cells transformed with 3H1 polynucleotides and/or vectors having 3H1 polynucleotide(s) sequences, as described above. Both prokaryotic and eukaryotic host cells may be used. Prokaryotic hosts include bacterial cells, for example *E. coli* and mycobacteria. Among eukaryotic hosts are yeast, insect, avian, plant and mammalian cells. Host systems are known in the art and need not be described in detail herein. One example of a mammalian host cell is NS0, obtainable from the European Collection of Cell Cultures (England). Transfection of NS0 cells with a plasmid, for example, which is driven by a cauliflower mosaic virus (CMV) promoter, followed by amplification of this plasmid in using glutamine synthetase provides a useful system for protein production. Cockett et al. (1990) *Bio/Technology* 8:662–667.

The host cells of this invention can be used, inter alia, as repositories of 3H1 polynucleotides and/or vehicles for production of 3H1 polynucleotides and polypeptides. They may also be used as vehicles for in vivo delivery of 3H1 polypeptides.

Plasmids Comprising Polynucleotides Encoding the Variable Region of 3H1

Also encompassed by this invention are plasmids comprising polynucleotides encoding the light chain variable region of 3H1 as deposited in ATCC Accession No. 97394. The invention also includes plasmids comprising polynucleotides encoding the heavy chain variable region of 3H1 as deposited in ATCC Accession No. 97394. Vector (plasmid) p3H1VL0 contains the nucleotide sequence encoding the light chain variable region of 3H1. Vector (plasmid) p3H1VH0 contains the nucleotide sequence encoding the heavy chain variable region of 3H 1. These polynucleotides (or fragments thereof) can be obtained by methods well known in the art. Host cells containing the vector(s) are grown under suitable conditions and the vector DNA is isolated using standard methods. Once isolated, the desired polynucleotide is obtained by an appropriate restriction enzyme digest of the isolated DNA to liberate the desired polynucleotide from the vector. A suitable separation technique such as gel electrophoresis can be used to isolate the polynucleotide from the other restriction fragments. Location of restriction sites is readily possible using sequence analysis.

Uses for and Methods Using 3H1 Polynucleotides

The polynucleotides of this invention have several uses. 3H1 polynucleotides are useful, for example, in expression systems for the recombinant production of 3H1 or 3H1 fragments. They are also useful as hybridization probes to assay for the presence of 3H1 polynucleotide (or related) sequences in a sample using methods well known to those in the art. Further, 3H1 polynucleotides are also useful as primers to effect amplification of desired polynucleotides. The polynucleotides of this invention are also useful as vaccines and for gene therapy.

3H1 polynucleotides of this invention can be used as primers for amplification of polynucleotides encoding 3H1 or a fragment thereof, such as in a polymerase chain reaction (PCR). PCR has been described above. The conditions for carrying out PCR reactions depend on the specificity desired, which in turn can be adjusted by the primer used and the reaction conditions. Such adjustments are known in the art and need not be discussed in detail herein.

3H1 polynucleotides can also be used as hybridization probes for detection of, for example, the presence of 3H1 polynucleotides in a cell. For instance, a 3H1 polynucleotide could be used as a probe to determine the presence of 3H1 polynucleotide sequences in cells used in gene therapy. For these methods, a suitable cell sample or a sample derived from cells (either of which are suspected of containing 3H1 polynucleotide sequences) is obtained and tested for the presence of 3H1 polynucleotide by contacting the polynucleotides from the sample with the 3H1 polynucleotide probe. The method is conducted to allow hybridization to occur between the 3H1 probe and 3H1 polynucleotide of interest, and the resultant (if any) hybridized complex is detected. Such methods entail procedures well known in the art, such as cell culture, polynucleotide preparation, hybridization, and detection of hybrid complexes formed, if any. Using similar methods, the probes can also be used to detect vectors which are in turn used to produce 3H1 polypeptides, intact 3H1, or recombinant, variant forms of 3H1.

The 3H1 polynucleotides of this invention can be used in expression systems to produce 3H1 polypeptides, intact 3H1, or recombinant forms of 3H1, including intact 3H1, which have enhanced, equivalent, or different, desirable properties. These recombinant forms are made by using routine methods in the art. Examples of recombinant forms of 3H1 and 3H1 polypeptides include, but are not limited to, hybrids, chimeras, single chain variants, and fusion proteins containing other components such as cytokines. A more detailed description of these recombinant forms of 3H1 and 3H1 polypeptides and how they are made is provided below.

Another use of 3H1 polynucleotides is in vaccines and gene therapy. The general principle is to administer the polynucleotide so that it either promotes or attenuates the expression of the polypeptide encoded therein. Thus, the present invention includes methods of inducing an immune response and methods of treatment comprising administration of an effective amount 3H1 polynucleotides to an individual. In these methods, a 3H1 polynucleotide encoding a 3H1 polypeptide is administered to an individual, either directly or via cells transfected with the 3H1 polynucleotide(s). Preferably, the 3H1 polynucleotide is replicated inside a cell. Thus, the 3H1 polynucleotide(s) is operatively linked to a suitable promoter, such as a heterologous promoter that is intrinsically active in cells of the target tissue type. Entry of the polynucleotide into the cell is accomplished by techniques known in the art, such as via a viral expression vector, such as a vaccinia or adenovirus vector, or association of the polynucleotide with a cationic liposome. Preferably, the 3H1 polynucleotide(s) are in the form of a circular plasmid, preferably in a supercoiled configuration. Preferably, once in cell nuclei, plasmids persist as circular non-replicating episomal molecules. In vitro mutagenesis can in turn be carried out with the plasmid constructs to encode, for example, more immunogenic molecules or T cell epitopes with a desirable HLA motif.

To determine whether plasmids containing 3H1 polynucleotides are capable of expression in eukaryotic cells, eukaryotic cells such as, for example, COS-7, CHO (avian origin), or HeLa (human origin) cells can be transfected with the plasmids. Expression resulting in a 3H1 polypeptide(s) is then determined by RIA or ELISA. Western blotting with cell lysate using 8019 (Ab1) as a probe can be performed to check for cell-associated 3H1 polypeptide. Alternatively, for smaller 3H1 polypeptides, expression can be detected, for example, by constructing the plasmid so that the resultant 3H1 polypeptide is labeled recombinantly, such as with an enzymatic label. Further characterization of the expressed 3H1 polypeptide can be achieved by purification of the 3H1 polypeptide followed by performing the functional assays described herein (e.g., cell binding inhibition assay).

This invention also encompasses ex vivo transfection of 3H1 polynucleotides, in which cells removed from individuals are transfected with vectors encoding 3H1 polypeptides and reintroduced into the individual. Suitable transfected cells include, but are not limited to, peripheral blood mononuclear cells.

Therapeutic administration of 3H1 polynucleotides is discussed in more detail below.

3H1 Polypeptides

The present invention encompasses polypeptide fragments of 3H1 containing at least a portion of a variable region of 3H1 and proteins comprising a 3H1 fragment. The polypeptide fragments of 3H1 which may comprise any region or subregion of SEQ ID NO:2 (FIG. 1) or SEQ ID NO:4 (FIG. 2) (provided that the fragments comprise at least a portion of a variable region) are identified and characterized by any (one or more) of the following criteria: (a) ability to bind to Ab1 and/or Ab3; (b) ability to induce an immune response against CEA; (c) homology (i.e., substantial sequence identity) to any part of CEA; (d) ability to palliate, ameliorate, reduce, delay, or prevent a CEA-associated tumor.

The polypeptide fragments of 3H1 have a variety of uses, including their use in pharmaceutical compositions and vaccines, as a diagnostic tool for monitoring Ab1 and/or Ab3 levels, their use in making antibody that binds to CEA and their use in removing labeled Ab1 from an individual who has received labeled anti-CEA antibody.

Unless specifically stated, the term "3H1 polypeptides" shall include all embodiments of the polypeptides of this invention. In all instances, "3H1 polypeptides" of this invention do not include polypeptides consisting of the amino acid sequence identical to intact 3H1.

The invention includes polypeptide fragments of 3H1 containing at least a portion of a variable region of 3H 1. In one embodiment, the invention provides a polypeptide having immunological activity of 3H1, wherein the polypeptide is comprised of a sequence of at least 5 amino acids of a variable light chain amino acid sequence of 3H1. In another embodiment, the variable light chain amino acid sequence of 3H1 is depicted in FIG. 1 (SEQ ID NO:2). In another embodiment, the invention provides a polypeptide having immunological activity of 3H1, wherein the polypeptide is comprised of a sequence having at least 5 amino acids of a variable heavy chain amino acid sequence of 3H1. In another embodiment, the variable heavy chain amino acid sequence of 3H1 is depicted in FIG. 2 (SEQ ID NO:4). In all of these embodiments, the polypeptide does not consist of an amino acid sequence identical to that of intact 3H1.

The amino acid sequences of SEQ ID NO:2 (FIG. 1) and SEQ ID NO:4 (FIG. 2) are presented in FIG. 3 which depicts framework and CDR sequences of the variable regions of the light and heavy chains of 3H1, respectively. The framework sequences are responsible for the correct β-sheet folding of the $V_L$ and $V_H$ domains and for the interchain interactions that bring domains together. The complementarity determining regions (CDRs) refer to six hypervariable sequences of the variable region (3 from $V_L$ and 3 from $V_H$) which together are thought to form the antigen binding site. Delineation of these regions as well as identification of the leader sequences of 3H1 was based on a search and analysis of Kabat's immunologic database by the BLAST program.

Another embodiment of the invention is polypeptide fragments of 3H1 which comprise the sequences selected from the group consisting of the amino acid sequences (fragments) depicted in FIG. 3. These polypeptides represent functional subregions of the light and heavy chain variable regions (i.e., framework and CDR). Preferably, these 3H1 polypeptides comprise a CDR.

In another embodiment, the invention includes a polypeptide fragment of the 3H1 heavy chain variable region, comprising at least 25 consecutive amino acids, more preferably 30 consecutive amino acids of SEQ ID NO:2 (FIG. 1), or 5 consecutive amino acids of the CDR1 thereof, or at least 7 consecutive amino acids, preferably at least 9 consecutive amino acids of the CDR2 or CDR3 thereof. The invention also includes a polypeptide fragment of the 3H1 light chain variable region, comprising at least 25 consecutive amino acids, more preferably 30 consecutive amino acids of SEQ ID NO:4 (FIG. 2), or 7 consecutive amino acids of the CDR2 thereof, or at least 8 consecutive amino acids, preferably 10 consecutive amino acids of the CDR1 or CDR3 thereof.

The size of the 3H1 polypeptide fragments can vary widely, as the length required to effect activity can be very small, while the maximum length typically is not detrimental to effecting activity. The minimum size must be sufficient to provide a desired function. For instance, a binding site on a polypeptide can be as small as about 5 amino acids in length, while other binding sites are formed by convergence of amino acids which are spatially proximal but not in contiguous sequence. Thus, the invention includes polypeptide fragments of 3H1 comprising a portion of the amino acid sequence depicted in SEQ ID NO:2 (FIG. 1) or SEQ ID NO:4 (FIG. 2), in which the 3H1 polypeptide is about 10, 15, 25, 30, 50, 100, or 150 amino acids in length. the invention also provides polypeptide fragments of 3H1 comprising a portion of the amino acid sequence depicted in SEQ ID NO:2 (FIG. 1) or SEQ ID NO:4 (FIG. 2) having at least about 5 amino acids and at most 100 amino acids. As is evident to one skilled in the art, these 3H1 polypeptides, regardless of their size, can also be associated with, or conjugated with, other substances or agents to facilitate, enhance, or modulate function and/or specificity of a 3H1 polypeptide. Examples of such modifications will be discussed below.

In another embodiment, polypeptide fragments are provided that contain a region of homology to CEA. Extensive sequence data on the 180-kDa CEA that is immunologically reactive with mAb 8019 are available. Paxton et al. (1987) *Proc. Natl. Acad. Sci. USA* 84:290. Such homologous fragments may at least, in part, nominally resemble the antigen CEA, and thus may participate in antigen presentation by mimicking CEA, the ultimate target antigen. These 3H1 polypeptides may also participate in antigen presentation in association with Class I major histocompatibility complex (MHC) antigens, thus triggering cytotoxic T cell killing. FIG. 19 shows alignments between similar sequences of 3H1 and CEA, when the amino acid sequences are aligned in both orientations (i.e., aligned in the same and reverse orientations). Examples of regions of homology to CEA encompassed by this invention are (amino acid numbering based on SEQ ID NO:5; FIG. 3): (a) amino acids 9–11 and 9–14, heavy chain; (b) amino acids 31–32, heavy chain; (c) amino acids 11–12 and 14–16, heavy chain (alignment in reverse orientation); (d) amino acids 16–19, light chain; (e) amino acids 29–31, light chain; amino acids 54–57, light chain; (e) amino acids 31–33, light chain (alignment in reverse orientation). Accordingly, the invention also includes 3H1 polypeptides that comprise the amino acid sequence from about amino acid 24 to about amino acid 34, about amino acid 48 to about amino acid 58, or about amino acid 12 to about amino acid 26, of the sequence depicted in FIG. 3A (SEQ ID NO:5), as well as polypeptides that comprise from about amino acid 9 to about amino acid 14, about amino acid 29 to about amino acid 37, about amino acid 50 to about amino acid 66, or about amino acid 31 to about amino acid 35 of the sequence depicted in FIG. 3B (SEQ ID NO:5). We have also found that a 3H1 polypeptide spanning the CDR-2 region of the variable region of the light chain, having the sequence IYRANRLIDGV (amino acids 48–58 of SEQ ID NO:5 in FIG. 3) stimulates T cell proliferation in mice and patients with advanced CEA-associated disease who had previously received intact 3H1 (Example 3). This polypeptide is homologous with part of the three homologous repetitive domains of CEA (Orkawa et al. (1987) *Biochem. Biophys. Res. Commun.* 142:511–518) and was identified as a region involved in idiotype-anti-idiotype contact, based on a computer algorithm based on molecular recognition theory. Thus, the invention also includes a 3H14 polypeptide having the sequence IYRANRLIDGV (SEQ ID NO:11). Typically, 3H14 polypeptides containing a region of homology to CEA will be about 8 to 20 amino acids in length.

The invention includes modifications to 3H1 polypeptides including functionally equivalent fragments of the 3H1 polypeptides which do not significantly affect their properties and variants which have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tryosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified 3H1 polypeptides are made using established procedures in the art and can be screened using standard assays known in the art, some of which are described below and in the Examples.

Figure 21A:
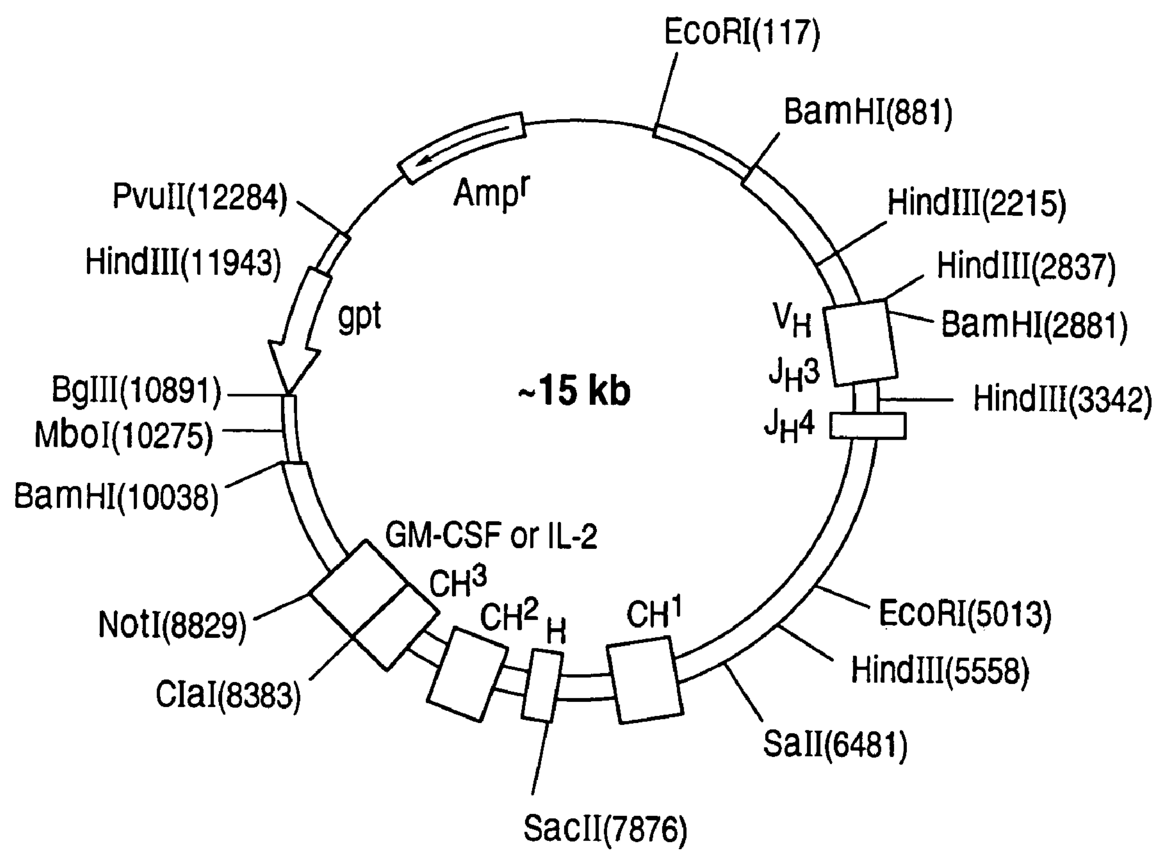
FIGS. 21A–B depicts plasmids suitable for production of a 3H1 fusion protein (A) and a chimera (B).
Figure 21B:
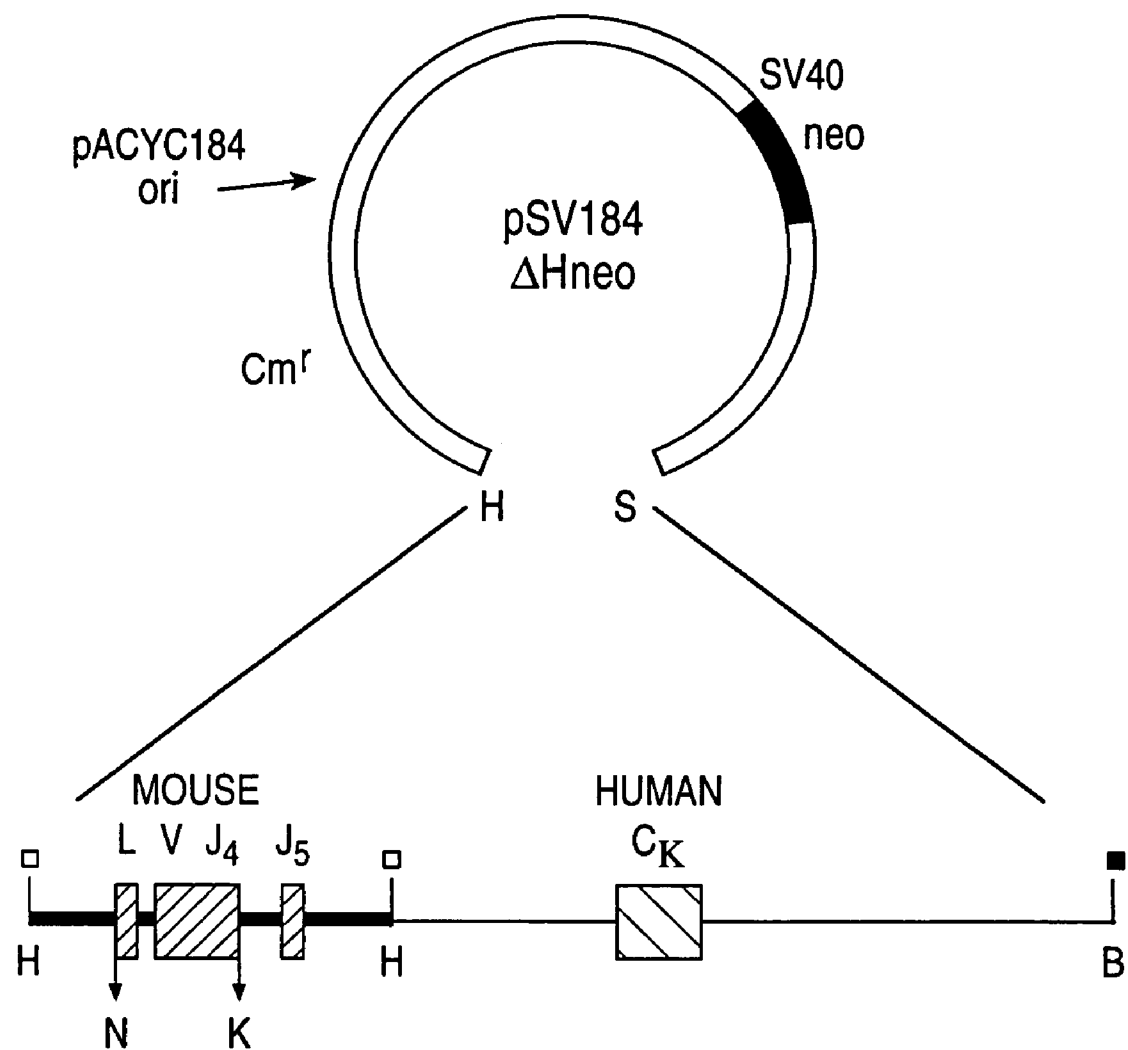

The invention also encompasses fusion proteins comprising one or more 3H1 polypeptides. In one embodiment, a fusion polypeptide is provided that comprises at least 10 contiguous amino acids of SEQ ID NO:2 (FIG. 1) and at least 10 amino acids of SEQ ID NO:4 (FIG. 2). In another embodiment, the fusion polypeptide contains a heterologous immunoglobulin constant region. For purposes of this invention, a 3H1 fusion protein contains one or more 3H1 polypeptides and another amino acid sequence to which it is not attached in the native molecule, for example, a heterologous sequence or a homologous sequence from another region. Useful heterologous sequences include, but are not limited to, sequences that provide for secretion from a host cell, enhance immunological reactivity, or facilitate the coupling of the polypeptide to an immunoassay support or a vaccine carrier. Other examples are so-called bacterial "super antigens", such as staphylococcal enterotoxin A (SEA). Dohlsten et al. (1994) *Proc. Natl. Acad. Sci. USA* 91:8945–8949. For instance, a 3H1 polypeptide can be fused with a bioresponse modifier. Examples of a bioresponse modifier include, but are not limited to, lymphokines such as GM-CSF, interleukin-2 (IL-2), interleukin 4 (IL-4), and γ-interferon. FIG. 21 depicts an example of a plasmid construct for a fusion of a 3H1 polypeptide and preferred lymphokines GM-CSF or IL-2. Co-transfection of this plasmid (which, as shown, encodes the 3H1 heavy chain) with a plasmid encoding the 3H1 light chain also yields a 3H1 fusion polypeptide. Alternatively, the plasmid of FIG. 21 can be transfected into a heavy chain loss mutant. For example, heavy chain loss mutants can be obtained by treating $2\times10^7$ 3H1 cells with fluorescein-labeled rabbit anti-mouse IgG (H chain specific, DAKO Corporation, Carpinteria, Calif.) according to the supplier's instruction. The stained and unstained cell populations are analyzed in a fluorescence-activated cell sorter. The unstained cells are collected in a sterilized tube and placed in 96-well plates with 1 cell/well by limiting dilution. The culture supernatants are then assayed by ELISA using goat anti-mouse IgG (heavy chain specific) and goat anti-mouse kappa. The clones with kappa-positive and IgG-negative phenotype are subcloned at least 3 times to obtain stable $3H1^{(-H)}$ mutants. mRNA from putative heavy chain loss mutant ($3H1^{(-H)}$) clones can be isolated and the sequence of the light chain variable region cDNA determined. Reverse PCR of the mRNA for 3H1 $V_H$ is performed with 2 sets of 5'- and 3'-primers, used for cloning of $3H1^{(-H)}$ cDNA (Example 2). A heavy chain loss mutant should yield no detectable DNA band. Transfection of these cells with the heavy chain construct can then be accomplished using standard methods in the art, such as electroporation.

A 3H1 fusion polypeptide can be created, for example, by chemical synthesis, or by creating and translating a polynucleotide in which the peptide regions are encoded in the desired relationship. These fusion proteins can be useful for enhancing, and/or facilitating an activity of a 3H1 polypeptide.

The invention also encompasses altered, recombinant forms of 3H1 comprising 3H1 polypeptide(s), that is, 3H1 polypeptides that contain at least a portion of a variable region of 3H1 as depicted in FIGS. 1 and 2. As used herein, an "altered" or "recombinant" form of 3H1 contains a 3H1 polypeptide(s) in a sequence and/or configuration that is different than that of intact 3H1. A recombinant form of 3H1 antibody included in this invention is a hybrid antibody, in which one pair of heavy and light chains is homologous to those in a first antibody, which the other pair of heavy and light chains is homologous to those in a different second antibody. For purposes of this invention, one pair of light and heavy chains is from 3H1. Typically, each of these two pairs will bind different epitopes of CEA. Such hybrids may also be formed using chimeric chains, as set forth below.

In another embodiment, 3H1 chimeras are provided in which the heavy and/or light chains are fusion proteins. Typically the constant domain of the chains is from one particular species and/or class, and the variable domains are from a different species and/or class. For instance, a "humanized" 3H1 antibody is one in which the constant region is of human origin, and the variable region is from 3H1 (i.e., murine). Also embodied within the invention is an antibody with a humanized variable region, in which the CDR regions comprise 3H1 amino acid sequences, while the framework regions are derived from human sequences. See, for example, EP 0329400. Also embodied are functional fragments of chimeras. An example is a humanized Fab fragment, which contains a human hinge region, a human first constant region, a human kappa light or heavy chain constant region, and the variable region from 3H1. The humanized 3H1 Fab fragments can in turn be made to form Fab dimers. Typically, the 3H1 fusion proteins and 3H1 chimeras of this invention are made by preparing an expressing a polynucleotide encoding them using recombinant methods described herein, although they may also be prepared by other means known in the art, including, for example, chemical synthesis.

Another example of altered, recombinant forms of 3H1 encompassed by this invention is altered antibodies, which refers to antibodies in which the amino acid sequence of 3H1 has been varied. Using standard recombinant techniques, 3H1 antibodies can be designed to obtain desired properties. For instance, a change in amino acid sequence can result in greater immunogenicity of the resultant 3H1 polypeptide. The changes range from changing of one or more amino acids to the complete redesign of a region, for example, the constant region. Changes in the constant region, in general, can attain desired cellular process characteristics, e.g., changes in complement fixation, interaction with membranes, and other effector functions. Changes in the variable region may be made to alter binding characteristics. The altered/recombinant 3H1 antibody can also be designed to aid the specific delivery of a substance (such as a lymphokine) to an effector cell. Other amino acid sequence modifications have been discussed above.

The invention also encompasses single chain variable region fragments ("scFv") of 3H1. Single chain variable region fragments are made by linking light and/or heavy chain variable regions by using a short linking peptide. Bird et al. (1988) *Science* 242: 423–426. An example of a linking peptide is $(GGGGS)_3$ (SEQ ID NO:49, which bridges approximately 3.5 nm between the carboxy terminus of one variable region and the amino terminus of the other variable region. Linkers of other sequences have been designed and used. Bird et al. (1988). Linkers can in turn be modified for additional functions, such as attachment of drugs or attachment to solid supports.

Accordingly, one embodiment of the present invention is a fusion polypeptide comprising at least 10 contiguous amino acids of SEQ. ID. NO:2 (FIG. 1) and at least 10 contiguous amino acids of SEQ. ID. NO:4 (FIG. 2), wherein the amino acid segments are joined by a linker polypeptide of about 5 to 20 amino acids. In another embodiment, the fusion polypeptide (scFv) comprises the light chain variable region of the amino acid sequence depicted in SEQ. ID. NO:2 (FIG. 1) and heavy chain variable region of the amino acid sequence depicted in SEQ. ID. NO:4 (FIG. 2).

Any peptide having sufficient flexibility and length can be used as a linker in a scFv. Usually the linker is selected to have little to no immunogenicity. Regarding the 3H1 components of scFv, all or a portion of the heavy and/or light chain can be used. Typically, the entire variable regions are included in the scFv. For instance, the light chain variable region can be linked to the heavy chain variable region. Alternatively, a portion of the light chain variable region can be linked to the entire or a portion of the heavy chain variable region. For asymmetrical linkers, such as $(GGGGS)_3$ (SEQ ID NO:49, the scFvs can be assembled in any order, for example, $V_H$-(linker)-$V_L$ or $V_L$-(linker)-$V_H$. However, if expressed in *E. coli*, there may be a difference in the level of expression of these two configurations. It is also possible to construct a hybrid, or biphasic, scFv in which one component is a 3H1 polypeptide, and another component is a different polypeptide, such as a T cell epitope. Tandem scFvs can also be made, such as (X)-(linker)-(X)-(linker)-(X), in which X are 3H1 polypeptides, or combinations of 3H1 polypeptides with other polypeptides.

The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

A particularly useful system for the production of 3H1 scFv's is plasmid vector pET-22b(+) (Novagen, Madison, Wis.) in *E. coli*. pET-22b(+) contains a nickel ion binding domain consisting of 6 sequential histidine residues, which serves as a basis for scFv purification. This example (presented in Example 5) is for illustrative purposes only, however, and is not limiting. Another example of a vector that can be used is pcDNA3 (Invitrogen, San Diego, Calif.) which has been described above.

If *E. coli* is used for scFv production, conditions should be such that the scFv polypeptide can assume optimal tertiary and quaternary structure. Depending on the plasmid used (especially the activity of the promoter) and the host cell, it may be necessary to modulate the production of the scFv. For instance, use of a weaker promoter, or expression at lower temperatures, may be necessary to optimize production of the scFv. Alternatively, expression of scFv in eukaryotic cells, such as yeast, insect, plant or mammalian, can be appropriate.

Various scFv's can be tested for binding activity by, for example, testing direct binding to Ab1, or by employing them in competition experiments described herein. Any of the assays described infra for the testing of fragments for 3H1 activity can be employed for testing scFv's. For example, radiolabeled Ab1 (8019) is reacted with $CEA^+$ cells, such as LS 174-T cells, in the absence or presence (in increasing amounts) of the scFv to be tested. The observed percent inhibition is compared to 3H1 or another Ab2. A 3H1 scFv is characterized as capable of binding if the scFv inhibits binding of Ab1 to the CEA-positive cells when compared to a negative control, such as an unrelated anti-idiotype antibody. Alternatively, scFvs can be characterized using other immunological assays described herein, such as ability to elicit an immune response. Further, svFvs can be constructed with or without an immunoglobulin leader sequence (for secretion), depending on whether a secreted or cell-associated from of scFv is desired.

In another embodiment, single chain 3H1 antibody polypeptides without a linker, or with a very short, inflexible linker, are provided. These so-called "bivalent" antibodies are unable to engage in intra-chain interaction due to the absence of a linker (or the presence of a very short linker) and thus interact with other single chains, forming "diabodies". For instance, a bivalent 3H1 antibody polypeptide can be made using recombinant methods in either of the following configurations: $V_L$-$V_H$ or $V_H$-$V_L$.

The invention also encompasses polymeric forms of 3H1 polypeptides. As used herein, a polymeric form of a 3H1 polypeptide contains a plurality (i.e., more than one) of 3H1 polypeptides. In one embodiment, linear polymers of 3H1 polypeptides are provided. These 3H1 linear polymers may be conjugated to carrier. These linear polymers can comprise multiple copies of a single 3H1 polypeptide, or combinations of different 3H1 polypeptides, and can have tandem 3H1 polypeptides, or 3H1 polypeptides separated by other amino acid sequences. These linear polymers can be made using standard recombinant methods well known in the art. In another embodiment, 3H1 multiple antigen peptides (MAPs) are provided. MAPs have a small immunologically inert core having radially branching lysine dendrites, onto which a number of 3H1 polypeptides can be anchored (i.e., covalently attached). Posnett et al. (1988) *J. Biol. Chem.* 263:1719–1725; Tam (1989) *Meth. Enz.* 168:7–15. The result is a large macromolecule having a high molar ratio of 3H1 polypeptides to core. MAPs are useful, efficient immunogens as well as useful antigens for assays such as ELISA. 3H1 MAPs can be made synthetically and can be obtained commercially (Quality Controlled Biochemicals, Inc., Hopkinton, Mass.). In a typical MAP system, a core matrix is made up of three levels of lysine and eight amino acids for anchoring 3H1 polypeptides. The MAP may be synthesized by any method known in the art, for example, a solid-phase method, for example, R. B. Merrifield (1963) *J. Am Chem. Soc.* 85:2149.

In another embodiment of the invention, the immunogenicity of the 3H1 polypeptides can be enhanced by preparing them in expression systems in which they are fused with or assembled with particle-forming proteins such as, for example, that associated with hepatitis B surface antigen. See, e.g., U.S. Pat. No. 4,722,840. Constructs wherein the 3H1 polypeptide is linked directly to the particle-forming protein coding sequences produce hybrids which are immunogenic with respect to the 3H1 polypeptide. In addition, all of the vectors prepared include epitopes specific to HBV, having various degrees of immunogenicity, such as, for example, the pre-S peptide. Thus, particles constructed from particle forming protein which include 3H1 sequences are immunogenic with respect to 3H1 and HBV. These forms of 3H1 polypeptides can be made in eukaryotic cells, such as yeast or mammalian cells.

In another embodiment, 3H1 polypeptides can be conjugated with carrier. In instances where the 3H1 polypeptide is correctly configured so as to provide a binding site, but is too small to be immunogenic, the polypeptide may be linked to a suitable carrier. A number of techniques for obtaining such linkage are known in the art and need not be described in detail herein. Any carrier can be used which does not itself induce the production of antibodies harmful to the host. Suitable carriers are typically large, slowly metabolized macromolecules such as proteins; polysaccharides, such as latex functionalized sepharose, agarose, cellulose, cellulose beads and the like; polymeric amino acids, such as polyglutamic acid, polylysine, and the like; amino acid copolymers; and inactive virus particles or attenuated bacteria, such as *Salmonella*. Especially useful protein substrates are serum albumins, keyhole limpet hemacyanin, immunoglobulin molecules, thyroglobulin, ovalbumin, tetanus toxoid, and other proteins well known to those of skill in the art. As is evident to one skilled in the art, the above-described recombinant forms of 3H1 polypeptides and 3H1, such as fusion proteins, can in turn be fused with other amino acid sequences. For instance, a 3H1 scFv can be fused to a cytokine, such as IL-2. FIG. 21 provides an example of a plasmid construct that produces such a fusion protein.

3H1 polypeptides of the invention can be identified in a number of ways. For example, the variable regions of the light and heavy chains can be screened by preparing a series of short polypeptides that together span the entire variable region amino acid sequence. By starting with, for example, 50mer or 20mer polypeptides, it would be routine to test each polypeptide for the presence of a desired property. Screening such polypeptides is well within the skill of the art. It is also known to carry out a computer analysis of a protein sequence to identify potentially interesting polypeptides, for example, homology to CEA, or a computer algorithm based on molecular recognition theory to identify putative regions associated with idiotype-anti-idiotype contact, and then prepare these polypeptides comprising these regions for testing.

Preparation of 3H1 Polypeptides

The polypeptides of this invention can be made by procedures known in the art. The polypeptides can be produced by proteolytic or other degradation of 3H1, by recombinant methods (i.e., single or fusion polypeptides) as described above or by chemical synthesis. 3H1 polypeptides, especially shorter polypeptides up to about 50 amino acids, are conveniently made by chemical synthesis. Methods of chemical synthesis are known in the art and are commercially available. For example, a 3H1 polypeptide could be produced by an automated polypeptide synthesizer employing the solid phase method.

Preferably, the polypeptides are at least partially purified from other cellular constituents. Preferably, the polypeptides are at least 50% pure. In this context, purity is calculated as a weight percent of the total protein content of the preparation. More preferably, the proteins are 50–75% pure. More highly purified polypeptides may also be obtained and are encompassed by the present invention. For clinical use, the polypeptides are preferably highly purified, at least about 80% pure, and free of pyrogens and other contaminants. Methods of protein purification are known in the art and are not described in detail herein. Alternatively, if a 3H1 polypeptide(s) is expressed in a suitable storage medium, such as a plant seed, the 3H1 polypeptide need not be purified and could even be administered without purification. Fiedler et al. (1995) *Biotechnology* 13:1090–1093.

3H1 polypeptides can be obtained from intact 3H1, which can in turn be isolated from the hybridoma (ATCC. HB12003) producing 3H1, which is described in co-owned U.S. patent application Ser. No. 08/579,940. Techniques of isolating antibodies from hybridomas are well known in the art. See, e.g., Harlow and Lane (1988). Once intact 3H1 is obtained, 3H1 polypeptides can be obtained by degradation of intact 3H1, by using, for example, proteolytic enzymes (proteinases). Examples of proteolytic enzymes include, but are not limited to, trypsin, plasmin, and thrombin. Intact 3H1 can be incubated with one or more proteinases, or the digestions can be performed sequentially. The nature and extent of the proteolytic cleavage will depend upon the desired polypeptide length as well as the enzymes used. These techniques are well known in the art. Alternatively, or in addition, intact 3H1 can be treated with disulfide reducing agents to disassociate the molecule.

3H1 polypeptides can be made by chemical synthesis using techniques known in the art.

3H1 polypeptides can also be made by expression systems, using recombinant methods. The availability of 3H1 polynucleotides encoding 3H1 polypeptides permits the construction of expression vectors encoding intact 3H1, functionally equivalent fragments thereof, or recombinant forms of 3H1. A polynucleotide encoding the desired 3H1 polypeptide, whether in fused or mature form, and whether or not containing a signal sequence to permit secretion, may be ligated into expression vectors suitable for any convenient host. Both eukaryotic and prokaryotic host systems can be used. The polypeptide is then isolated from lysed cells or from the culture medium and purified to the extent needed for its intended use. Purification or isolation of the polypeptides expressed in host systems can be accomplished by any method known in the art. For example, cDNA encoding intact 3H1 or a fragment thereof can be operatively linked to a suitable promoter, inserted into an expression vector, and transfected into a suitable host cell. The host cell is then cultured under conditions that allow transcription and translation to occur, and the desired polypeptide is recovered. Other controlling transcription or translation segments, such as signal sequences that direct the polypeptide to a specific cell compartment (i.e., for secretion), can also be used. Examples of prokaryotic host cells are known in the art and include, for example, *E. coli*. Examples of eukaryotic host cells are known in the art and include yeast, avian, insect, plant, and animal cells such as COS7, HeLa, CHO and other mammalian cells.

The polypeptides of this invention can also be expressed using recombinant vaccinia virus as a vector. This application would be especially useful in vaccine formulations, as a vaccinia virus carrier containing heterologous antigenic determinants has proven to be successful immunogens. Expression of 3H1 polypeptides in vaccinia vectors, and their use, is discussed above and infra.

Characterization of 3H1 Polypeptides

The 3H1 polypeptides of this invention can be characterized in several ways. For instance, a 3H1 polypeptide can be tested for its ability to bind to Ab1 and/or Ab3. Alternatively, 3H1 polypeptides can be tested for their ability to elicit an immune response, preferably an anti-CEA response. 3H1 polypeptides can also be tested for their ability to palliate or ameliorate CEA-associated disease, such as CEA-associated tumors. It is understood that only one of these properties need be present in order for a polypeptide to come within this invention, although more than one of these properties may be present.

The ability of a 3H1 polypeptide to bind Ab1 and/or Ab3 can be assessed several ways. In one test, binding of the 3H1 polypeptide(s) to Ab1 can be tested directly, for example, by radioimmunoassay (RIA), for example, by reacting radiolabeled 3H1 polypeptide with Ab1 or Ab3 coated on microtiter plates, as is described in Example 1. (FIG. 1).

In another procedure, binding to Ab 1 or Ab3 is determined by competitive immunoassay, In one variation of this procedure, binding of labeled 3H1 polypeptide(s) or functional equivalent fragments to Ab1 (8019) is measured in the presence of different Ab1, other Ab2s, 3H1 or analogs thereof, other 3H1 polypeptide(s), CEA or extracts containing CEA, or other proteins. Percent inhibition is calculated according to the following formula:

$$\%\ \text{inhibition} = 1 - \left(\frac{R_T - R_C}{R_{\text{MAX}} - R_C}\right) \times 100$$

In another variation, the test fragment with putative 3H1 activity is tested for its ability to interfere with the binding between Ab1 and Ab2, or Ab1 and CEA. This test may be more sensitive in some applications, because lower affinity interaction between 3H1 and Ab1 may be too weak to form a stable bond, but be adequate to interfere with the binding of another ligand-receptor pair when present at sufficient concentration. The CEA may be provided as purified antigen or CEA-expressing cells. The assay may be conducted by labeling either the Ab1 or the CEA or Ab2, and optionally immobilizing the other member of the ligand-receptor pair on a solid support for ease of separation. The test fragment is incubated with the labeled reagent, and then the mixture is presented to the immobilized target or test cell to determine if the test fragment is able to inhibit binding. Degree of inhibition correlates with 3H1 activity.

Various examples of competition assays are presented infra in the example section; One test that indicates 3H1 polypeptide activity is to measure the binding of radiolabeled Ab1 (8019) to semipurifed or purified CEA in the presence of varying amounts of 3H1 polypeptide(s). See, for example, Example 1. The Ab1-CEA mixture is then added to plates coated with 3H1 polypeptide(s) and binding is compared with binding of labeled Ab1 alone. Preferably, this test is performed with nonsaturating amounts of labeled Ab1 to detect changes in binding with small amounts of competitive CEA. An example of this test as performed with intact 3H1 is provided in Example 1. In another competition assay, CEA positive target cells (such as LS174-T or MC38cea) are grown in 96-well tissue culture plates as a confluent monolayer. Binding of radiolabeled Ab 1 (8019) in the absence and presence of 3H1 polypeptides is determined. The degree of inhibition can be compared with that of intact 3H1 or other 3H1 polypeptides. An example of this competitive assay using intact 3H1 is provided in Example 1. Another example of this assay, comparing the extent of inhibition between a 3H1 scFv and intact 3H1, is shown in Example 5.

A 3H1 polypeptide is considered to bind Ab1 if there is inhibition when compared to a negative control, such as an unrelated anti-idiotype antibody which does not bind to Ab1.

With all of the above-described assays, it is clear to one of skill in the art that the labeled molecule can be labeled in various ways, such as with radioisotopes (i.e., $^{125}$I) and non-radioactive labels, such as biotinylated molecules, and molecules for enzymatic detection, fluorescent labels and chemiluminescent labels.

The above discussed tests can also be used to compare characteristics of various 3H1 polypeptide fragments. For example, competitive assays can be conducted in which a first 3H1 polypeptide competes for binding to Ab1 (8019) in the presence of varying amounts of a second 3H1 polypeptide. Such tests can indicate relative degrees of binding affinities or other characteristics.

Another way of characterizing 3H1 polypeptides is testing their ability to generate an immune response. As used herein, "immune response" indicates either a humoral response, a cellular response, or both. As used herein, the "ability to elicit an immune response" pertains to any individual, including human.

The ability of a 3H1 polypeptide to generate a humoral response can be determined by testing for the presence of an antibody that binds to the 3H1 polypeptide(s) after administration of the 3H1 polypeptide(s). It is understood that this antibody (Ab3) was not present, or was present in lower amounts, before administration of the 3H1 polypeptide(s). Immunogenicity is preferably tested in individuals without a previous anti-3H1 response. Examples of suitable individuals include, but are not limited to, mice, rabbits, monkeys and humans. For this test, an individual is administered a 3H1 polypeptide(s). The amount per administration and number of administrations will vary, depending on the individual. Based on our previous studies using intact 3H1, a mouse requires approximately 100 μg of KLH-coupled 3H1 polypeptide in the presence of CFA and IFA per dose and three administrations. Monkeys require approximately 2 mg. For purposes of this invention the range of 3H1 polypeptide(s) that can be administered to humans is from about 10 μg to 10 mg, preferably 50 μg to 8 mg, preferably 100 μg to 5 mg, more preferably 100 μg to 2 mg.

Presence of an Ab3 can be determined by first pre-incubating sera with autologous immunoglobulin to block antibodies against isotypic and allotypic determinants and then testing sera for binding to CEA and/or the 3H1 polypeptide(s), for example, using ELISA or RIA. For instance, different dilutions of pre-reacted sera are reacted with 3H1 (or 3H1 polypeptide) coated on microtiter plates. An unrelated Ab2 serves as a control. After washing, the Ab3-3H1 complex is labeled using, for example, $^{125}$I-labeled 3H1 in a homogeneous sandwich assay. Results from this assay are compared to those obtained before administration of the 3H1 polypeptide. A more detailed description of such an assay for detection of Ab3 elicited by intact 3H1 in mice is provided in Example 1. Alternatively, binding to CEA positive cells, such as human colon carcinoma LS174-T cells, can be tested using immune flow cytometry.

Binding of Ab3 to CEA can also be determined by immunoprecipitation or immunoreactivity with CEA-positive tissue samples. For example, a semi-purified extract containing CEA is separated by SDS-PAGE and blotted to a nitrocellulose filter. The filter is then incubated with sera containing Ab3, and the reaction developed by ELISA (Example 1). If the Ab3 binds to CEA, a band of approximately 180,000 mw should appear. For testing with tissue samples, an immunoperoxidase assay can be used (Example 1).

If desired, Ab3 elicited by 3H1 polypeptide(s) can be further characterized. For example, competition assays can be performed to determine whether Ab3 share Ab1idiotopes. In this test, serum from an individual immunized with a 3H1 polypeptide is tested for inhibition of binding of labeled 3H1 polypeptide (or intact 3H1) to Ab1. Inhibition indicates that Ab3 and Ab 1 contain at least similar binding determinants. Similarly, competition of Ab3 with Ab 1 for binding to CEA (whether partially purified, purified, or on the surface of a CEA-positive cell) can be tested by coincubating a fixed amount of labeled Ab1 (8019) with different dilutions of Ab3 containing sera or Ab1 preparation and CEA (or LS174-T cells). These tests are illustrated for intact 3H1 in Example 1.

As is evident to one of skill in the art, the Ab3 can be used in turn to characterize 3H1 polypeptides, using the assays described above.

Another way of characterizing a 3H1 polypeptide is by testing its ability to elicit an antibody that is cytotoxic. For determination of complement mediated cytotoxicity (CMC), LS174-T (target) cells (i.e., cells that express CEA) are labeled with $^{51}$Cr. Labeling may be accomplished by incubating about $10^6$ cells with approximately 200 μCi $Na_2SO_4$ for 60 minutes at 37° C., followed by washing. The assay is conducted by adding and incubating serum suspected of containing antibody. Guinea pig serum pre-adsorbed with LS 174-T cells (or other source of complement) is then added. After a suitable incubation period at 37° C., extent of $^{51}$ Cr release is then measured and compared with that of unopsonized control cells. Release of $^{51}$Cr correlates with CMC activity. Herlyn et al. (1981) *Int. J. Cancer* 27:769.

Another way of characterizing a 3H1 polypeptide is by testing its ability to elicit an anti-CEA antibody that participates in an ADCC response. Cheresh et al. (1986) *Cancer Research* 46:5112–5118. In this assay, cultured human LS-174T cells (which express CEA in their surface) are labeled with $^{51}$Cr and are used as target cells. Normal human peripheral blood mononuclear cells (PBMC) are used as effector cells. Preferably, the ADCC assay is conducted in the presence of heat-inactivated serun with an effector to target cell ratio of 100:1 for 4 hours, although other suitable conditions may be used. The amount of $^{51}$Cr released is then measured.

The 3H1 polypeptides of this invention can also be characterized by their ability to elicit a cellular response. As used herein, a "cellular response" is a response that involves T cells, and can be observed in vitro or in vivo.

One way of detecting a cellular immune response is by assaying for T cell proliferative activity. In this test, cellular immune response is measured by proliferation of peripheral blood mononuclear cells (PBMs) incubated with 3H1 polypeptide(s). Peripheral blood mononuclear cells are isolated from blood after a requisite number of administrations of 3H1 polypeptide(s) and are incubated with varying concentrations of 3H1 polypeptide(s). If mice are used, T cells are obtained from spleen. T cells may be enriched, for example, by centrifugation on a gradient such as Ficoll™. A non-specific mitogen such as PHA serves as a positive control; incubation with an unrelated anti-idiotype antibody serves as a negative control. Preferably, the stimulator cells are autologous with the responder cells, particularly in terms of histocompatibility Class II antigens. After incubation of the PBMs for an appropriate number of days to allow proliferation, [$^3$H]thymidine incorporation is measured. In many instances a suitable time is five days. An example showing stimulation of T cell proliferation using a 3H1 polypeptide fragment (LCD-2; IYRANRLIDGV) (SEQ ID NO:11) is provided in Example 3. If desired, determination of which subset of T cells are proliferating can be performed using flow cytometry. Optionally, splenic T cells can be pre-depleted of either $CD4^+$ or $CD8^+$ cells before the proliferation assay by incubation with monoclonal antibody RL. 172 (anti-$CD4^+$) or mAb. 168 (anti-$CD8^+$) and complement.

Another way of detecting a cellular immune response is to test for T cell cytotoxicity (CTL) activity. In this test, T lymphocytes (i.e., an enriched T cell population) are isolated (typically from spleen cells) for use as targets in a standard 51 Cr release assay. Kantor et al. (1992) *J. Natl. Cancer Inst.* 84:1084–1091. An example of a $^{51}$Cr release assay is the following. Briefly, CEA-positive tumor cells (typically 1–2× $10^6$ cells) are radiolabeled as target cells with about 200 μCi of $Na_2\,^{51}CrO_4$ (Amersham Corp., Arlington Heights, Ill.) for 60 minutes at 37° C., followed by thorough washing to remove unincorporated isotopes. T cells and targets ($1\times10^4$/well), both resuspended in culture medium, are then be combined at various effector-to-target ratios in 96-well, U-bottom plates (Costar Corp.). The plates are centrifuged at 100 xg for 5 minutes to initiate cell contact and are incubated for 4 or 16 hours at 37° C. with 5% $CO_2$. After incubation, supernatants are collected using a Supernatant Collection System (Skatron, Inc., Sterling, Va.) and radioactivity will be quantitated in a gamma counter (Beckman Instruments). Spontaneous release of $^{51}$Cr is determined by incubation of targets in the absence of effectors, while maximum or total release of $^{51}$Cr will be determined by incubation of targets in 0.1% Triton X-100. Percentage of specific release of $^{51}$Cr is determined by the following equation:

Percent specific release=[(experimental−spontaneous)/(maximum−spontaneous)]×100.

An example of a CTL assay using 3H1 polypeptide LCD-2 (IYRANRLIDGV; SEQ ID NO:11) is provided in Example 3.

Another way of characterizing 3H1 polypeptides is testing their ability to ameliorate, delay the progression of and/or reduce the extent of CEA-associated tumors. Such tests may include inflammatory indicators, radioscintigraphy, or measurement of circulating CEA levels (such assays are available commercially).

Uses of and Methods Using 3H1 Polypeptides

3H1 polypeptides have a number of uses. 3H1 polypeptides can be used to induce an immune response in an individual, preferably an anti-CEA response. They can also be used to detect and monitor levels of Ab3, or to purify Ab3. 3H1 polypeptides are also useful for treatment of CEA-associated disease, for example, colorectal cancer, certain lung cancers (adenocarcinomas), gastric cancer, pancreatic cancers, and certain breast cancers.

Thus, the present invention includes methods of inducing an immune response in an individual comprising administering a 3H1 polypeptide in an amount effective to induce an immune response. In this context, an "effective amount" is an amount sufficient to elicit a measurable immune response, whether humoral and/or cellular. An effective amount can be administered in one or more administrations.

The invention also encompasses methods of detecting Ab3 (and/or Ab1) in a biological sample. These methods are applicable in the clinical setting, for example, for monitoring Ab1 or Ab3 levels in an individual, as well as an industrial setting, in which commercial production of Ab3 is desired. These methods entail contacting the Ab3 and/or Ab1 in the sample with a 3H1 polypeptide under conditions suitable to allow the formation of a stable complex between Ab3 and/or Ab1 and the 3H1 polypeptide, and detecting a stable complex formed, if any. A "stable" complex is a complex that is sufficiently long-lasting to persist between the formation of the complex, and its subsequent detection. A number of immunoassay methods are known in the art and have been described herein. For further illustration, a test sample potentially containing Ab3 and/or Ab1 can be mixed with a pre-determined non-limiting amount of the 3H1 polypeptide which is typically detectably labeled (such as with a radioisotope or enzyme). In a liquid phase assay, unreacted reagents are removed by a separation technique, such as filtration or chromatography. In these immunoassay techniques, the amount of label associated with the complex positively correlates with the amount of Ab3 and/or Ab1 present in the sample. Similar assays can be designed in which Ab3 and/or Ab1 in the test sample competes with labeled antibody for binding to a limiting amount of the 3H1 polypeptide. Here, the amount of label negatively correlates with the amount of Ab3 and/or Ab1 in the sample. Suitable samples in which to measure Ab3 and/or Ab1 levels are biological samples, including serum or plasma, preferably serum. Other samples include tissue samples.

Further, the invention also includes methods of purifying Ab3 (or Ab1), comprising contacting a biological sample containing Ab3 (and/or Ab1) with a 3H1 polypeptide, and obtaining a complex formed thereby, if any. Typically, the 3H1 polypeptide(s) is coupled to an affinity matrix for affinity column purification. Such methods are routine in the art and need not be described in detail herein.

Also included in this invention are methods of treating CEA-associated disease, such as a CEA-associated tumor, comprising administering an effective amount of a 3H1 polypeptide. A "CEA associated tumor" is one that contains CEA, especially expressed on the surface of tumor cells, examples of which have been described above. In this context, an effective amount for treatment is amount sufficient to palliate the disease state. An effective amount can be given in one or more than one administration. Treatment of individuals with an effective amount of 3H1 polypeptide may, for example, decrease the rate of progression of disease, in comparison with individuals not so treated.

In another embodiment, methods are provided for stimulating a T cell response in an individual having CEA-associated disease. This T cell response can be manifested as proliferation of T cells and/or promoting cytotoxic T cell activity using 3H1 polypeptides, particularly 3H1 polypeptides that are homologous to CEA. The 3H1 polypeptides can be administered directly (either as polypeptides or plasmids containing polynucleotides encoding 3H1 polypeptide(s)), or added to an ex vivo culture of suitable cells. 3H1 polypeptides are added, for example, to isolated peripheral blood mononuclear cells, in an amount effective to stimulate the desired T cell activity. The stimulated T cells are then reintroduced to the individual. The amount(s) of 3H1 polypeptide(s) added will depend upon several factors, such as the condition of the individual, previous and/or concurrent treatment procedures, and other substances used. Such amounts can be determined empirically. In using the LCD-2 polypeptide, we found significant T cell proliferation (in patients) when 0.5 to 2.0 μg/ml was used (50 μg/ml of total protein).

The polypeptides of this invention can be used alone or in conjunction with other agents which promote the desired activity/objective. 3H1 polypeptides can also be used in various combinations with each other. In this context, an "agent" can be any of a variety of substances. Further, "in conjunction with" means that the agent can be used concomitantly, before, or after the polypeptide(s). The agent can also be covalently linked to the polypeptide, such as a fusion protein; or in close physical proximity with the polypeptide. A desired activity is any activity which facilitates, enhances, promotes, or modulates the desired objective in using the 3H1 polypeptides.

Agents which may be used include, but are not limited to, cytokines, lymphokines, adjuvants, and drugs. Agents also include substances which facilitate delivery of the polypeptides, such as liposomes, or substances which promote delivery of the polypeptides to a particular target, for example, a cellular receptor. For example, one or more 3H1 polypeptides can be produced as fusion protein(s) which also contain a cytokine, such as GM-CSF. Alternatively, one or more 3H1 polypeptides can be administered with a cytokine such as GM-CSF.

The invention also encompasses methods using 3H1 polypeptides to remove a label, for example radioactivity, from an individual who has received a labeled anti-CEA antibody (Ab1), for example, for radioscintiligraphy or radiotherapy. One problem common to use of antibody targeted radionuclides (i.e., radioimmunotherapy) has been the presence of excess Ab1 in the system which limits the dosage of radiolabeled antibody for treatment. Further, effective imaging using radiolabeled antibodies is hampered due to excess circulating radiolabeled antibody, which often takes several days to clear circulation and tissues. In these methods of the present invention, 3H1 polypeptide(s) is administered to the individual at a specified time after administration of the labeled anti-CEA. The intention is for the 3H1 polypeptide(s) to complex with anti-CEA at sites other than the tumor, such as in the circulation and interstitial spaces, and thereby promote its clearance. As a result, the level of labeled moiety (such as radioisotope) in unaffected tissues is reduced, and the image of the tumor (in comparison to neighboring tissues) is enhanced. Similarly, when radionuclides are given to subjects for irradiation of a tumor site, it is desirable to reduce collateral exposure of unaffected tissue. This invention thus includes methods of treatment in which a radiolabeled anti-CEA antibody is administered in a therapeutic dose, and followed by a molar excess of 3H1.

In either of these applications, an amount of 3H1 polypeptide is chosen that is in sufficient molar excess over the labeled anti-CEA to locate and bind any anti-CEA that is not localized at the tumor site. The timing of administration and amount of 3H1 polypeptide will depend upon the nature of the radiolabeled antibody, the type of radioisotope used and the condition of the individual. Preferably, the molar ratio of 3H1 polypeptide to the anti-CEA antibody is at least about 5:1, more preferably about 25:1 to 200:1. Preferably, 3H1 polypeptide is administered 5 to 24 hours after the individual has received the anti-CEA antibody.

Pharmaceutical Compositions and Vaccines Comprising 3H1 Polynucleotides and Polypeptides The present invention encompasses pharmaceutical compositions and vaccines containing 3H1 polynucleotides and/or 3H1 polypeptides. Such pharmaceutical compositions/vaccines are useful for eliciting an immune response, and/or for treatment of CEA-associated disease, such as colorectal carcinoma. The pharmaceutical compositions/vaccines may palliate or ameliorate CEA-associated disease either alone or in conjunction with other forms of therapy, such as chemotherapy or radiotherapy. These pharmaceutical compositions, comprised of an effective amount of 3H1 in a pharmaceutically acceptable excipient, are suitable for systemic administrations to humans and animals in unit dosage forms, sterile parenteral solutions or suspensions, sterile nonparenteral solutions or oral solutions or suspensions, oil in water or water in oil emulsions and the like. Formulations or parenteral and nonparenteral drug delivery are known in the art and are set forth in *Remingtons' Pharmaceutical Sciences,* 18th Ed. Mack Publishing (1990).

A pharmaceutically acceptable excipient is a relatively inert substance that facilitates administration of a pharmacologically effective substance. For example, an excipient can give form or consistency to a vaccine composition, or act as a diluent. Suitable excipients include but are not limited to stabilizing agents, wetting and emulsifying agents, salts for varying osmolarity, encapsulating agents, buffers, and skin penetration enhancers. Examples of pharmaceutically acceptable excipients are described in *Remington's Pharmaceutical Sciences* (1990), supra.

In one embodiment, a pharmaceutical composition comprising a 3H1 polypeptide(s) is used to stimulate, for example, ex vivo cultures of peripheral blood monocytes (PBMs) from an individual. The PBM's are then reintroduced into the individual. The pharmaceutical composition is used alone or in combination with other bioresponse modifiers such as lymphokines.

One type of pharmaceutical composition is a vaccine. Accordingly, the present invention also includes vaccines comprising a 3H1 polynucleotide(s), a 3H1 polypeptide(s), or combinations of both. These vaccines are especially useful for the treatment, modulation, and/or prevention of occurrence of CEA-associated disease.

Vaccines containing 3H1 polynucleotides described above can be used for so-called "genetic immunization", or DNA vaccines, in which polynucleotides encoding an antigenic polypeptide are introduced into host cells in order to elicit a protective immune response. Tang et al. (1992) *Nature* 356: 152–154. Once in the cell nuclei, the plasmids may persist as circular non-replicating episomes leading to dose-dependent and long-lived expression. Spooner et al. (1995) *Gene Therapy* 2:173–180. Immunization using polynucleotides has been shown to generate cellular as well as humoral responses. Spooner et al. (1995); Wang et al. (1995) *Human Gene Therapy* 6:407–418. Genetic immunization has many of the advantages of live or attenuated microorganisms as vehicles for eliciting an immune response without the risk of infection.

Preferably, 3H1 polynucleotides are introduced as plasmid vectors containing appropriate control sequences for transcription and translation, such as promoters, enhancers, and signal sequences. One or more 3H1 polynucleotides can be used within a single cloning vector, and/or multiple vectors can be used. If multiple 3H1 polynucleotides are used, they should be inserted in-frame within the vector, or be under the control of separate promoters. The length and/or type of 3H1 polynucleotide used can vary and will depend upon several factors, such as the clinical objective of administering the vaccine, the condition of the individual, and the immunological profile of the individual. In addition, polynucleotides encoding other substances which will enhance, facilitate, and/or augment the immune response can also be inserted into the vector. Examples of such substances, such as GM-CSF, have been described above.

For example, in one embodiment, a polynucleotide encoding an scFv of 3H1 is inserted into one of the expression vectors (plasmids) described above. In another example, polynucleotides encoding 3H1 fragments depicted in FIG. 19 are inserted into the expression vector for administration as a vaccine. In another example, a polynucleotide encoding an immunogenic fragment of 3H1 is inserted into an expression vector.

Another type of vaccine employing 3H1 polynucleotides is so-called expression library immunization, in which an expression library of 3H1 polynucleotides (encoding various portions of 3H1) is used to immunize a host. Barry et al. (1995) *Nature* 377:632–635. The resultant multi-partite non-infectious vaccine can prove to be especially beneficial, as it presents multiple peptides as potential immunogens. Presentation of multiple immunogens has the added advantage that each particular host (i.e., individual) in which it is administered is able to select the immunologically effective polypeptides, which may vary from individual to individual. The expression library used for expression of 3H1 polypeptides can be comprehensive, that is, collectively encoding the entire 3H1 molecule, or can be partial. The expression library for immunization is made by general recombinant methods described above, using a suitable vector system. Typically, 3H1 polynucleotides are fused in frame to a signal sequence that mediates secretion.

The amount of 3H1 polynucleotide to be administered will depend upon several factors, such as the mode and route of administration (i.e., direct injection versus ex vivo culture and transfection), the 3H1 polypeptide encoded by the 3H1 polynucleotide, the condition of the individual (such as the immunological and/or disease condition), and the desired objective. Typically, if administered directly, the amount per administration is about 10 μg to 1 mg, preferably 25 μg to 500 μg, more preferably 30 μg to 250 μg, even more preferably 50 to 100 μg.

In another embodiment, 3H1 polynucleotides are used in live or attenuated viruses or viral vectors which can express an encoded 3H1 polypeptide(s) for vaccine formulations. Examples include, but are not limited to, adenovirus, adeno-associated retroviruses (AAV), and SV40. Preferably, the virus is vaccinia. Recombinant vaccinia virus can provide a powerful agent for effectively co-presenting the 3H1 polypeptide(s) encoded by the 3H1 polynucleotide(s) along with the immunogenic viral particle. Construction of vaccinia virus vectors has been described above. Generally, recombinant viral vectors are added in an amount sufficient to effect in vivo infection of host cells. The amount depends upon the type of virus used, the nature of the 3H1 polypeptide encoded, the condition of the individual, and the desired result. Recombinant vaccinia (which can encode 3H1 polypeptides or 3H1 variants containing 3H1 polypeptides, such as scFv) can be used directly for vaccination at about $10^7$ to $10^8$ plaque forming units per dose. Vaccinia can be administered parenterally, by subcutaneous or intramuscular injection, for example, as well as through mucosal membranes, such as nasally, orally or by inhalation. Alternatively, vaccinia can be administered via vaccinia-infected cells. In this technique, suitable cells, such as tumor cells, are infected with vaccinia in culture. The infected cells are then reintroduced to the individual. Methods for infecting cells with vaccinia and reintroducing these infected cells, have been described. See, e.g., Moss (1991).

Vaccines can also be prepared from one or more 3H1 polypeptides. 3H1 polypeptides can be prepared by any of the methods described above, especially by purification from a suitable expression vector. In one embodiment, the vaccines comprise one or more 3H1 polypeptide(s). 3H1 polypeptides can be formulated into a vaccine as neutral or salt forms. Pharmaceutically acceptable salts include the acid addition salts (formed with free amino groups of the 3H1 polypeptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In another embodiment, vaccines are provided that contain a 3H1 polypeptide fused to a viral particle, such as the hepatitis b surface antigen.

The preparation of vaccines which contain 3H1 polynucleotides or polypeptides as an active ingredient involves standard practice in the art. Typically, such vaccines are prepared as injectables, either as liquid solutions or suspensions; solid forms suitable for solution in, or suspension in, liquid prior to injection can also be prepared. The vaccine may also be emulsified, or the 3H1 polypeptide(s) and/or polynucleotide(s) associated with liposomes.

The 3H1 polypeptides and/or polynucleotides in the vaccines may be used neat but are often mixed with pharmaceutically acceptable excipients. Suitable excipients are, for example, water, saline, physiologically buffered saline, dextrose, glycerol, ethanol and combinations thereof. If desired, the vaccine can also contain minor amounts of auxiliary substances such as wetting or emulsifying agents, pH buffering agents, stabilizers and/or adjuvants. Examples of adjuvants include, but are not limited to, aluminum hydroxide, alum, QS-21 (U.S. Pat. No. 5,057,540), DHEA (U.S. Pat. Nos. 5,407,684 and 5,077,284) including its precursors and modified forms (e.g., DHEA-S, the sulfonated form of DHEA), beta-2 microglobulin (WO 91/16924), muramyl dipeptides, muramyl tripeptides (U.S. Pat. No. 5,171,568), monophosphoryl lipid A (U.S. Pat. No. 4,436,728; WO 92/16231) and its derivatives, such as and DETOX™, and BCG (U.S. Pat. No. 4,726,947). Other suitable adjuvants include, but are not limited to, aluminum salts, squalene mixtures (SAF-1), muramyl peptide, saponin derivatives, mycobacterium wall preparations, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873–875. For veterinary use and for production of antibodies in animals, mitogenic components of Freund's adjuvant can be used. The choice of an adjuvant will depend, in part, on the stability of the vaccine in the presence of the adjuvant, the route of administration, and the regulatory acceptability of the adjuvant, particularly when intended for human use. For instance, alum is approved by the United States Food and Drug Administration (FDA) for use as an adjuvant in humans. For enhancing the immune response using a vaccine containing a 3H1 polynucleotide, encapsulation in cationic lipids can be used. For delivery of 3H1 polypeptides, encapsulation in liposomes can also be appropriate. Liposomes suitable for packaging polynucleotides and/or polypeptides for delivery to cells are known in the art.

3H1 polypeptide(s) can optionally be treated chemically to enhance its immunogenicity, especially if a 3H1 polypeptide comprises 100 amino acids or less. Such treatment may include cross-linking, for example, with glutaraldehyde; linking to a protein carrier, such as keyhole limpet hemaocyanin (KLH) or tetanus toxoid.

If a sub-optimal immune response is deemed to be due to suppressor T cells induced by a vaccine of this invention, cyclophosphamide (100 mg/kg body weight) can also be administered interperitoneally.

The vaccines of the present invention are typically administered parenterally, by injection for example, either subcutaneously, intramuscularly, intraperitoneal or intradermally. Administration can also be intranasal, intrapulmonary (i.e., by aerosol), oral and intravenous. Additional formulations which are suitable for other modes of administration include suppositories and, in some cases, oral formulations. The route of administration will depend upon the condition of the individual being treated and the desired clinical effect.

Administrations can begin on a weekly or biweekly basis until a desired, measurable parameter is detected, such as elicitation of an immune response (humoral and/or cellular). Administration can then be continued on a less frequent basis, such as biweekly or monthly.

The vaccines are administered in a manner compatible with the dosage formulation, and in such amount as will be prophylactically and/or therapeutically effective. The quantity to be administered depends on the individual to be treated, the capacity of the individual's immune system to synthesize antibodies, the route of administration, and the degree of protection desired. Precise amounts of active ingredient required to be administered may depend on the judgment of the practitioner and may be peculiar to the individual. General dosage ranges for 3H1 polynucleotides and polypeptides have been given above.

Typically, the vaccine is administered as a series of doses, beginning with a group of doses to prime the immune response, followed by less closely spaced "maintenance" doses. For example, the vaccine can be administered on a weekly basis to establish an immune response, followed by bi-weekly or monthly injections to maintain the response.

The polypeptides and/or polynucleotides in the vaccines can be given alone, in combination with other 3H1 polypeptides and/or polynucleotides, in combination with intact 3H1 and/or in combination with other substances, such as lymphokines and drugs, that enhance, facilitate, or modulate the desired effect. Examples of such substances have been described above. 3H1 polypeptides can be combined by preparing a mixture of the 3H1 polypeptides in solution or by synthesizing a fusion protein.

The vaccines of this invention can also be administered in conjunction with recombinant vaccinia containing a polynucleotide encoding CEA or a fragment thereof and/or recombinant vaccinia containing a polynucleotide encoding a lymphokine such as GM-CSF. Further, it is understood that the vaccines of this invention can be used in conjunction with other modes of therapy, whether established or experimental. Such use is indicated, for example, when administration of the vaccine improves the clinical results as compared to administration of other mode(s) of therapy alone, such as chemotherapy or radiotherapy.

The immunogenicity of a 3H1 vaccine can be monitored by measuring levels of Ab3 and/or monitoring the disease state. Detection and measurement of Ab3 using RIA or ELISA and measurement of T cell activity (i.e., proliferation and/or cytotoxic activity) has been described above. As an example, Ab3 can be quantitated as follows. Microtiter plates are coated with 8019 (Ab1) and reacted with a fixed amount of $^{125}$I-labeled 3H1 polypeptide. A standard inhibition curve is generated using purified 8019 as the inhibitor. Sera at different dilutions is tested for ability to inhibit the Ab1-Ab2 reaction and the amount of Ab3 in the sera is estimated from the standard inhibition curve. Alternatively, T cell response can be measured using any of the assays described above. The disease state can be monitored using standard techniques in the art, such as measurement of a tumor-associated marker, X ray, CT scan, and other measurable clinical manifestations.

It is recognized that a number of alternative vaccine compositions, not limited to those described herein, may be efficacious in inducing an immune response. All such compositions are embodied within the present invention, providing they include a 3H1 polynucleotide or polypeptide as an active ingredient.

Kits Comprising 3H1 Polynucleotides and/or 3H1 Polypeptides

The present invention also encompasses kits containing 3H1 polynucleotides and/or polypeptides. Diagnostic procedures using the 3H1 polynucleotides or polypeptides of this invention can be performed by diagnostic laboratories, experimental laboratories, practitioners, or private individuals. Kits embodied by this invention include those that allow someone to conduct an assay for anti-CEA or anti-3H1 activity, such as any of those disclosed herein, thus detecting an/or quantitating those activities. The kits embodied by this invention also include kits that allow detection of 3H1 polynucleotides in, for example, ex vivo or in vivo transfected cells.

For example, the presence of Ab3 in a biological sample can be tested for using a 3H1 polypeptide. The sample can optionally pre-treated for enrichment of Ab3.

The kits of this invention comprise a 3H1 polynucleotide(s) or polypeptide(s) in suitable packaging. The kit may optionally provide additional components that are useful in the procedure. These optional components include, but are not limited to, buffers, capture reagents, developing reagents, labels, reacting surfaces, means for detection, control samples, instructions, and interpretive information.

The following examples are provided to illustrate but not limit the present invention.

EXAMPLES

Example 1

Generation and Characterization of 3H1 Anti-Idiotype Antibody

The monoclonal anti-idiotype antibody producing hybridoma cell line 3H1 was created and identified according to the following description. Aspects of both the immunization procedure and the screening procedure were important to obtain an antibody with the desired specificity and functionality. 3H1 was one of a number of Ab2 that were initially produced, and was identified as the candidate with the most desirable features.

3H1 was obtained by using the 8019 antibody as immunogen for an anti-idiotype response. 8019 binds to a unique epitope of CEA that is not present on other members of the CEA family, with virtually no cross-reactivity with normal adult tissues or hematopoietic cells including granulocytes. Koprowski et al. (1979) *Somatic Cell Genet.* 5:957; Mitchell (1980) *Cancer Immunol. Immunother.* 10:1.

The immunizing antibody (Ab1) was the mouse anti-CEA monoclonal antibody 8019. Since the responding animal was also a mouse, the Ab2 generated were expected to be directed against idiotypic features of 8019. However, only a fraction of those would be directed against the 8019 paratope, an even smaller proportion would be immunogenic and capable of eliciting an Ab3, and a still smaller proportion would elicit Ab3 that cross-reacted with the tumor-associated antigen.

To render 8019 sufficiently immunogenic in an autologous species, it was conjugated to the carrier KLH, and emulsified in Freund's adjuvant. It was administered repetitively into the recipient animals on an unusual schedule with only 2 weeks between doses. Five mice were immunized according to this schedule. Substantial responses arose in about 3 mice only after the fourth immunization. Responding animals were boosted with a fifth dose of 8019 i.v., spleen cells were isolated, and hybridomas were prepared separately from each animal. Cloning was performed according to standard techniques.

The screening procedure comprised four important steps: (1) Positive selection for antibody binding to 8019 (2) Negative selection against antibody recognizing isotypic or allotypic determinants; (3) Positive selection for an ability to inhibit the binding of 8019 to CEA; (4) Positive selection for an ability to induce a humoral immune response against the original tumor-associated antigen (CEA) in both mice and rabbits. The rest of this section provides an overview of the screening procedure, which is given in more detail in the sections that follow.

Initial screening was conducted by immunoassay to identify the clones that reacted with 8019, but not with other target monoclonal antibodies sharing the same allotypic or isotypic determinants. A critical assay was a sandwich RIA in which 8019 is attached to a solid phase, overlaid with culture supernatant, and developed with radioiodinated 8019. This assay requires the antibody in the hybridoma supernatant to be functionally bivalent, and be able to span between the capture 8019 and the developing 8019. Several clones that were idiotype specific and gave a strong signal in this assay were selected for further study.

Subsequent screening was conducted by competition assays, in which the Ab2 was required to block the binding of 8019 to CEA. This established that Ab2 recognized the paratope of 8019. CEA was provided in the form of MCF-7 cells, a human breast cell tumor line expressing CEA at the cell surface. The nature of the assay requires the Ab2 to block the interaction between 8019 and the tumor antigen in its particular manner of presentation on tumor cells. At a minimum, candidate Ab2 which had passed the earlier screening tests were required to inhibit the binding of 8019 to the cells by at least 85%. There were about three Ab2 that substantially exceeded the minimum, with 3H1 providing about the highest level of inhibition.

The ultimate screening test was a determination of whether the candidate Ab2 were capable of eliciting an Ab3 of the desired specificity when injected into a recipient. Sufficient quantities of Ab2 were prepared from mouse ascites, and tested in mice and rabbits. Sera from the test animals were first assayed for the presence of Ab3 in a sandwich immunoassay using the same labeled Ab2 used for immunization. Sera testing positively were then assayed for ability of the Ab3 to react against the tumor-associated antigen; namely CEA. A semipure preparation of CEA was used to coat microtiter plates, overlayed with the test serum in serial dilutions, and the Ab3 that bound was detected using labeled anti-immunoglobulin. The titer of the Ab3 binding to CEA defined the "quality" of Ab2, as a reflection of its capacity as an inducer of anti-CEA.

Monoclonal antibody 3H1 emerged as the anti-idiotype with the highest quality, and is the original basis for various compounds, compositions, and procedures embodied in this invention.

Materials

Carinoembryonic antigen (CEA): Purified CEA was obtained commercially from Rougler Biotech, Montreal, Canada (cat. no. 70015). Alternatively, CEA was isolated from human liver metastasis of colonic adenocarcinoma by perchloric acid extraction and purified twice by ion-exchange chromatography, followed by gel filtration and several steps of HPLC chromatography. CEA obtained by this method was 100% pure, produced a single band at 180,000 m.w. by HPLC and SDS-PAGE and was immunoprecipitated as a single band by horse as well as rabbit anti-CEA antibody. Two closely migrating bands of 180,000 and 200,000 m.w. were demonstrated by Western blot analysis using 8019 antibody and other murine mAb anti-CEA. The purified CEA was used for ELISA experiments with mouse and rabbit polyclonal Ab3 sera, described supra.

Other experiments were generally conducted using a semipurifed extract from human adeoncarcinoma cells. This was prepared by perchloric extraction followed by extensive dialysis. The presence of CEA in the extract was confirmed by SDS-PAGE, followed by immunoprecipitation with mAb 8019.

Antibody. The hybridoma cell line producing monoclonal antibody 8019 was obtained from the American Type Culture Collection (ATCC, Rockville, Md.). The antibody was originally described as an IgM κ, but during recloning a spontaneous switch mutant appeared, and our 8019 is an IgG1 κ. The specificity of 8019 was reconfirmed by immunoperoxidase staining and flow microfluorimetry analysis using cells expressing CEA. Monoclonal antibody 1E3 mAb (IgG1κ; specific for human mucinous ovarian carcinoma) and other monoclonal and myeloma mouse immunoglobulins were used as controls in various experiments herein described.

Ascites of 8019 hybridomas and other cell lines were prepared by injecting individual pristane-primed mice i.p. with 2-10×10$^6$ viable cells. The IgG fraction was isolated from ascites by 45% saturated ammonium sulfate precipitation and subsequent chromatography on Protein A Sepharose(TM) CL-4B (Ey et al. (1978) *Immunochemistry* 15:429). The purity of the isolated IgG was checked by immunodiffusion, immunoelectrophoresis, and high pressure liquid chromatography (HPLC) fractionation.

Preparation of F(ab')$_2$ fragments of 8019: The F(ab')$_2$ fragments were prepared by standard pepsin digestion (Parham (1983) *J. Immunol.* 131:2895). Briefly, the IgG fraction from the 8019 ascites was dialyzed against 0.1 M citrate buffer, pH 3.5, and digested with pepsin (25 μg/mg IgG) at 37° C. for 8 h. After cleavage, the pH was adjusted to 7.0 with 3.0 M tris buffer, pH 8.6, and the solution was dialyzed against phosphate-buffered saline (PBS) in the cold. The digest was separated by HPLC using a Sepharose 6 column. The purity of the isolated F(ab')$_2$ was determined by immunodiffusion and by reaction with anti-isotype reagents in a standard ELISA.

Coupling of antibody with KLH: 8019 was coupled to keyhole limpet hemocyanin (KLH) according to a method described by Maloney et al. (1985; *Hybridoma* 4:191). Antibody stock solution (1 mg/ml) was mixed with KLH (1 mg/ml) in PBS in the presence of freshly diluted glutaraldehyde solution (final concentration 0.05%). The mixture was rotated end-over-end for 1 h at room temperature, and then dialyzed exhaustively against PBS at 4° C. Immunization of syngeneic BALB/c mice: BALB/c females were immunized four times over a period of 2 months. The first injection was given i.p. using 100 μg of 8019, emulsified in complete Freund's adjuvant. The next two injections were given with 100 μg of 8019 coupled to KLH in incomplete Freund's adjuvant, either s.c. or i.p. Mice were bled from time to time, and sera were checked for anti-Id activity by ELISA in a binding assay by using F(ab')$_2$ fragments of 8019 and normal pooled BALB/c mouse serum IgG as control. Three days before the fusion, the mice were boosted i.v. with 8019 in PBS.

Production of Anti-Idiotype Hybridomas

The fusion partner used to produce the hybridoma lines was the mouse non-secretory myeloma cell line P3-653, ancestrally related to P3X63Ag8.653, available from the ATCC as No. CRL-1580. Established human cell lines were cultured in RPMI 1640 supplemented with 5% fetal calf serum as described elsewhere (Seon et al. (1984) *J. Immunol.* 132:2089).

Hybridomas were produced essentially following the method of Oi and Herzenberg ((1980) "Selected Methods of Cellular Immunology", Mishell & Shiigi eds., Freeman Publs., at 351–372). Spleen cells from immunized mice were mixed with P3-653 cells at a ratio of 1:1 to 1:10, in the presence of 50% polyethylene glycol (PEG, mw ~4500). Fused cells were then washed and cultured. Hybrids were selected using hypoxanthine-aminopterin-thymidine media.

Initial Selection of Anti-Idiotype Antibody (Ab2) Secreting Hybridoma Clones:

Initial screening of the hybridoma clones was performed by RIA and ELISA. The ELISA was conducted by coating microtiter plate wells with 8019 antibody (or control) at 500 ng/well. After incubating overnight at 4° C., the plates were blocked with 1% bovine serum albumin (BSA) in PBS. 100 μl of hybridoma culture supemates or 20× concentrate was incubated in the well for 4 h at room temperature. After washing with PBS, the plates were further incubated for 4 h at room temperature or overnight at 4° C. with alkaline phosphatase-labeled anti-isotype reagents, and developed with the substrate. Because the ELISA detecting reagents were anti-mouse immunoglobulin, the 8019 used to coat the plates was an $F(ab')_2$ fragment. The ELISA assay is useful in identifying the class and subclass of specific antibody. Generally, antibody of certain IgG subclasses is desired because it is stable, easily purified by protein A chromatography, and may have useful effector functions.

Hybridoma supernatants were also tested in a sandwich RIA. Purified 8019 was radioiodinated by the chloramine T method (Hunter (1970) *Proc. Soc. Exp. Biol. Med.* 133:989). 8019, or control antibody (monoclonal antibodies of various isotypes and unrelated specificities, and BALB/c normal IgG) was coated onto PVC plates at 500 ng/well. Generally, intact antibody was used. After incubating overnight at 4° C., the plates were blocked with 1% BSA in PBS. Coated plates were incubated with serial dilutions of hybridoma supernatant for 4 h, and developed using ~50,000 cpm of $^{125}$I-8019. The RIA assay is a more stringent specificity test for the antibody, and also requires that the antibody be able to span between two 8019 molecules.

A number of monoclonal Ab2 secreting cell lines emerged from these screening assays with the desired properties. Amongst them was monoclonal antibody 3H 1.

Confirmation that Ab2 are Specific for 8019 Idiotype

Figure 6:
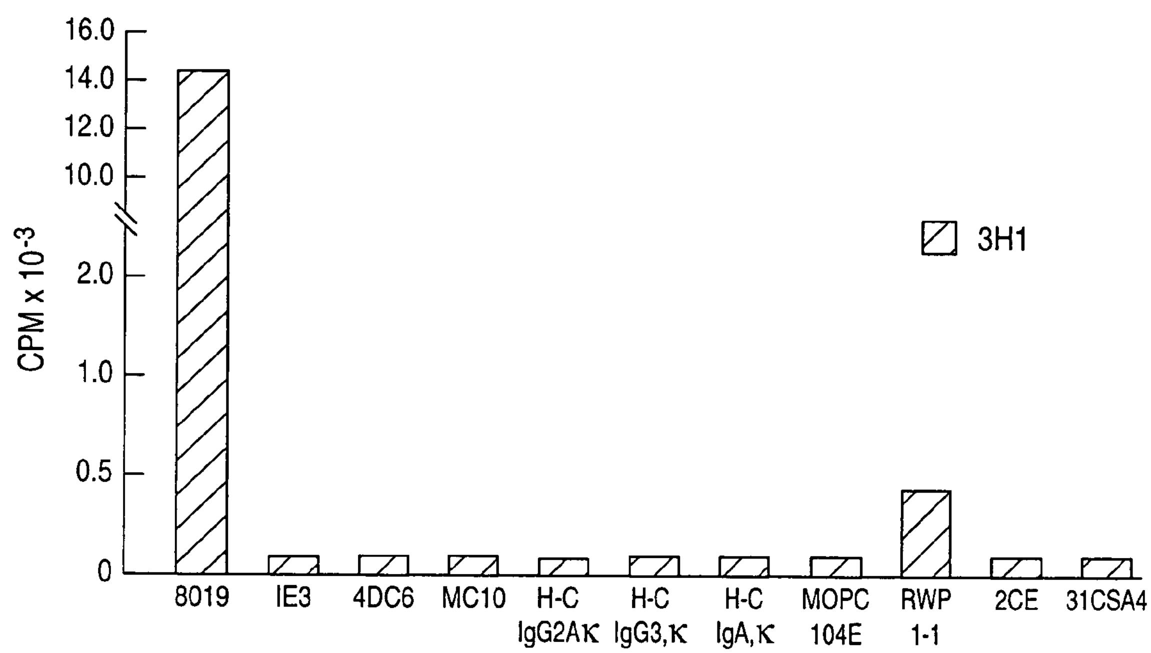
FIG. 6 is a bar graph comparing the reactivity of 3H1 with various antibodies. $^{125}$I-3H1 was tested against a panel of mAb of various specificities belonging to major Ig subclasses by a direct binding RIA.

Idiotype specificity of Ab2 was confirmed by direct binding to Ab1. Various purified Ab2 were labeled with $^{125}$I, and tested for binding to plates coated with a panel of monoclonal anti-TAA Ab1. Results for an experiment using $^{125}$I-3H1 are shown in FIG. 6. The results are presented in mean cpm (n=3, S.D.<10%). 3H1 bound almost exclusively to 8019; there was virtually no cross-reactivity with any of the other Ab1 tested, with a single exception: Minor cross-reaction with anti-CEA antibody RWP 1.1 (IgG2b, κ) that recognizes a related (possibly overlapping) epitope on CEA.

Specificity for the 8019 idiotype was further established in competition experiments. ~25,000 cpm of various labeled Ab2 was mixed with different members of a panel of unlabeled competitors comprising Ab2, Ab1, and other mouse immunoglobulins. The Ab2 was then tested for binding to 8019 coated plates. Results are shown in Table 1 (mean cpm, n=3, S.D.<10%). Greater than 90% inhibition was obtained using 250 ng of unlabeled 3H1 or 8019 as competitor. Virtually no inhibition was obtained, up to a concentration of 5 μg, using the other immunoglobulins as potential competitors, except for the related Ab1 antibody RWP 1.1.

TABLE 1

Inhibition of Id-anti-1d binding*

| Inhibitor | cpm Bound | Percent Inhibition |
|---|---|---|
| None | 11,995 | 0 |
| 3H1 (Ab2), 0.125 μg | 439 | 97 |
| 8019 (Ab1), 0.200 μg | 861 | 95 |
| RWP 1.1, 5 μg (anti-CEA) | 1,842 | 85 |
| 1E3, 5 μg (anti-iso, allotype) | 11,755 | 2 |
| Mc-10, 5 μg (anti-iso, allotype) | 12,085 | 0 |
| F36/22, 5 μg (anti-iso, allotype) | 11,558 | 4 |
| 3F3, 5 μg (anti-CEA) | 10,955 | 8 |
| ZCE, 5 μg (anti-CEA) | 12,033 | 0 |
| 31C5A4, 5 μg (anti-CEA) | 11,800 | 1 |
| D-14, 5 μg (anti-CEA) | 12,075 | 0 |

Screening for Anti-Idiotypes Directed Against the 8019 Paratope

To determine whether the Ab2 were directed against the paratope of 8019, the Ab2 were used to compete for the binding of radiolabeled 8019 to CEA. This was performed two ways: (1) plate-binding assays were conducted using the semipurified CEA extract; (2) cell binding assays were conducted using LS174T cells, a human colon cancer cell line expressing CEA as a membrane constituent Plate-binding assays were coated by incubating plates with 100 μl of the perchloric acid solubilized semipurified CEA Ag extract (0.1 mg protein/ml) overnight at 4° C. LS174-T cells were grown as confluent monolayer in 96-well tissue culture plates. Various dilutions of the test Ab2 (either culture supernatant or purified antibody) were mixed with the labeled 8019, and then added to the coated plate or cultured cells. Percent inhibition of the assay was calculated according to the formula:

$$\%\ \text{inhibition} = 1 - \left(\frac{R_T - R_C}{R_{MAX} - R_C}\right) \times 100$$

where $R_T$ is the average cpm of the experimental well with inhibitors; $R_C$ is the average background cpm; and $R_{MAX}$ is the average maximum binding without any inhibitors.

Figure 7:
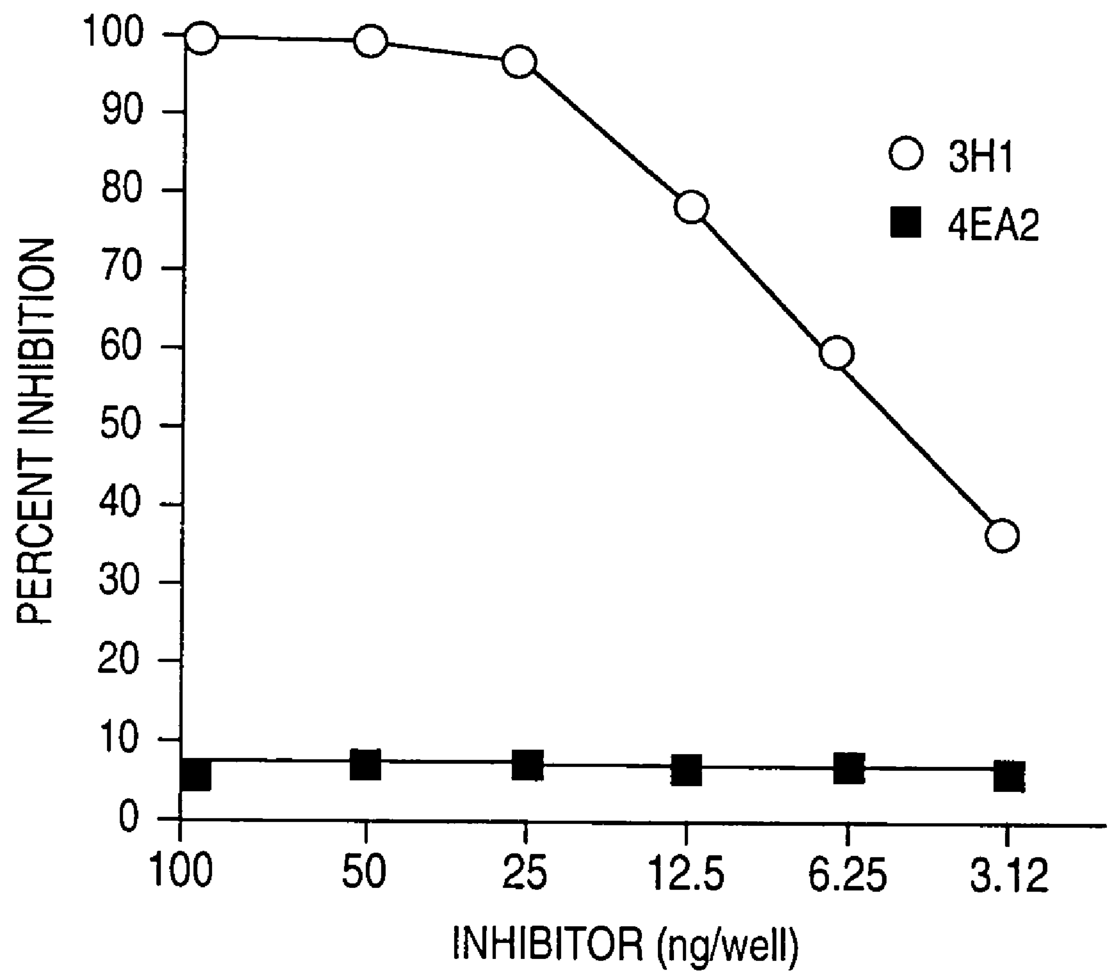
FIG. 7 is a graph depicting inhibition of binding of radiolabeled 8019 (Ab1) to semipurified CEA by 3H1. Circles denote 3H1; squares denote 4EA2, an unrelated anti-idiotype antibody. 3H1 inhibited the binding 100% beginning at a concentration of 25 ng.

FIG. 7 shows results of this type of experiment, conducted using 3H1 as the model competitor in the plate-binding assay. 3H1 inhibited the binding of labeled 8019 to the CEA at amounts as low as 25 ng. Purified antibody 4EA2 (an IgG1,k of unrelated specificity) was used as a negative control, and demonstrated no inhibition. In a related experiment, 3H1 was not able to inhibit the binding of another anti-CEA antibody (D14) to the CEA-coated plates.

Confirmation of the Binding Specificity

For the most promising Ab2, confirmation experiments were conducted to confirm the specificity of binding to 8019, in which the roles in the competition assay were reversed.

About 40,000 cpm of $^{125}$I-8019 was coincubated with a semipurified preparation of CEA Ag, or else with a nonrelated glycoprotein Ag that does not react with 8019 (Bhattacharya et al. (1982) *Cancer Res.* 42:1560). The antibody-Ag mixture was added to Ab2-coated plates (500 ng/well), and the ability of CEA to inhibit the binding was determined. The amount of Ab2 was non-limiting with respect to the amount of 8019 that could bind, and was therefore a sensitive indicator for small amounts of competing CEA.

Figure 8:
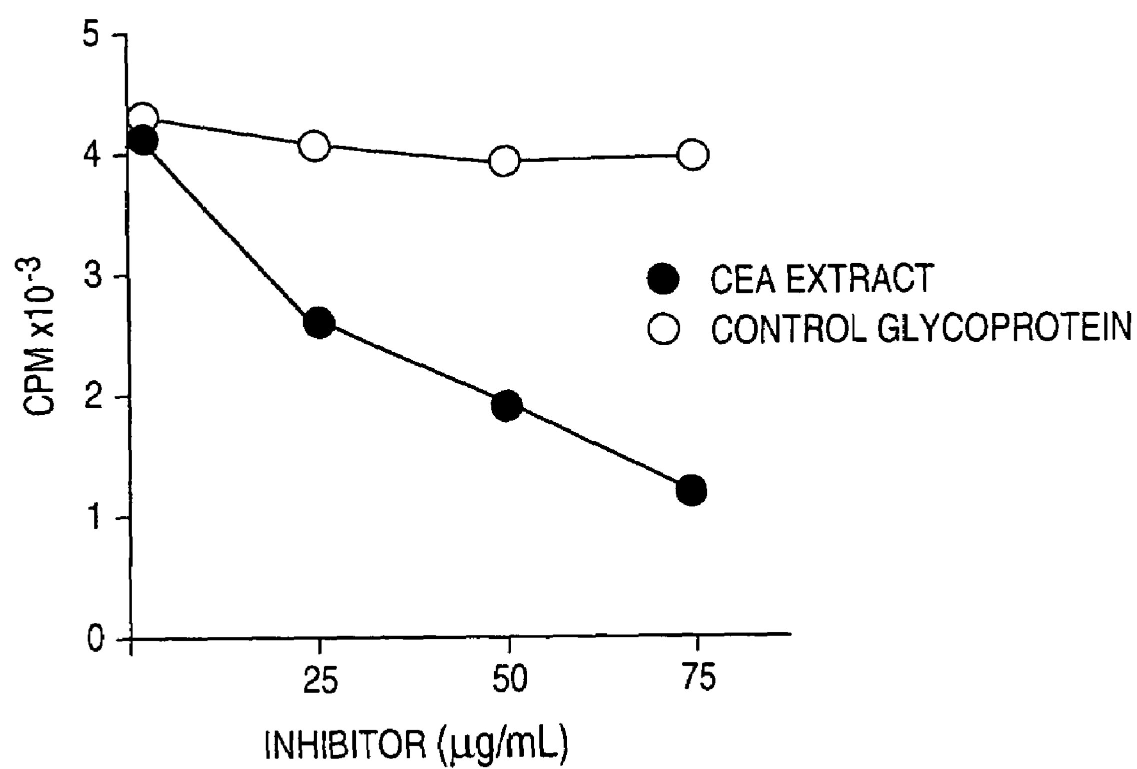
FIG. 8 is a graph depicting the inhibition of binding of 8019 (Ab1) to CEA by 3H1. Closed circles denote semipurified CEA; open circles denote a control glycoprotein that does not bind to 8019. Semipurified CEA at 2.5 μg inhibited the binding of anti-Id 3H1 to iodinated 8019 by 50%, whereas the unrelated glycoprotein even at higher concentration did not inhibit binding.

FIG. 8 shows the results of a typical experiment. 2.5 μg of semipurified CEA inhibited the binding of a 3H1 to iodinated 8019 by 50%. The unrelated glycoprotein even at higher concentration did not inhibit binding. This suggests that 3H1 is a binding site-specific anti-Id.

Antibody-producing clones testing positively in the screening tests described so far were used to prepare mouse ascites as a source of Ab2. The Ab2 were purified by chromatography using Protein A and Protein G affinity resins by standard techniques.

Screening for Anti-Idiotypes Capable of Eliciting a Tumor-Specific Immune Response If the Ab2 behaves as a network antigen, then it should induce the production of Ag-specific Ab3 in the absence of exposure to Ag in a genetically unrestricted way and across species barriers. Accordingly, Ab2 that had passed previous screening tests were screened further in immunization experiments. The objective is to identify the candidates that can elicit Ab3 sharing idiotypes with Ab1, and exhibiting a similar binding specificity for the tumor-associated antrigen.

For each Ab2 to be tested, a minimum of 5 BALB/c mice and two New Zealand white rabbits were immunized. For immunization of mice, the Ab2 was conjugated to KLH. 50 μg was injected, and the mice were bled periodically to test the response. 500 μg was injected per rabbit, emulsified in complete Freund's adjuvant on day 0, in incomplete Freund's adjuvant on day 14, and in saline (i.m.) during the next 2 months. The rabbits were bled 14 days after the last injection.

Anti-CEA activity was measured by ELISA (see generally Engvall et al. (1972) *J. Immunol.* 109:129). Various dilutions of test sera were incubated in CEA coated wells, and antibody bound was detected with enzyme-linked anti-immunoglobulin appropriate for the species. This assay requires the antibody to bind the original tumor-associated antigen, and establishes that at least a portion of the Ab3 induced by immunizing with the anti-idiotype is tumor antigen specific. The level of CEA-specific Ab3 was titered by serial dilution, and defined the "quality" of the immunizing Ab2. Sera from mice and rabbits immunized with an unrelated monoclonal antibody (4EA2) was used as a negative specificity control The 3H1 monoclonal antibody emerged as having the highest quality amongst the candidates tested.

Figure 9:
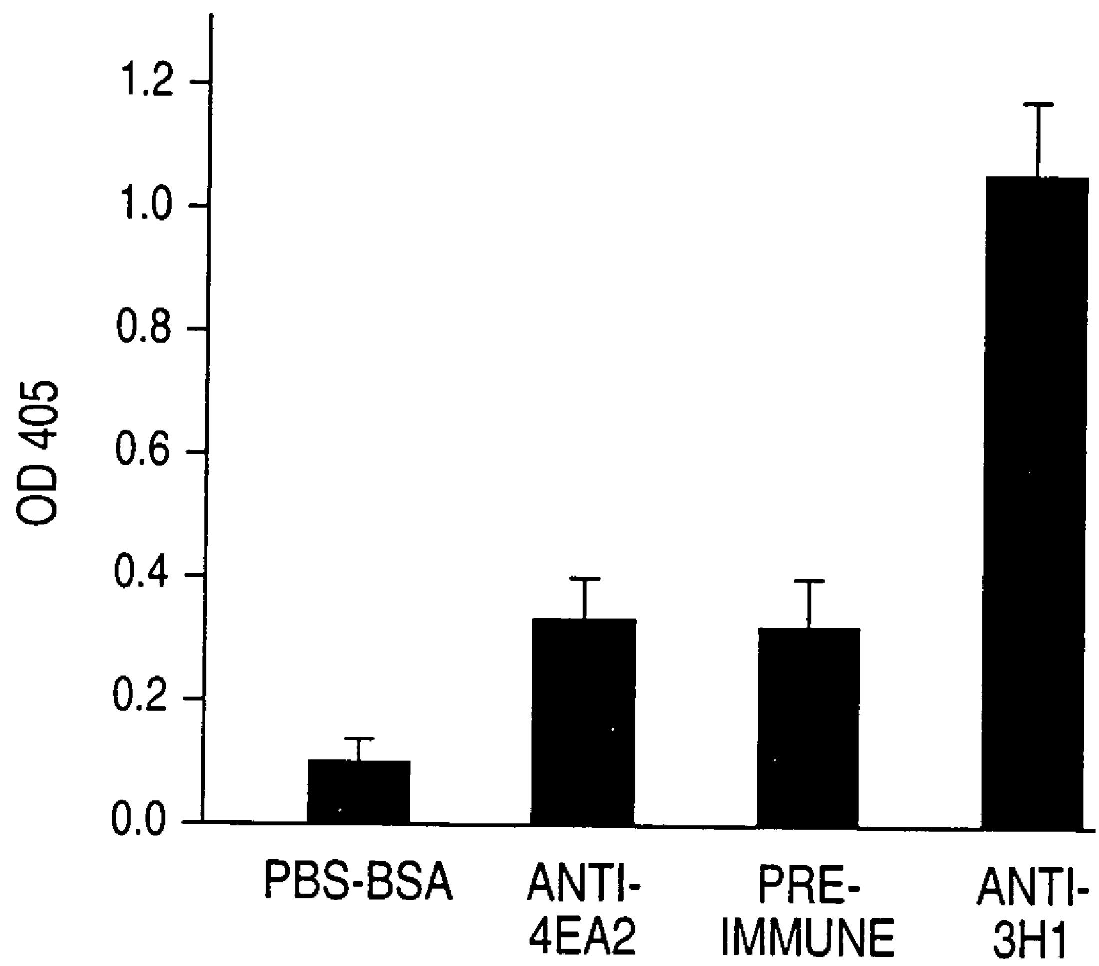
FIG. 9 is a bar graph depicting binding of sera from mice immunized with 3H1 to CEA. First bar, PBS-BSA; second bar, anti-4EA2; third bar, pre-immune sera; fourth bar, sera from mice immunized with $_3$H1.

As shown in FIG. 9, Ab3 present in the sera of mice immunized with 3H1 was specific for insolubilized CEA. All immunized mice (six in two groups) developed anti-CEA antibody as measured by ELISA. Control sera from preimmune mice or mice immunized with an unrelated Ab2-KLH (4EA2) did not show binding to pure CEA. In a parallel experiment, the binding of the same antisera was compared on a plate coated with unrelated ovarian tumor glycoprotein. The maximum binding obtained in each case was between 0.3 to 0.4 OD, the same as obtained with PBS-BSA control.

Figure 10A:
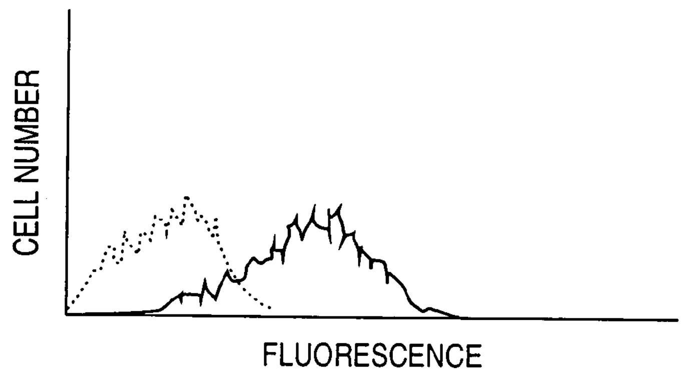
FIGS. 10A–D depict the result of FACS analysis of LS174-T cells reacted with 8019 (FIG. 10A); sera from mice immunized with 3H1 (FIG. 10B); pre-immune sera (FIG. 10C). Sera from 3H1-immunized mice showed distinct binding (FIG. 10B) that was similar to the binding pattern obtained with 8019 (Ab1) (FIG. 10A). No significant binding was obtained with human B cell lymphoma cells which do not express CEA (FIG. 10D).
Figure 10B:
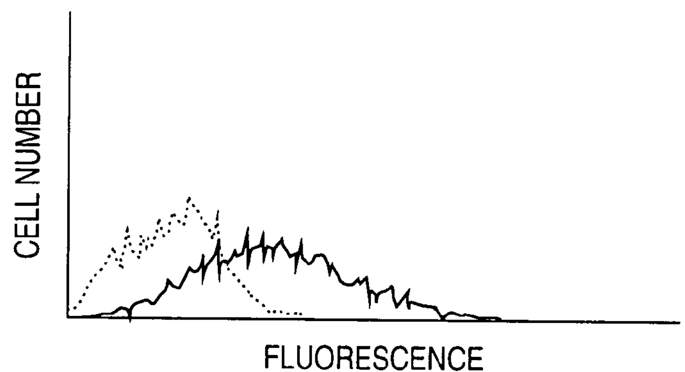
Figure 10C:
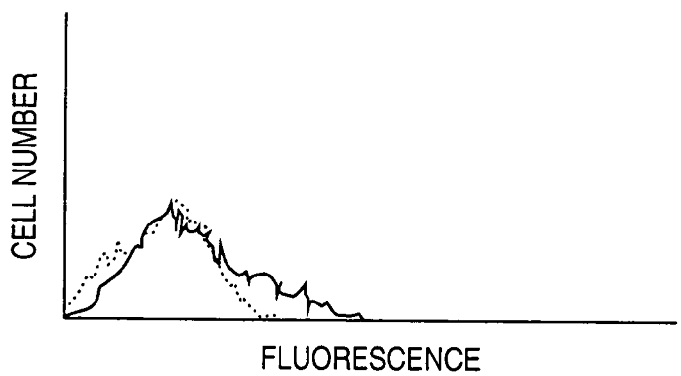
Figure 10D:
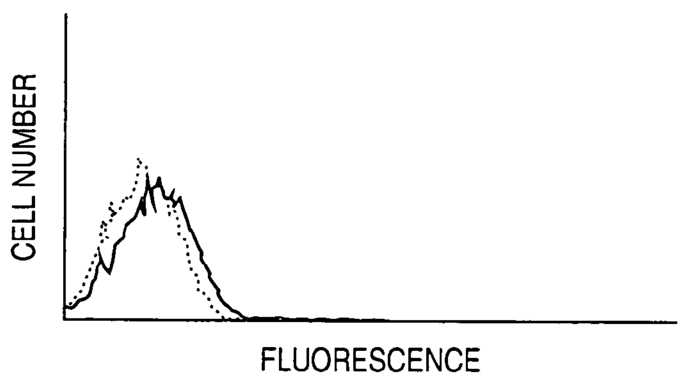

In a related experiment, the binding of Ab3 to cultured human colon carcinoma LS 174-T cells were tested in an indirect immunofluorescence assay and flow cytometry. As shown in FIG. 10, Ab3 containing sera from 3H1-immunized mice showed distinct binding (B) that was similar to the binding pattern obtained with 8019 (Ab1) (A). No significant binding was obtained with human B cell lymphoma cells which do not express CEA (FIG. 10D).

Confirmation that the Ab3 Elicited by 3H1 Had the Desired Specificity

Since the therapeutic objective of 3H1 lies in its ability to elicit a response reactive against the tumor associated antigen, the specificity of the Ab3 obtained was confirmed in a number of subsequent experiments.

The rabbit and mouse Ab3 antisera were depleted of anti-isotype and anti-allotype activity for use in the specificity experiments by passing over an adsorbant made by coupling immunoglobulin fractions of BALB/c mouse serum coupled to 4B. Adsorption was repeated until no anti-isotype or anti-allotype activity could be detected by immunodiffusion. Adsorbed Ab3 containing sera were diluted with PBS containing 1% BSA, 0.05% Tween 20 and used in specificity determination without any further purification.

Spleen cells from mice immunized with 3H1 were used to generate monoclonal Ab3 producing cell lines, using similar hybridoma technology as described earlier.

Inhibition assays: To determine whether Ab3 sera compete with Ab1 for binding to human colon carcinoma cells, the binding of radioiodinated 8019 to confluent monolayers of LS174-T cells was tested for inhibition in the presence of different Ab3 sera and Ab 1.

For direct binding assay between Ab1 and 3H1, purified 3H1 was used to coat plates (155 ng/well), and the binding of radiolabeled 8019 to 3H1 was tested in the presence of different Ab3 and Ab1. Percent inhibition of the assays were calculated according to the formula described above.

Sera from syngeneic mice immunized with 3H1, at 1/10 dilution, inhibited binding or iodinated 3H1 (Ab2) to Ab1 by 90%. No inhibition by preimmune sera or sera from mice immunized with unrelated Ab2, 4EA2-KLH was observed. Although stearic hindrance by Ab3 binding cannot be excluded in these assays, the results suggest the presence of Ab3 antibodies that share idiotopes with Ab1 (8019). The antisera from rabbits 729 and 730, immunized with 3H1, at 1/10 dilution, inhibited binding or iodinated 8019 to Ab2 by 88 and 57%, respectively. No significant inhibition was obtained with preimmune rabbit sera.

Figure 11:
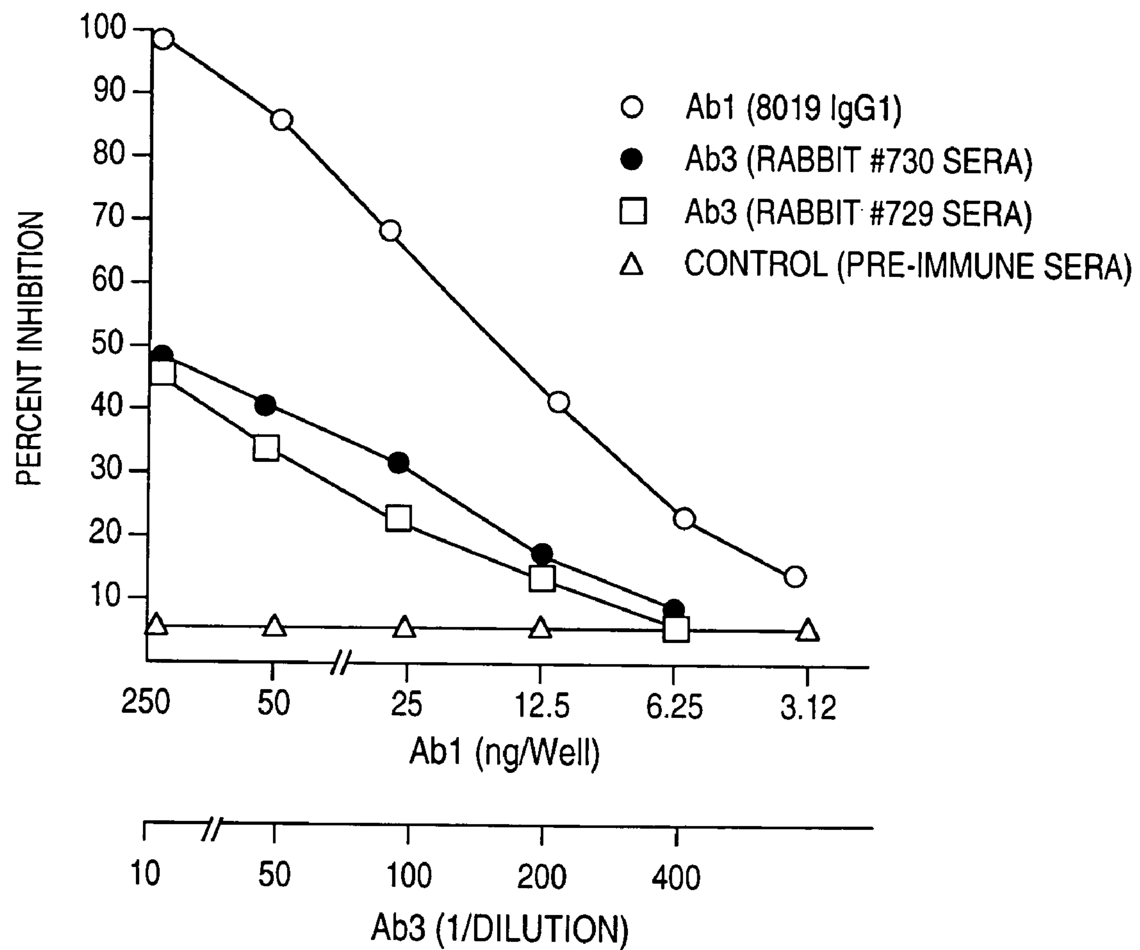
FIG. 11 is a graph depicting inhibition of 8019 binding to LS 174-T cells by sera from rabbits immunized with 3H1. Open circles denote 8019 (Ab1); closed circles denote serum from rabbit #730; open squares denote serum from rabbit #729; open triangles denote pre-immune sera.

If Ab3 has a similar binding site as Ab1, it should compete with Ab1 for binding to CEA as expressed by the human carcinoma cell line LS174-T. A fixed amount of radiolabeled 8019 was coincubated with different dilutions of rabbit Ab3 sera or Ab1 preparation and LS174-T cells (FIG. 11). Twenty ng of purified 8019-IgG1 (Ab1) inhibited binding by 50%, whereas the rabbit sera to 1/10 dilution produced 47 and 49% inhibition respectively for rabbit 729 and 730. This indicated that polyclonal rabbit Ab3 sera bind to the same Ag as Ab1 and therefore contain some antibody molecules with Ab1 properties.

Western blot analysis: The semipurified CEA extract was separated by standards SDS-PAGE in 7.5% gel under non-reducing conditions without β-mercaptoethanol. After electrophoresis the gel was transblotted to nitrocellulose filters according to the procedures to Towbin et al. ((1979) *Proc. Natl. Acad. Sci. USA* 76:4350). The filter strips were blocked with PBS-1% BSA and then incubated separately with 8019, polyclonal rabbit Ab3 sera, control rabbit Ab3 sera against unrelated Ab2, as well as monoclonal Ab3 culture supernatant. After incubation, the filter strips were washed with PBS and incubated with goat anti-mouse Ig or goat anti-rabbit Ig-alkaline phosphatase labeled reagents. The filter strips were again washed and the reaction was developed with the reagents BCIP and NBT supplied for an immunoblot kit (Bio-Rad Laboratories, Richmond, Calif.).

Figure 12:
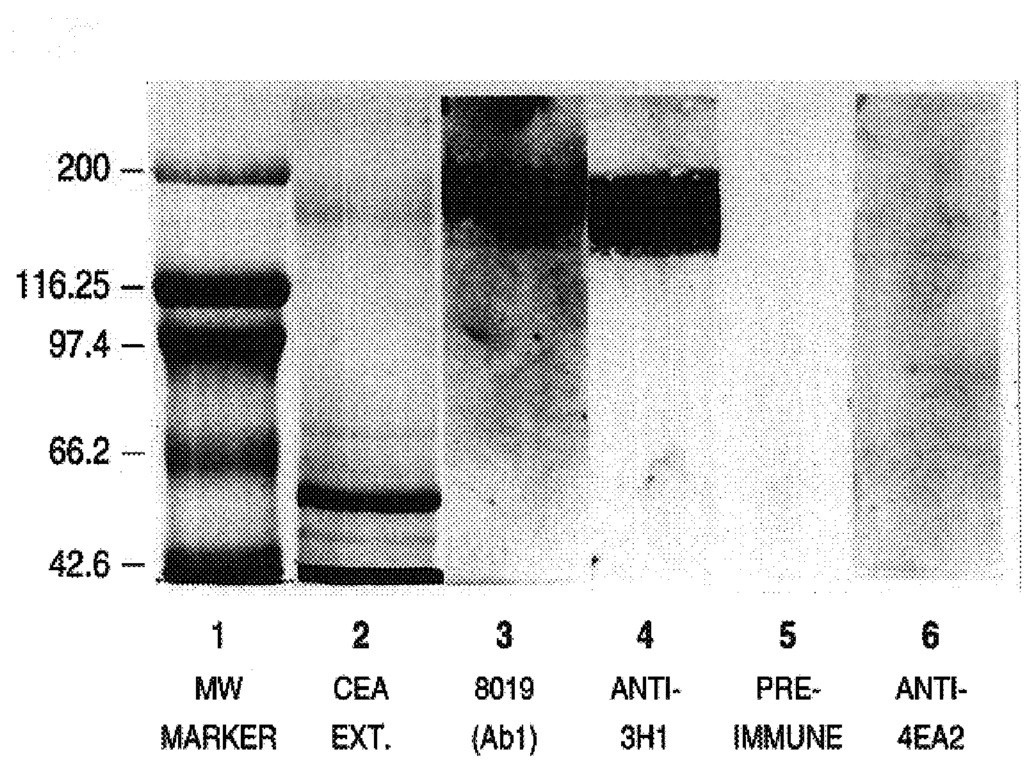
FIG. 12 is a half-tone reproduction of an immunoblot showing binding of Ab3 in rabbit sera to CEA. All reactions were with semi-purified extract of CEA separated by SDS-PAGE. Lane 1, molecular weight markers; lane 2, CEA extract stained with Buffalo black; lane 3, 8019; lane 4, rabbit sera (after immunization with 3H1); lane 5, pre-immune rabbit sera; lane 6, control sera from rabbits immunized with unrelated anti-Id 4EA2.

It has been shown that mAb 8019 specifically immunoprecipitates the 180,000 m.w. CEA by SDS-PAGE analysis (Mitchell (1980) *Cancer Immunol. Immunother.* 10: 1). To confirm that the Ab3 induced by 3H1 was specific for the CEA molecule, semipurified extract of CEA was separated by SDS-PAGE and transblotted to nitrocellulose filters. One filter strip (FIG. 12, lane 2) was stained with buffalo black. There were two overlapping bands at the 180,000 m.w. region (CEA) and one major band at the 50,000 m.w. region (normal cross-reacting Ag) and a few minor low m.w. bands. The remaining filter strips were then incubated with mAb 8019, rabbit Ab3 sera, and rabbit sera immunized with the unrelated isotype-matched Ab2β 4EA2 (a negative control). The reaction was developed by the ELISA assay as described above. Antibody 8019 (FIG. 12, lane 3) and rabbit Ab3 (lane 4) immunoprecipitated only molecules with a molecular mass of 180,000 Da from this complex mixture. The materials that were not precipitated by mAb 8019 or rabbit Ab3 sera contained a wide range of lower m.w. CEA-related Ag. There was no reactivity with preimmune (FIG. 12, lane 5) or control sera (lane 6). The Western blotting analysis confirmed the specificity of mAB 8019 and the reactivity of rabbit Ab3 with 180,000 m.w. CEA.

Figure 13:
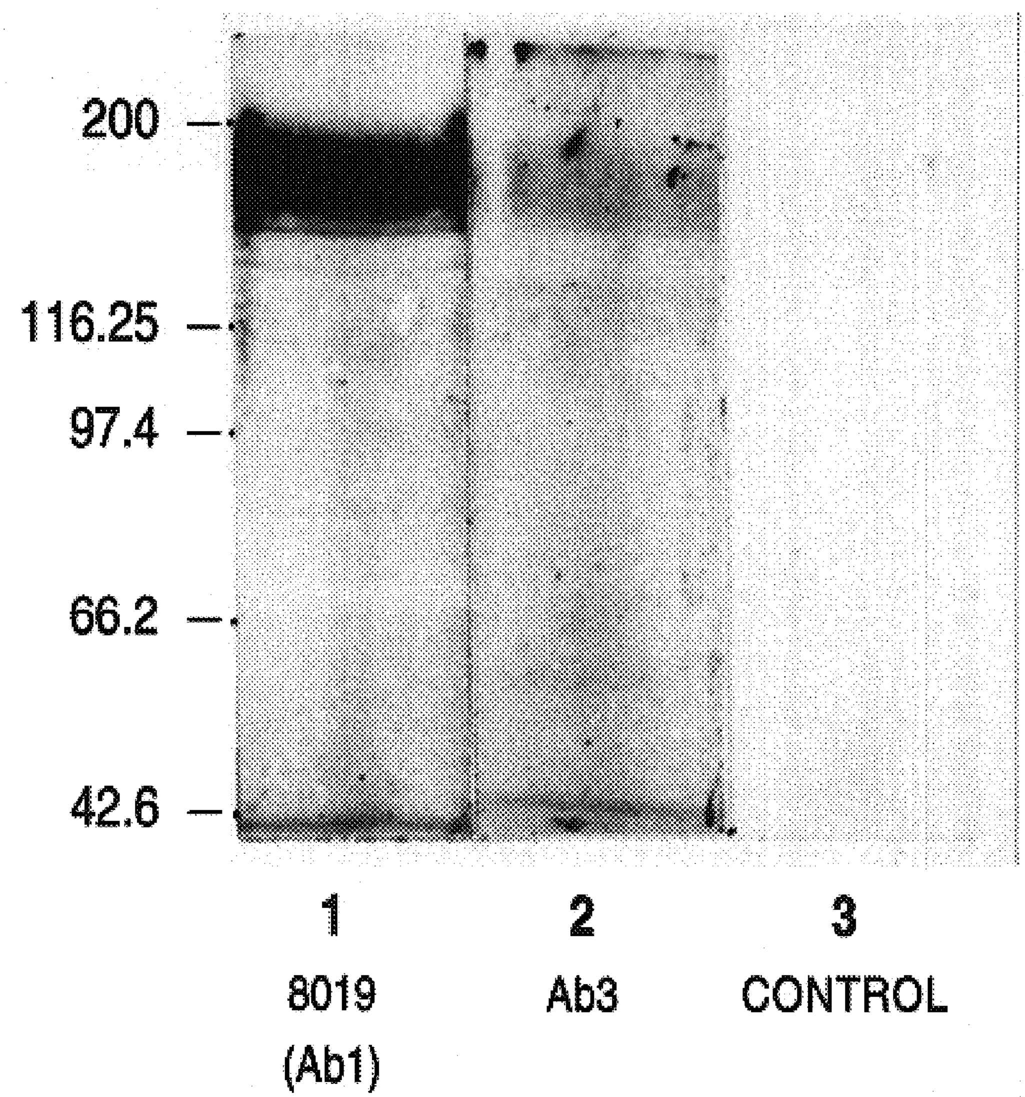
FIG. 13 is a half-tone reproduction of an immunoblot showing binding of Ab3 in mouse sera to CEA. Lane 1, 8019 (Ab1); lane 2, monoclonal mouse Ab3; lane 3, control.

FIG. 13 is a similar experiment conducted with mouse sera. The Ab3 elicited in mice immunized with 3H1 identified the same 180,000 m.w. form of CEA in the Western blot.

Immunoperoxidase staining of tissue sections with Ab1 and Ab3: The reactivities of monoclonal Ab1 and Ab3 (both polyclonal and monoclonal) were compared on surgical specimens of normal colon and colonic adenocarcinomas by a very sensitive staining method (biotin-streptavidin reagents, Vector, Burlingame, Calif.) as described in detail by Viale et al. ((1989) *J. Immunol.* 143:4338). All sections were counterstained with Meyer's hematoxylin. Pertinent specificity tests were performed, including block of the endogenous peroxidase, omission of the first layer, or substitution of nonimmune homologous serum for the specific antiserum and P3-653 myeloma culture supernatant for the Ab3 culture supernatant.

Figure 14:
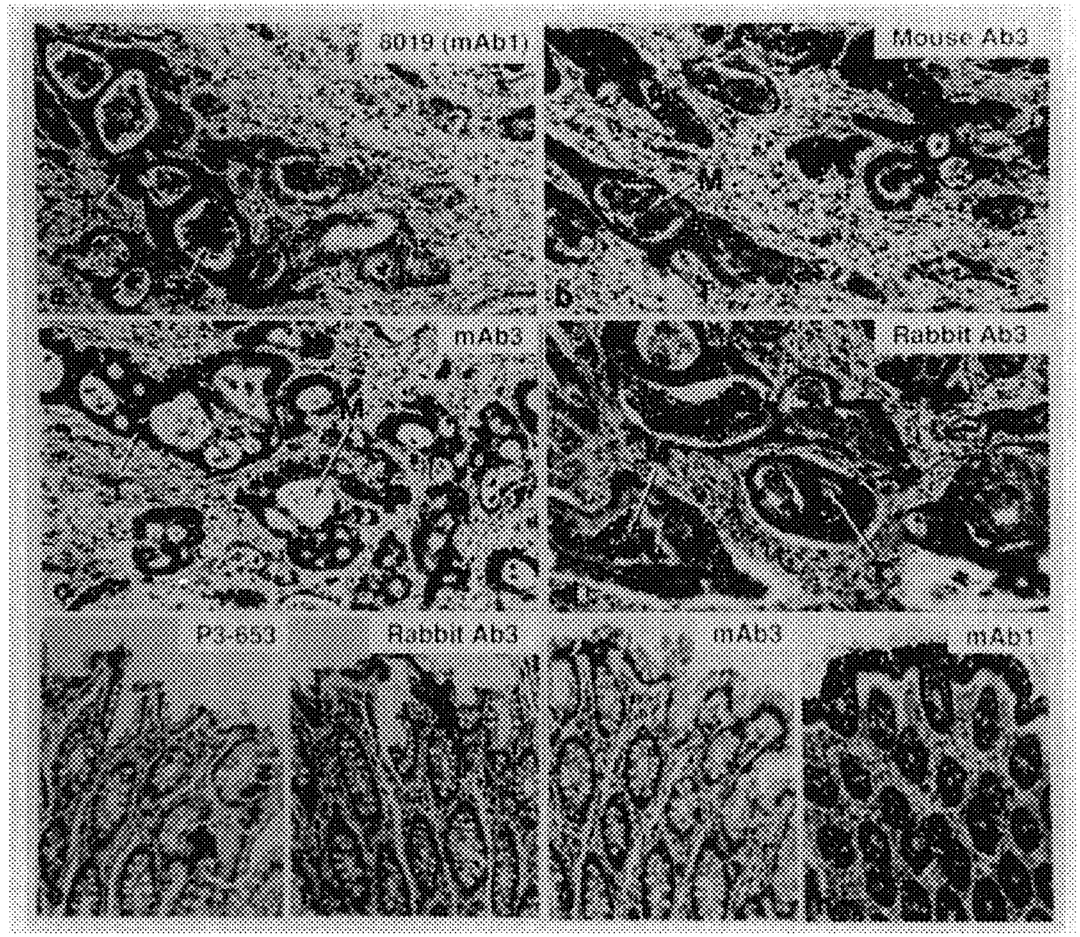
FIG. 14 is a half-tone reproduction depicting immunostained (immunoperoxidase) normal and cancerous tissue sections with Ab3. The pattern of reactivity of Ab3 on both normal and malignant colonic tissues was almost identical to that obtained with Ab1.
Figure 15:
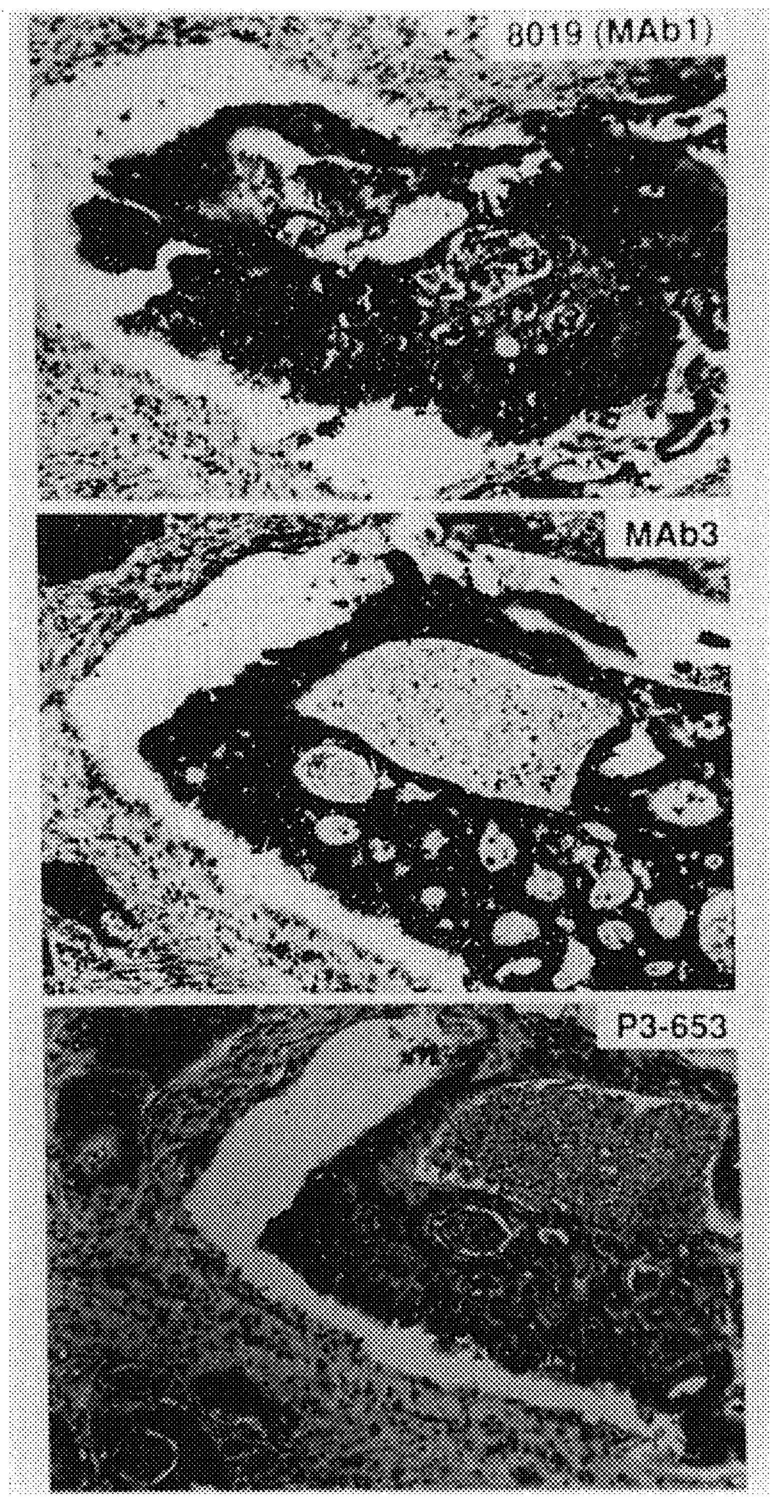
FIG. 15 is a half-tone reproduction depicting immunostained (immunoperoxidase) normal and cancerous tissue sections with Ab3. Reaction with 8019 (Ab1) resulted in the staining of tumor cells as well as secreted mucinous materials whereas reaction with mAb Ab3 resulted in the staining of tumor cells with no staining of secreted mucin.
Figure 16:
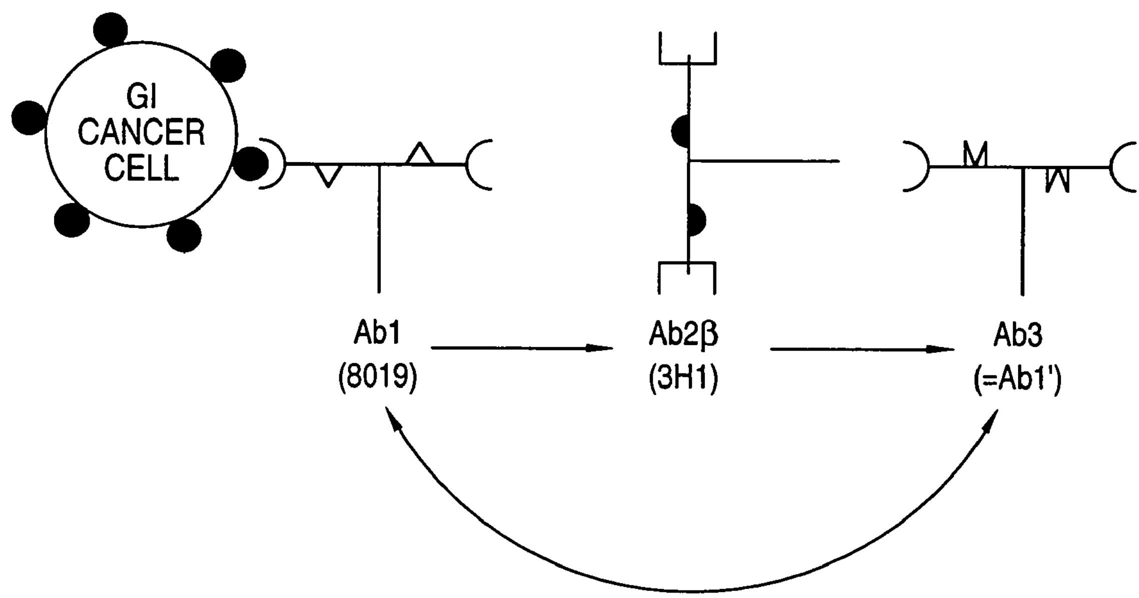
FIG. 16 is a schematic of the idiotype network for human gastrointestinal carcinoma.

The reactivity of 8019 were compared with that of Ab3 (both polyclonal and monoclonal) on normal colon and colonic tumor specimens. The pattern of reactivity of Ab3 on both normal and malignant colonic tissues was almost identical to that obtained with Ab1 (FIG. 14). There was no reaction with normal colonic mucosa, but 8019 and all the Ab3 reacted intensely with colonic tumors. The staining was apical in gland-like structures and granular (cytoplasmic) in less differentiated areas. There were subtle differences between the staining patterns obtained with 8019 (an IgG1, κ) and the monoclonal Ab3 (an IgM, κ). Reaction with 8019 resulted in the staining of tumor cells as well as secreted mucinous materials, whereas reaction with monoclonal Ab3 resulted in the staining of tumor cells with no staining of secreted mucin. (FIG. 15).

Tests of cellular immunity: Additional experiments may also be conducted to demonstrate that the animals immunized with 3H1 also have a CEA-directed cellular immune response. Spleen cells from mice immunized with 3H1 may be used in a T-cell proliferation assay. The spleen cells are cultured for 5 days in the presence of semipurified CEA, and then pulsed with [$^3$H]thymidine. Greater uptake in cells from 3H1 immunized animals than with controls is consistent with the presence of an idiotype-specific cellular immune response. Immunized rabbits may also be tested for DTH skin reactions against semipurified preparations of CEA or purified CEA. T cell cytotoxicity assays may also be conducted, as described elsewhere in this disclosure.

Example 2

Cloning and Sequencing of 3H1 cDNA

Unless otherwise specified, all cloning techniques were essentially as described by Sambrook et al. (1989) and all reagents were used according to the manufacturer's directions.

cDNA Cloning and Sequence Determination of the Variable Regions of 3H1

To sequence the $V_H$ region, total RNA was isolated from $1\times10^7$ 3H1 hybridoma cells. Yield of total RNA was about 100 μg. mRNA was prepared by passage through two-cycles of chromatography of oligothymidylate-cellulose columns. The yield of mRNA was about 10 μg. First strand cDNA was synthesized using SuperScript Preamplification kit (GIBCO/BRL). The DNA fragment encoding the $V_H$ of 3H1 was then amplified by PCR using the 5'-primer GGGAATTCATGRAATGSASCTGGGTYWTYCTCTT (SEQ ID NO:35) and the 3'-primer CCCAAGCTTCCAGGGRCCARKGGATARACIGRTGG (SEQ ID NO:36) (I=inosine, R=A or G, Y=C or T, K=G or T, S=C or G, W=A or T) corresponding to sequences of the leader (signal peptide) region amino acids −20 to −13, and the gamma constant region amino acids 126 to 119. In addition, the 5'-III site provided an alternative cloning strategy (Novagen, Madison Wis.). The fragment of cDNA amplified was subcloned into pT7 plasmid and NovaBlue competent cells were transformed using a protocol provided by the supplier (Novagen). Recombinant colonies were picked up by color selection and plasmid DNA was prepared by miniprep procedure. The DNA sequence of the double stranded plasmid was determined by Sequenase Version 2.0 kit (USB, Cleveland, Ohio). The sequence of the DNA insert in the plasmid was determined both orientations using T7 promoter primer (TAATACGACTCACTATAGGG) (SEQ ID NO:37) and U-19 primer (CTTTTCCCAGTCACGACGT)(SEQ ID NO:38). At least 8 clones were picked for sequence determination. The sequence of the 3H1 light chain was similarly determined. The forward primer for the light chain was 5'-ACTAGTCGACATGGTRTCCWCASCTCAGTTCCTTG (SEQ ID NO:39) and the reverse primer was 5'-CCCAAGCTTACTGGATGGTGGGAAGATGGA (SEQ ID NO:40), corresponding to −20 to −12 amino acids of the leader sequence and 122 to 116 of the constant region of the mouse kappa chain.

In order to minimize the error rates in PCR amplification, pfu DNA polymerase (Stratagene, San Diego) was used for amplification in all subsequent experiments. Mutant frequency with this thermostable DNA polymerase is 1/10 compared to Taq DNA polymerase.

Verification of the cDNA Clone by Amino Acid Sequence

Although 3 clones that we picked all had the same sequence, we felt it necessary to confirm that the isolated cDNA was indeed that of 3H1. Fifty μg of purified 3H1 antibody was diluted with sample loading buffer (50 mM Tris-HCl, pH 6.8, 1% SDS, 1% glycerol, 0.1% β-mercaptoethanol) and heated to 100° C. for 3 minutes. The denatured protein was loaded onto a 7.5% polyacrylamide gel (BioRad Miniprotean II Dual Slab Cell) containing SDS and subjected to electrophoresis at 200 V for 1 hour. Proteins in the gels were transferred to polyvinylidene difluoride (PVDF) membranes by the procedure described by Towbin et al. ((1979) *Proc. Natl. Acad. Sci. USA.* 78: 4350–4354) at 150 mA overnight. The transfer buffer contained 25 mM Tris, 192 mM glycine, 20% (v/v) methanol. The membranes were stained by quick dipping in 0.1% Coomasie Brilliant blue in 50% methanol-50% acetic acid, followed by washing in a solution containing 40% methanol plus 10% acetic acid. After drying the membrane at room temperature, the stained heavy and light chain bands were excised with a clean razor blade. The proteins on the membrane slices were subjected to N-terminal microsequencing by automated Edman degradation using an Applied Biosystem Model 477A protein sequencer employing pulsed-liquid chemistry and on-line phenyl-ethiohydantion amino acid identification. Each protein was subjected to 10–15 degradative cycles and the converted cleavage products from each cycle were analyzed by reverse-phase HPLC. The sequencing was done by Macromolecular Structural Facility of the University of Kentucky. The sequence of the was (Glu) ValGnLeuGlnGlnSerGlyProGluLeuValLysroGly (SEQ ID NO:41). Except for the first Glu whose identity was uncertain, 14 amino acid residues of the peptide matched exactly with the amino acids 2–15 of 3H1 heavy chain. This confirmed that the cDNA clone picked was that of the 3H1 heavy chain.

cDNA and derived amino acid sequence of the light chain variable region of 3H1 is shown in FIG. 1 (SEQ ID NO:1 and SEQ ID NO:2). The cDNA and derived amino acid sequence of the heavy chain variable region of 3H1 is shown in FIG. 2 (SEQ ID NO:3 and SEQ ID NO:4).

Example 3

T Cell Proliferation by a Polypeptide Fragment of 3H1

To examine the potential of polypeptide fragments of 3H1 to act as T cell epitopes (as measured by T cell proliferation), a polypeptide sharing homology with CEA (LCD-2, containing the CDR-2 from the light chain of 3H1 and having the sequence IYRANRLIDGV (SEQ ID NO: 11); amino acids 48–58) was synthesized using a 431A Peptide Synthesizer (Advanced Biotechnogies, Inc., Columbia, Md.). A T cell proliferation assay was performed using the peptide as a stimulant for splenocytes isolated from mice immunized with 3H1-KLH conjugate.

Cellular immune responses were measured by the proliferation of T cells in spleen incubated with LCD-2 and aluminum hydroxide precipitated isotope matched control anti-idiotype antibody 4DC6.

Splenic T lymphocytes were isolated from mice 7–10 days after a second booster and enriched by nylon wool column. The isolated T cells were incubated with irradiated, normal syngeneic spleenocytes which act as antigen-presenting cells and $5\times10^6$ cells per well were incubated with different concentrations of 3H1-polypeptide (0.5 to 2.0 μg/ml, 50 μl per well including the 3H1 polypeptide, including polypeptide and control 4DC6-Alugel (10 μg to 2 μg) in RPMI medium with 5 percent heat-inactivated fetal calf serum and penicillin and streptomycin. The non-specific mitogen phytohemagglutinin-P was used as a positive control at 2 μg and 1 μg per well. After the cells were incubated for five days at 37° C. in an atmosphere containing 5 percent carbon dioxide, they were pulsed with $^3$H-thymidine (1 μCi per well) for 20 hours. $^3$H-thymidine incorporation was measured in pre and post-therapy samples. Data were expressed as mean counts (triplicate wells) per minute of $^3$H-thymidine incorporation. The Standard Deviation of the data was <10% for each determination. Stimulation of T cell proliferation in response to the 3H1 polypeptide LCD-2 was observed in comparison to the control.

Figure 17:
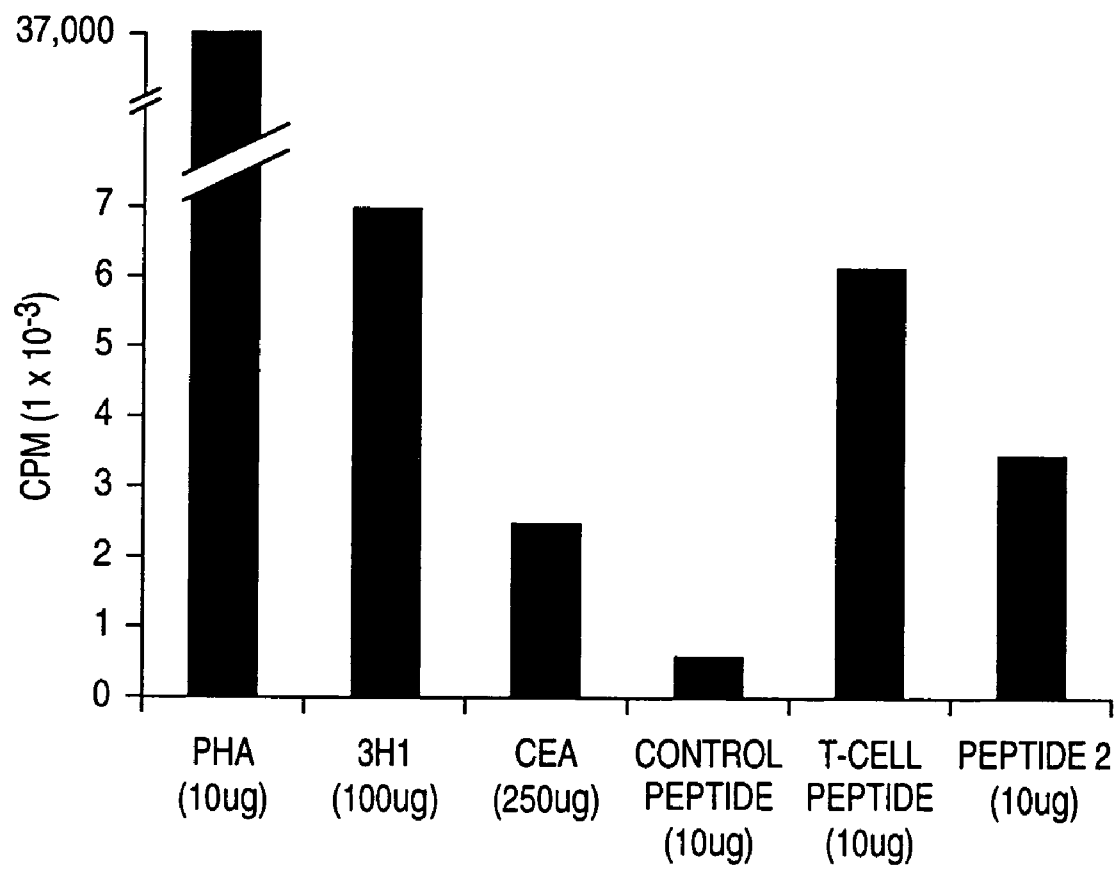
FIG. 17 is a bar graph depicting T-cell proliferation assays from one patient for 3H1 polypeptide LCD-2 (IYRANRLIDGV) (SEQ ID NO:11). For each bar indicates T-cell proliferation in the presence of phytohemagglutinin (first bar); intact 3H1 (second bar); purified CEA (third bar); control peptide (fourth bar); T cell peptide derived from CEA (fifth bar); and 3H1 polypeptide LCD-2 (sixth bar).

We then tested the ability of this polypeptide to stimulate T cells from patients with advanced colorectal cancer before and after administration with alum-precipitated 3H 1. Peripheral blood mononuclear cells (PBMC) from 5 colorectal cancer patients were obtained by standard Ficoll-Hypaque density gradient centrifugation and used for the T cell proliferation assay described above. The results for one patient are shown in FIG. 17. No stimulation of T cell proliferation was observed in these patients before therapy. PBMC from 2 of the 5 patients were stimulated by these peptides multiple times during the course of therapy with 3H 1.

These results suggest the possibility of using polypeptide fragments of 3H1 for stimulation of T cells for therapeutic vaccination of CEA positive colorectal cancer patients.

Example 4

Figure 18:
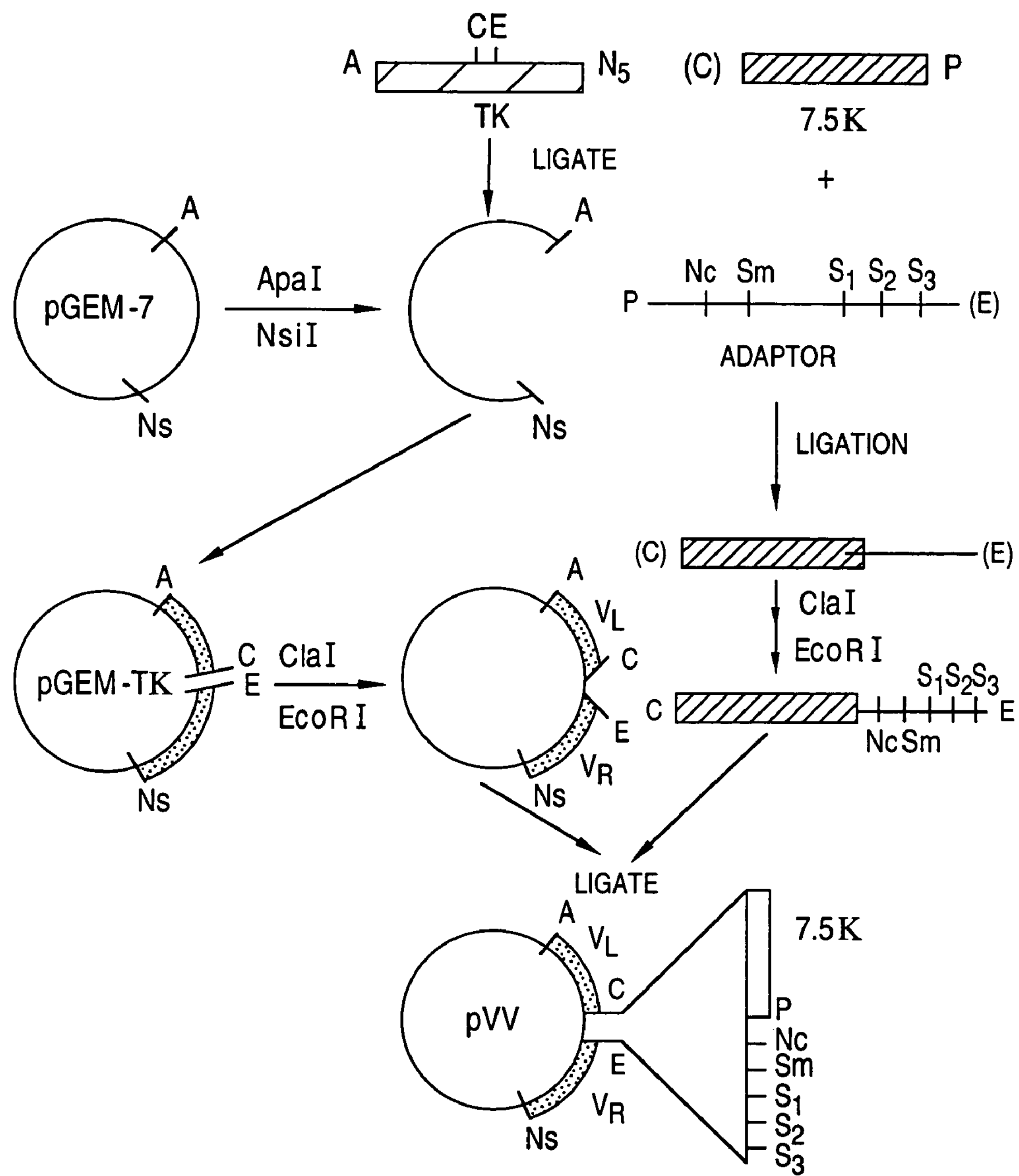
FIG. 18 depicts the scheme for construction of pVV, a generic vaccinia vector (plasmid) for expression of 3H1 polynucleotides. The darkened box denotes vaccinia TK gene; the hatched box denotes the 7.5 K vaccinia promoter. Restriction sites are: A, Apa I; Ns, Nsi I; C, Cla I; E, Eco RI; P, Pst I; Nc, Nco I; Sm, Sma I. (E) and (C) denote potential EcoRI and ClaI sites, respectively. Three stop codons are indicated by S1, S2 and S3. $V_L$ and $V_R$ represent left and right vaccinia flanking sequences. TK and 7.5 K were obtained by PCR using DNA from wild type WR strain of vaccinia.

Construction of a Recombinant Vaccinia Vector Encoding a 3H1 Polypeptide Fragment Plasmid Construction and Production of Recombinant Vaccinia Viruses The scheme for construction of a general vaccinia vector (rvv) is shown in FIG. 18. We retrieved the complete sequence of TK gene of the wild type WR strain of vaccinia virus (GenBank, accession number J02425) from the National Center for Biotechnology Information (NCBI) by the BLAST program. Aitschul et al. (1990) *J. Mol. Biol.* 215:403–410. From the sequence data, forward and reverse PCR primers 5'-CAGATGGAAGGGCCCAAC (SEQ ID NO:42) and 5'-GATTGATGCATATCATTACC (SEQ ID NO:43) were synthesized, corresponding to nucleotides 22–39 and 727–708 respectively of the TK sequence Hruby et al (1983) *Pro. Natl. Acad. Sci. USA* 80:3411–3415. An Apa I site (underlined) was introduced into the forward primer and a Nsi I site (underlined) in the reverse primer for insertion into the plasmid pGEM-7Zf(+) (Promega). DNA from the wild type WR strain of vaccinia was isolated and TK gene was amplified by PCR. A DNA fragment of expected size (about 700 bp) was obtained by PCR. This DNA was separated by electrophoresis in low melting point agarose and purified by digestion with GELase (Epicentre Tech.). The TK DNA fragment was ligated to the pGEM-7Zf (+) after digestion with Apa I plus Nsi I. The resulting plasmid (pGEM-TK) was amplified by standard transformation techniques. Insertion was verified by restriction mapping.

Promoter 7.5 K was amplified from wild type vaccinia virus by PCR using the forward primer 5'-GTTATCGATGTCGAATAGCC (SEQ ID NO:44) and the reverse primer 5'-TTGCTGCATTGAGTACTGTTCT (SEQ ID NO:45) corresponding to nucleotides 69–88 and 335–312 of the 7.5 K promoter sequence. Cochran et al. (1985) *J. Virol.* 54:30–37. A Cla I site (forward) and a Pst I site (reverse) were included in the primers. The amplified DNA fragment was digested with Pst I. A polynucleotide adapter was synthesized with the smaller oligonucleotide being phosphorylated at the 5'-end by polynucleotide kinase. The hemi-phosphorylated adapter was ligated to Pst I digested PCR amplified 7.5 K promoter DNA fragment. The product was digested with Cla I/EcoR I digested pGEM-TK.

A cDNA insert encoding a 3H1 polypeptide is inserted between the Nco I and XmaI (SmaI) sites of pVV. This plasmid also contains the leader sequence of the $V_H$ at the 5' end of the scFv cDNA. If desired, a vaccinia control plasmid can be constructed containing cDNA for *E. coli* β-galactosidase.

Construction of Rvv

Rvvs are constructed by homologous recombination of vaccinia plasmids and wild-type WR strain of vaccinia virus according to the procedure of Mackett et al. (DNA Cloning, Vol. II, D. M. Glover, ed., IRL Press 1985) using CV-1 cells. Recombinant viral clones expressing β-galactosidase (controls) are selected by growth on $TK^-$ 143B cells in the presence of 5'-bromodeoxyuridine and 5-bromo-4-chloro-3-indoyl-β-D-galactosidase (X-Gal). Blue recombinant viruses are picked by pasteur pipettes and plaque purified. As a second step in clone selection, Southern blot of extracted DNA is performed, using 3H1 cDNA as the probe. Further selection of rvv is made by assay of culture supernatant of the virally infected CV-1 or any other eukaryotic cells by ELISA. If cell-associated 3H1 polypeptide is in the rvv (i.e., if the leader sequence is deleted), cell lysate is assayed. Western blotting with 8019 (Ab1) as probe is also performed. Biological activity of the 3H1 polypeptide synthesized by the vaccinia virus is determined by cell binding inhibition assay, as described above. Rvv clones containing 3H1 polynucleotides are selected by staining with 0.1% neutral red and plaque purified as above. Viral clones are grown into a high-titer lysate using standard techniques. Mackett et al (1982) *Proc. Natl. Acad. Sci. USA* 79:7415–7419. Typically a clone producing the highest amount of 3H1 polypeptide is selected for further studies.

Assay of 3H1 Polypeptides (Foreign Proteins) Expressed By Recombinant Vaccinia Virus CV-1 cells are propagated in Dulbecco's modified Eagle's medium (DMEM) supplemented with 10% fetal calf serum and 100 units of penicillin and 100 μg of streptomycin per ml in 25-$cm^2$ flasks or 6-well Cluster flasks. Cells are inoculated with rvv at a MOI of 30. The virus is allowed to absorb for 2 hours at 37° C. in a tissue culture incubator, following which the inoculum is replaced with the culture medium and the incubation was continued. Supernatant is removed after incubation for indicated time and the 3H1 polypeptide secreted is assayed. As a control, supernatant from mock infected cells is used. Assay of 3H1 polypeptides can be performed by testing for binding to 8019 (Ab1), for example as described in Examples 1 and 5. β-D-galactopyranoside produced by rvv-lacZ is assayed according to Miller (Experiments in Molecular Genetics, Cold Spring Harbor Pines 1972) with p-nitro-β-D-galactopyranoside as the substrate. Culture supernatant from virus infected cells is treated with β-propionate to inactivate the virus before assay Corcoran et al. (1988) *J. Parasit.* 74:763. Incorporation of $^3$H-thymidine by NFS60 cells used as a measure of cell proliferation Jaffee et al. (1993) *Cancer Res.* 53:2221–2226. Radioactivity due to $^3$H-thymidine incorporation in the presence of supernatant from mock infected CV-1 cells is subtracted as background. As positive control and for standard of biological activity, intact 3H1 is used. Alternatively, standard solutions of GM-CSF can be used as described in Qin et al. (1996) *Gene Therapy.*

Testing Vaccinia 3H1 Vaccines

For administration of vaccinia, a virus titer of 104 to $10^7$ pfu is injected in a mouse. Injections can be subcutaneous, intramuscular, intradermal or interperitoneal. Immunizations are performed weekly. Mice are bled 7 days after every immunization for determination of Ab3 (including Ab1'). Testing for development of T cell immunity is performed 10 days after the booster immunization. Mice can also be tested by tumor challenge, in which survival after injection with tumor cells is monitored.

For administration of vaccinia via virally infected tumor cells, autologous tumor cells are maintained in Eagles medium containing 10% (vol/vol) fetal calf serum, 2 mM glutamine and gentamicin. A monolayer of confluent cells in a 75-cm2 flask is inoculated with ($3\times10^8$) plaque forming units (pfu) of rvv. After 2 hours at 37° C., the inoculum is replaced by DMEM and the incubation was continued for another 24 hours. After examination under microscope, cells are collected by scraping and washed two times with PBS and resuspended in PBS at a desired concentration. ($10^3$ to $10^5$/200 μl). Female C57BL/6 mice, 6–8 weeks old are purchased from Harlan Bioproducts for Science Inc., (IN). Animals are injected subcutaneously with the cellular vaccine in the rear left flank and two weeks later tumor cells are injected at the rear right flank for challenge. Survival of mice following tumor challenge and the presence of tumor is monitored daily. If the tumor is measurable, tumors are measured weekly by a caliper in two dimensions and the volumes are calculated using the formula ($\text{width}^2\times\text{length}$)/2. Tumors which are palpable but too small for measuring the volume accurately are recorded as zero volume, but tumor incidence is recorded as positive. Tumor volumes are averaged only for those that actually develop tumors over the observation period of 120 days. Zero values are included for those mice that eventually develop tumors but were tumor-free at a given time point.

Statistical Evaluation

Statistical evaluation is done using SigmaStat software (Jandel, Inc. San Rafael, Calif., USA). A P value of <0.05 was considered to indicate statistical significance.

Example 5

Expression and Characterization of a 3H1 scFv

Based on our sequence data, we prepared a cDNA construct encoding $V_H$-$(GGGS)_3$-$V_L$ for 3H1. A cDNA for this 3H1 fragment was incorporated into the pET-22b(+) plasmid vector (Novagen, Madison, Wis.) and expressed in *E. coli*. Sequence analysis was performed to confirm the plasmid construct, which contained the carboxy end of $V_H$ linked to the framework of $V_L$ and did not contain the leader region pET-22b(+) contains a nickel ion binding domain consisting of 6 sequential histidine residues ($His_6$). The $His_6$ domain has a high affinity for nickel, which was used for the purification of the recombinant 3H1 scFv.

Figure 20:
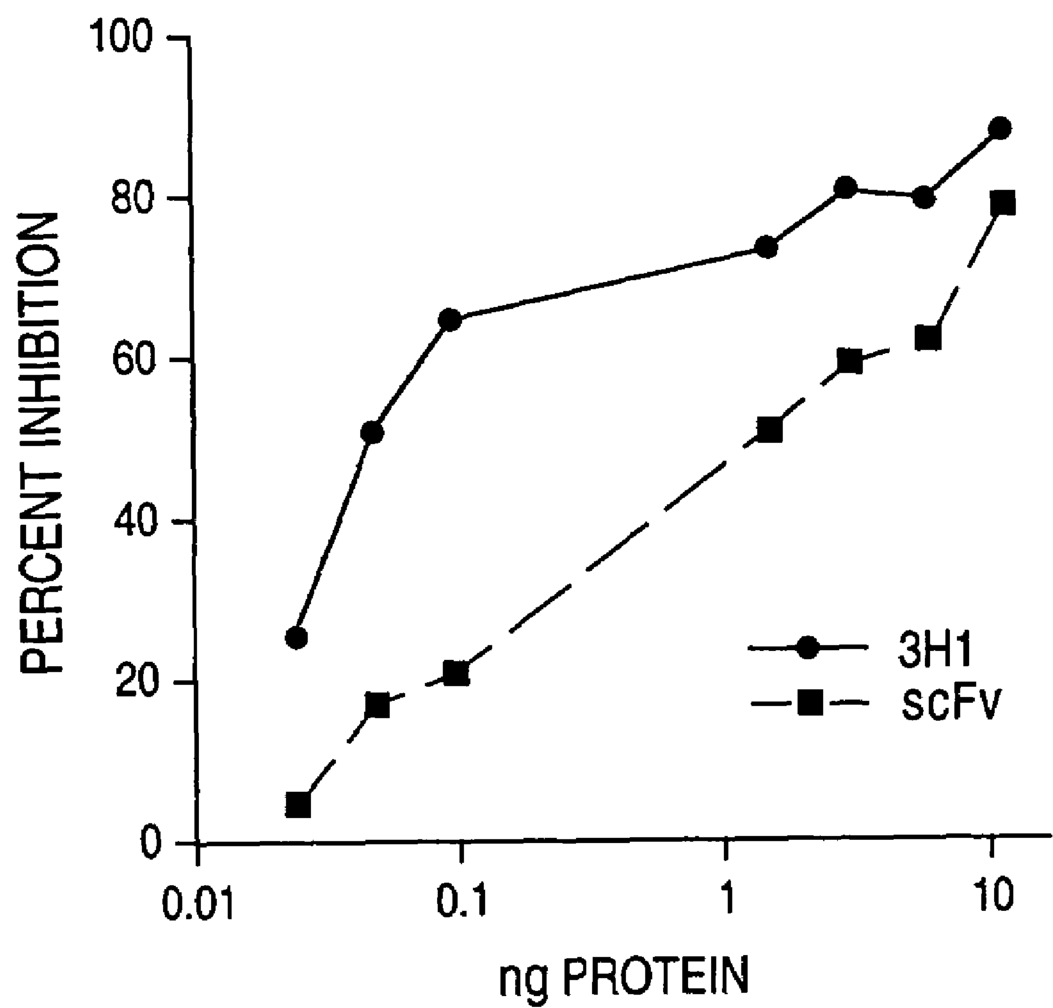
FIG. 20 is a graph comparing percent inhibition of binding of radiolabeled 8019 (Ab1) to CEA-positive LS174-T cells by a 3H1 scFv or intact 3H1. The experiment was performed using increasing amounts (in nanograms) of scFv (or intact 3H1). The squares connected by a dotted line denote 3H1 scFv; the circles connected by a solid line denote intact 3H1.

A cell binding competition assay was performed to investigate whether the 3H1 scFv retained the antigen mimicry shown by intact 3H 1. CEA-positive LS 174-T cells ($1\times10^5$ cells/well in 50 μl volume) were placed in a 96-well plate. The cells were incubated for 2 hours at room temperature with [$^{125}$I] 8019 (Ab1), 100,000 cpm, in the absence and presence of increasing concentrations of 3H1 or the 3H1 scFv fragment. Percent inhibition was calculated according to the following formula:

$$\%\ \text{inhibition} = 1 - \left(\frac{R_T - R_C}{R_{MAX} - R_C}\right)\times 100$$

Where $R_T$ is the average radioactivity of an experimental well, $R_{Max}$, is the radioactivity in the absence of any protein, and $R_C$ is the background radioactivity. Results of this experiment are shown in FIG. 20. The results suggest that a 3H1 scFv is capable of mimicking the antigen (CEA), although its ability to act as surrogate antigen is lower than intact 3H1. This lower mimicry is possibly due to incomplete renaturation of the protein. Modulation of expression in *E. coli* using a less active promoter, for instance, should improve the result. An unrelated anti-idiotype antibody (11D10) used as a control showed no inhibition.

Example 6

Testing Recombinant 3H1 Polynucleotide Vaccines in Mice

Recombinant candidate 3H1 polynucleotide vaccines are prepared as described herein. Two groups of 10–15 female C57BL/6 mice (6–8 weeks old) are immunized intramuscularly with doses of 50–100 μg purified plasmid which is coupled to KLH using glutaraldehyde as described by Bhattacharya-Chatterjee et al. (1988).

In addition, various routes of administration are compared, such as intramuscular, intradermal, subcutaneous and interperitoneal.

Mice are bled 7 days after every immunization for determination of Ab3 (including Ab1') production as described above. Three mice are sacrificed from each group for isolation of spleens for the T cell proliferation assay 10 days after a booster immunization.

To determine whether any observed effect is specific, as opposed to non-specific humoral or cellular immunity (by indirect mechanisms such as cytokine production induced by the injected polynucleotide), the following controls are used: (a) plasmid without 3H1 polynucleotide insert; (b) plasmid with 3H1 polynucleotide insert in the opposite (i.e., anti-sense) orientation; and (c) plasmid containing a polynucleotide encoding an unrelated Ab2.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

The invention claimed is:

1. An isolated antigen-binding fragment of antibody 3H1, comprising the sequence IYRANRLIDGV (SEQ ID NO:11), wherein said antigen-binding fragment comprises an immunoglobulin variable region containing the three light chain CDRs of antibody 3H1, and an immunoglobulin variable region containing the three heavy chain CDRs of antibody 3H1, and wherein antibody 3H1 is produced by the hybridoma deposited under ATCC Accession No: HB12003.

2. A composition comprising the antigen-binding fragment of claim 1 and a pharmaceutically acceptable excipient.

3. An isolated polypeptide comprising an immunoglobulin variable region containing the three light chain CDRs of antibody 3H1, and an immunoglobulin variable region containing the three heavy chain CDRs of antibody 3H1; wherein the light and heavy chain CDR amino acid sequences of antibody 3H1 are contained in SEQ ID NO:2 and SEQ ID NO:4, respectively; and wherein said polypeptide has the ability to bind to the idiotype of anti-CEA monoclonal antibody 8019 produced by the hybridoma deposited under ATCC Accession Number CRL-8019.

4. A fusion polypeptide comprising the antigenbinding fragment of claim 1 or the polypeptide of claim 3.

5. A polymeric 3H1 polypeptide comprising a plurality of polypeptides according to claims 1 or 3.

6. A kit comprising a polypeptide according to claim 1 or 3 in suitable packaging.

7. The kit of claim 6, wherein the polypeptide comprises a detectable label.

8. The polypeptide of claim 3, wherein the polypeptide has the ability to stimulate production of anti-CEA antibody.

9. A humanized antibody comprising the polypeptide of claim 3.

10. An isolated polypeptide according to claim 3, wherein the polypeptide comprises the sequence IYRANRLIDGV (SEQ ID NO:11).

11. A fusion polypeptide comprising an immunoglobulin variable region containing the three light chain CDRs of antibody 3H1 and an immunoglobulin variable region containing the three heavy chain CDRs of antibody 3H1, wherein the immunoglobulin variable regions are joined by a linker polypeptide of about 5 to 20 amino acids, wherein the light and heavy chain CDR amino acid sequences of antibody 3H1 are contained in SEQ ID NO:2 and SEQ ID NO:4, respectively, and wherein said polypeptide has the ability to bind to the idiotype of anti-CEA monoclonal antibody 8019 produced by the hybridoma deposited under ATCC Accession Number CRL-8019.

12. The fusion polypeptide of claim 11, comprising the light chain variable region of the amino acid sequence contained in SEQ ID NO:2 and the heavy chain variable region of the amino acid sequence contained in SEQ ID NO:4.

13. The fusion polypeptide of claim 4 or 11 further comprising granulocyte macrophage colony stimulating factor (GM-CSF) or interleukin 2 (IL-2).

14. The fusion polypeptide of claim 4 or 11 further comprising a heterologous immunoglobulin constant region.

15. The fusion polypeptide of claim 11, wherein the linker polypeptide comprises a sequence of about 15 amino acids consisting of glycine residues and serine residues.

16. The fusion polypeptide of claim 11, wherein the linker polypeptide comprises the amino acid sequence $(GGGGS)_3$ (SEQ ID NO: 49).

17. A method of detecting an antibody that binds to 3H1 in a sample comprising the steps of:

(a) contacting antibody from a sample obtained from an individual with the polypeptide of claim 3 under conditions that permit the formation of a stable antigen-antibody complex; and (b) detecting the stable complex formed in step (a), if any.

18. A composition comprising an isolated polypeptide and a pharmaceutically acceptable excipient, wherein said isolated polypeptide comprises an immunoglobulin variable region containing three light chain CDRs of antibody 3H1; and an immunoglobulin variable region containing three heavy chain CDRs of antibody 3H1; wherein the light and heavy chain CDR amino acid sequences of antibody 3H1 are contained in SEQ ID NO:2 and SEQ ID NO:4, respectively; and wherein said polypeptide has the ability to bind to the idiotype of anti-CEA monoclonal antibody 8019 produced by the hybridoma deposited under ATCC Accession Number CRL-8019.

19. The composition of claim 2 or 18, further comprising an adjuvant.

* * * * *

```
                         SEQUENCE LISTING

(1) GENERAL INFORMATION:

   (iii) NUMBER OF SEQUENCES: 76


(2) INFORMATION FOR SEQ ID NO: 1:

     (i) SEQUENCE CHARACTERISTICS:
          (A) LENGTH: 447 base pairs
          (B) TYPE: nucleic acid
          (C) STRANDEDNESS: single
          (D) TOPOLOGY: linear

    (ix) FEATURE:
          (A) NAME/KEY: CDS
          (B) LOCATION: 22..447

    (xi) SEQUENCE DESCRIPTION: SEQ ID NO: 1:

TCATATGGAT TACTAGTCGA C ATG GTA TCC ACA GCT CAG TTC CTT GGT ATC        51
                        Met Val Ser Thr Ala Gln Phe Leu Gly Ile
                          1               5                  10

TTG TTG CTC TGG TTT CCA GGT ATC AAA TCT GAC ATC AAG ATG ACC CAG        99
Leu Leu Leu Trp Phe Pro Gly Ile Lys Ser Asp Ile Lys Met Thr Gln
                 15                  20                  25

TCT CCA TCT TCC ATG TAT GCA TCT CTA GGA GAG AGA GTC ACG ATC ACT       147
Ser Pro Ser Ser Met Tyr Ala Ser Leu Gly Glu Arg Val Thr Ile Thr
             30                  35                  40

TGC AAG GCG AGT CAG GAC ATT AAT GGT TAT TTA AAT TGG TTC CAA CAA       195
Cys Lys Ala Ser Gln Asp Ile Asn Gly Tyr Leu Asn Trp Phe Gln Gln
         45                  50                  55

GAA CCA GGG AAA TCT CCT AAG ACC CTG ATC TAT CGT GCA AAT AGA TTG       243
Glu Pro Gly Lys Ser Pro Lys Thr Leu Ile Tyr Arg Ala Asn Arg Leu
     60                  65                  70

ATA GAT GGG GTC CCA TCA AGG TTC AGT GGC AGT GGA TCT GGG CAA GTT       291
Ile Asp Gly Val Pro Ser Arg Phe Ser Gly Ser Gly Ser Gly Gln Val
 75                  80                  85                  90

TAC TCT CTC ACC ATC AGC AGC CTG GAA TAT GAA GAT ATG GGA ACT TAT       339
Tyr Ser Leu Thr Ile Ser Ser Leu Glu Tyr Glu Asp Met Gly Thr Tyr
                 95                 100                 105

TAT TGT CTA CAG TTT GAT GAG TTT CCG TGG ATG TTC GGT GGA GGC ACC       387
Tyr Cys Leu Gln Phe Asp Glu Phe Pro Trp Met Phe Gly Gly Gly Thr
            110                 115                 120

AAG CTG GAA ATC AAA CGG GCT GAT GCT GCA CCA ACT GTC TCC ATC TTC       435
Lys Leu Glu Ile Lys Arg Ala Asp Ala Ala Pro Thr Val Ser Ile Phe
        125                 130                 135

CCA CCA TCC AGT                                                       447
Pro Pro Ser Ser
    140
```

(2) INFORMATION FOR SEQ ID NO: 2:

(i) SEQUENCE CHARACTERISTICS:
(A) LENGTH: 142 amino acids
(B) TYPE: amino acid
(D) TOPOLOGY: linear (ii) MOLECULE TYPE: protein (xi) SEQUENCE DESCRIPTION: SEQ ID NO: 2:

```
Met Val Ser Thr Ala Gln Phe Leu Gly Ile Leu Leu Leu Trp Phe Pro
  1               5                  10                  15

Gly Ile Lys Ser Asp Ile Lys Met Thr Gln Ser Pro Ser Ser Met Tyr
             20                  25                  30

Ala Ser Leu Gly Glu Arg Val Thr Ile Thr Cys Lys Ala Ser Gln Asp
         35                  40                  45

Ile Asn Gly Tyr Leu Asn Trp Phe Gln Gln Glu Pro Gly Lys Ser Pro
     50                  55                  60

Lys Thr Leu Ile Tyr Arg Ala Asn Arg Leu Ile Asp Gly Val Pro Ser
 65                  70                  75                  80

Arg Phe Ser Gly Ser Gly Ser Gly Gln Val Tyr Ser Leu Thr Ile Ser
                 85                  90                  95

Ser Leu Glu Tyr Glu Asp Met Gly Thr Tyr Tyr Cys Leu Gln Phe Asp
            100                 105                 110

Glu Phe Pro Trp Met Phe Gly Gly Gly Thr Lys Leu Glu Ile Lys Arg
        115                 120                 125

Ala Asp Ala Ala Pro Thr Val Ser Ile Phe Pro Pro Ser Ser
    130                 135                 140
```

(2) INFORMATION FOR SEQ ID NO: 3:

(i) SEQUENCE CHARACTERISTICS:
(A) LENGTH: 462 base pairs
(B) TYPE: nucleic acid
(C) STRANDEDNESS: single
(D) TOPOLOGY: linear (ix) FEATURE:
(A) NAME/KEY: CDS
(B) LOCATION: 22..462

(xi) SEQUENCE DESCRIPTION: SEQ ID NO: 3:

```
AGTCATATGG ATTGGGAATT C ATG GAA TGG AGC TGG GTC ATT CTC TTC CTC        51
                        Met Glu Trp Ser Trp Val Ile Leu Phe Leu
                         1               5                  10

CTG TCA GGA ACT GCA GGT GTC CAC TCT GAG GTC CAG CTG CAA CAG TCT        99
Leu Ser Gly Thr Ala Gly Val His Ser Glu Val Gln Leu Gln Gln Ser
                 15                  20                  25

GGA CCT GAG CTG GTG AAG CCT GGA GCT TCA CTG AAG ATT TCC TGC GAG       147
Gly Pro Glu Leu Val Lys Pro Gly Ala Ser Leu Lys Ile Ser Cys Glu
             30                  35                  40

GCT TCT GGT TAC TCA CTC ACT GCC TAC ACC ATG AAC TGG GTG AAG CAG       195
Ala Ser Gly Tyr Ser Leu Thr Ala Tyr Thr Met Asn Trp Val Lys Gln
         45                  50                  55

AGC CAT GGA AAG AGC CTT GAG TGG GTT GGG CTG ATT AAT CCT TTC AGT       243
Ser His Gly Lys Ser Leu Glu Trp Val Gly Leu Ile Asn Pro Phe Ser
     60                  65                  70

GGT GAT ACT AAC TAC AGC CAG AAA TTC ACG GGC AAG GCC ACA TTA ACT       291
Gly Asp Thr Asn Tyr Ser Gln Lys Phe Thr Gly Lys Ala Thr Leu Thr
 75                  80                  85                  90
```

-continued

```
GTA GAC AGG TCA TCC AGC ACA GCC TAC ATG GAG CTC CTC AGT CTG ACA      339
Val Asp Arg Ser Ser Ser Thr Ala Tyr Met Glu Leu Leu Ser Leu Thr
                 95                 100                 105

TCT GAG GAC TCT GCA GTC TAT TAC TGT GTC ATT ACT CCG GTT CCC TAC      387
Ser Glu Asp Ser Ala Val Tyr Tyr Cys Val Ile Thr Pro Val Pro Tyr
            110                 115                 120

TGG TAC TTC GAT GTC TGG GGC GCA GGG ACC ACG GTC ACC GTC TCC TCA      435
Trp Tyr Phe Asp Val Trp Gly Ala Gly Thr Thr Val Thr Val Ser Ser
        125                 130                 135

GCC AAA ACG ACA CCC CCA TCC GTC TAT                                  462
Ala Lys Thr Thr Pro Pro Ser Val Tyr
    140                 145
```

(2) INFORMATION FOR SEQ ID NO: 4:

(i) SEQUENCE CHARACTERISTICS:
(A) LENGTH: 147 amino acids
(B) TYPE: amino acid
(D) TOPOLOGY: linear (ii) MOLECULE TYPE: protein (xi) SEQUENCE DESCRIPTION: SEQ ID NO: 4:

```
Met Glu Trp Ser Trp Val Ile Leu Phe Leu Leu Ser Gly Thr Ala Gly
  1               5                  10                  15

Val His Ser Glu Val Gln Leu Gln Gln Ser Gly Pro Glu Leu Val Lys
             20                  25                  30

Pro Gly Ala Ser Leu Lys Ile Ser Cys Glu Ala Ser Gly Tyr Ser Leu
         35                  40                  45

Thr Ala Tyr Thr Met Asn Trp Val Lys Gln Ser His Gly Lys Ser Leu
     50                  55                  60

Glu Trp Val Gly Leu Ile Asn Pro Phe Ser Gly Asp Thr Asn Tyr Ser
 65                  70                  75                  80

Gln Lys Phe Thr Gly Lys Ala Thr Leu Thr Val Asp Arg Ser Ser Ser
                 85                  90                  95

Thr Ala Tyr Met Glu Leu Leu Ser Leu Thr Ser Glu Asp Ser Ala Val
            100                 105                 110

Tyr Tyr Cys Val Ile Thr Pro Val Pro Tyr Trp Tyr Phe Asp Val Trp
        115                 120                 125

Gly Ala Gly Thr Thr Val Thr Val Ser Ser Ala Lys Thr Thr Pro Pro
    130                 135                 140

Ser Val Tyr
145
```

(2) INFORMATION FOR SEQ ID NO: 5:

(i) SEQUENCE CHARACTERISTICS:
(A) LENGTH: 107 amino acids
(B) TYPE: amino acid
(C) STRANDEDNESS: single
(D) TOPOLOGY: linear (xi) SEQUENCE DESCRIPTION: SEQ ID NO: 5:

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Gly Tyr
            20                  25                  30

Leu Asn Trp Phe Gln Gln Glu Pro Gly Lys Ser Pro Lys Thr Leu Ile
        35                  40                  45
```

```
Tyr Arg Ala Asn Arg Leu Ile Asp Gly Val Pro Ser Arg Phe Ser Gly
    50                  55                  60

Ser Gly Ser Gly Gln Val Tyr Ser Leu Thr Ile Ser Ser Leu Glu Tyr
65                  70                  75                  80

Glu Asp Met Gly Thr Tyr Tyr Cys Leu Gln Phe Asp Glu Phe Pro Trp
                85                  90                  95

Met Phe Gly Gly Gly Thr Lys Leu Glu Ile Lys
            100                 105
```

(2) INFORMATION FOR SEQ ID NO: 6:

(i) SEQUENCE CHARACTERISTICS:
(A) LENGTH: 119 amino acids
(B) TYPE: amino acid
(C) STRANDEDNESS: single
(D) TOPOLOGY: linear (xi) SEQUENCE DESCRIPTION: SEQ ID NO: 6:

```
Glu Val Gln Leu Gln Gln Ser Gly Pro Glu Leu Val Lys Pro Gly Ala
1               5                   10                  15

Ser Leu Lys Ile Ser Cys Glu Ala Ser Gly Tyr Ser Leu Thr Ala Tyr
            20                  25                  30

Thr Met Asn Trp Val Lys Gln Ser His Gly Lys Ser Leu Glu Trp Val
        35                  40                  45

Gly Leu Ile Asn Pro Phe Ser Gly Asp Thr Asn Tyr Ser Gln Lys Phe
    50                  55                  60

Thr Gly Lys Ala Thr Leu Thr Val Asp Arg Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Val Ile Thr Pro Val Pro Tyr Trp Tyr Phe Asp Val Trp Gly Ala Gly
            100                 105                 110

Thr Thr Val Thr Val Ser Ser
        115
```

(2) INFORMATION FOR SEQ ID NO: 7:

(i) SEQUENCE CHARACTERISTICS:
(A) LENGTH: 472 base pairs
(B) TYPE: nucleic acid
(C) STRANDEDNESS: single
(D) TOPOLOGY: linear (xi) SEQUENCE DESCRIPTION: SEQ ID NO: 7:

```
TGTGTGTCTG TATATAACAT AACTGTTTAC ACATAATACA CTGAAATGGA GCCCTTCCTT     60

GTTACTTCAT ACCATCCTCT GTGCTTCCTT CCTCAGGGGC TGATGCTGCA CCAACTGTAT    120

CCATCTTCCC ACCATCCAGT GAGCAGTTAA CATCTGGAGG TGCCTCAGTC GTGTGCTTCT    180

TGAACAACTT CTACCCCAAA GACATCAATG TCAAGTGGAA GATTGATGGC AGTGAACGAC    240

AAAATGGCGT CCTGAACAGT TGGACTGATC AGGACAGCAA AGACAGCACC TACAGCATGA    300

GCAGCACCCT CACGTTGACC AAGGACGAGT ATGAACGACA TAACAGCTAT ACCTGTGAGG    360

CCACTCACAA GACATCAACT TCACCCATTG TCAAGAGCTT CAACAGGAAT GAGTGTTAGA    420

GACAAAGGTC CTGAGACGCC ACCACCAGCT CCCCAGCTCC ATCCTATCTT CC            472
```

```
(2) INFORMATION FOR SEQ ID NO: 8:

     (i) SEQUENCE CHARACTERISTICS:
          (A) LENGTH: 1800 base pairs
          (B) TYPE: nucleic acid
          (C) STRANDEDNESS: single
          (D) TOPOLOGY: linear

    (ix) FEATURE:
          (A) NAME/KEY: CDS
          (B) LOCATION: join(99..389, 746..784, 883..1203, 1325..1645)

    (xi) SEQUENCE DESCRIPTION: SEQ ID NO: 8:

TCGGGGACAT GGGAAGGGTG CAAAAGTAGC GGCCTTCTAG AAGGTTTGGA CCTGTCCTGT     60

CCTGTCCGAC AGTGTAATCA CATATACTTT TTCTTGTA GCC AAA ACG ACA CCC       113
                                          Ala Lys Thr Thr Pro
                                            1               5

CCA TCT GTC TAT CCA CTG GCC CCT GGA TCT GCT GCC CAA ACT AAC TCC     161
Pro Ser Val Tyr Pro Leu Ala Pro Gly Ser Ala Ala Gln Thr Asn Ser
                 10                  15                  20

ATG GTG ACC CTG GGA TGC CTG GTC AAG GGC TAT TTC CCT GAG CCA GTG     209
Met Val Thr Leu Gly Cys Leu Val Lys Gly Tyr Phe Pro Glu Pro Val
             25                  30                  35

ACA GTG ACC TGG AAC TCT GGA TCC CTG TCC AGC GGT GTG CAC ACC TTC     257
Thr Val Thr Trp Asn Ser Gly Ser Leu Ser Ser Gly Val His Thr Phe
         40                  45                  50

CCA GCT GTC CTG CAG TCT GAC CTC TAC ACT CTG AGC AGC TCA GTG ACT     305
Pro Ala Val Leu Gln Ser Asp Leu Tyr Thr Leu Ser Ser Ser Val Thr
     55                  60                  65

GTC CCC TCC AGC CCT CGG CCC AGC GAG ACC GTC ACC TGC AAC GTT GCC     353
Val Pro Ser Ser Pro Arg Pro Ser Glu Thr Val Thr Cys Asn Val Ala
 70                  75                  80                  85

CAC CCG GCC AGC AGC ACC AAG GTG GAC AAG AAA ATT GGTGAGAGGA          399
His Pro Ala Ser Ser Thr Lys Val Asp Lys Lys Ile
                 90                  95

CATATAGGGA GGAGGGGTTC ACTAGAAGTG AGGCTCAAGC CATTAGCCTG CCTAAACCAA    459

CCAGGCTGGA CAGCCAACCA ACCAGGAAAT GGATCTCAGC CCAGAAGATC AAAAGTTGTT    519

CTTCTCCCTT CTGGAGATTT CTATGTCCTT TACAACTCAA TTGGTTAATA TCCTGGGTTG    579

GAGTCCCACA CATCTTGACA AACAGAGACA AATTTGAGTA TCACCAGCCA AAAGTCATAC    639

CCAAAAACAG CCTGGCATGA CCACACACCA GACTCAAACT TACCCTACCT TTATCCTGGT    699

GGCTTCTCAT CTCCAGACCC CAGTAACACA TAGCTTTCTC TCCACA GTG CCC AGG      754
                                                   Val Pro Arg
                                                           100

GAT TGT GGT TGT AAG CCT TGC ATA TGT ACA GGTAAGTCAG TGGCCTTCAC       804
Asp Cys Gly Cys Lys Pro Cys Ile Cys Thr
                105                 110

CTGACCCAGA TGCAACAAGT GGCAATGTTG GAGGGTGGCC AGGTATTGAC CTATTTCCAC    864

CTTTCTTCTT CATCCTTA GTC CCA GAA GTA TCA TCT GTC TTC ATC TTC CCC     915
                    Val Pro Glu Val Ser Ser Val Phe Ile Phe Pro
                                    115                 120

CCA AAG CCC AAG GAT GTG CTC ACC ATT ACT CTG ACT CCT AAG GTC ACG     963
Pro Lys Pro Lys Asp Val Leu Thr Ile Thr Leu Thr Pro Lys Val Thr
            125                 130                 135

TGT GTT GTG GTA GAC ATC AGC AAG GAT GAT CCC GAG GTC CAG TTC AGC    1011
Cys Val Val Val Asp Ile Ser Lys Asp Asp Pro Glu Val Gln Phe Ser
        140                 145                 150

TGG TTT GTA GAT GAT GTG GAG GTG CAC ACA GCT CAG ACG CAA CCC CGG    1059
Trp Phe Val Asp Asp Val Glu Val His Thr Ala Gln Thr Gln Pro Arg
    155                 160                 165
```

-continued

```
GAG GAG CAG TTC AAC AGC ACT TTC CGC TCA GTC AGT GAA CTT CCC ATC      1107
Glu Glu Gln Phe Asn Ser Thr Phe Arg Ser Val Ser Glu Leu Pro Ile
170                 175                 180                 185

ATG CAC CAG GAC TGG CTC AAT GGC AAG GAG TTC AAA TGC AGG GTC AAC      1155
Met His Gln Asp Trp Leu Asn Gly Lys Glu Phe Lys Cys Arg Val Asn
                190                 195                 200

AGT GCA GCT TTC CCT GCC CCC ATC GAG AAA ACC ATC TCC AAA ACC AAA      1203
Ser Ala Ala Phe Pro Ala Pro Ile Glu Lys Thr Ile Ser Lys Thr Lys
            205                 210                 215

GGTGAGAGCT GCAGTGTGTG ACATAGAAGC TGCAATAGTC AGTCCATAGA CAGAGCTTGG   1263

CATAACAGAC CCCTGCCCTG TTCGTGACCT CTGTGCTGAC CAATCTCTTT ACCCACCCAC   1323

A GGC AGA CCG AAG GCT CCA CAG GTG TAC ACC ATT CCA CCT CCC AAG       1369
  Gly Arg Pro Lys Ala Pro Gln Val Tyr Thr Ile Pro Pro Pro Lys
          220                 225                 230

GAG CAG ATG GCC AAG GAT AAA GTC AGT CTG ACC TGC ATG ATA ACA GAC      1417
Glu Gln Met Ala Lys Asp Lys Val Ser Leu Thr Cys Met Ile Thr Asp
        235                 240                 245

TTC TTC CCT GAA GAC ATT ACT GTG GAG TGG CAG TGG AAT GGG CAG CCA      1465
Phe Phe Pro Glu Asp Ile Thr Val Glu Trp Gln Trp Asn Gly Gln Pro
    250                 255                 260

GCG GAG AAC TAC AAG AAC ACT CAG CCC ATC ATG AAC ACG AAT GGC TCT      1513
Ala Glu Asn Tyr Lys Asn Thr Gln Pro Ile Met Asn Thr Asn Gly Ser
265                 270                 275                 280

TAC TTC GTC TAC AGC AAG CTC AAT GTG CAG AAG AGC AAC TGG GAG GCA      1561
Tyr Phe Val Tyr Ser Lys Leu Asn Val Gln Lys Ser Asn Trp Glu Ala
                285                 290                 295

GGA AAT ACT TTC ACC TGC TCT GTG TTA CAT GAG GGC CTG CAC AAC CAC      1609
Gly Asn Thr Phe Thr Cys Ser Val Leu His Glu Gly Leu His Asn His
            300                 305                 310

CAT ACT GAG AAG AGC CTC TCC CAC TCT CCT GGT AAA TGATCCCAGT          1655
His Thr Glu Lys Ser Leu Ser His Ser Pro Gly Lys
        315                 320

GTCCTTGGAG CCCTCTGGTC CTACAGGACT CTGACACCTA CCTCCACCCC TCCCTGTATA   1715

AATAAAGCAC CCAGCACTGC CTTGGGACCC TGCAATAACG TCCTGGTGAT TTCTGAGATG   1775

TAGAGTCTAG CTAGGTCATG GAATG                                         1800
```

(2) INFORMATION FOR SEQ ID NO: 9:

(i) SEQUENCE CHARACTERISTICS:
(A) LENGTH: 324 amino acids
(B) TYPE: amino acid
(D) TOPOLOGY: linear (ii) MOLECULE TYPE: protein (xi) SEQUENCE DESCRIPTION: SEQ ID NO: 9:

```
Ala Lys Thr Thr Pro Pro Ser Val Tyr Pro Leu Ala Pro Gly Ser Ala
  1               5                  10                  15

Ala Gln Thr Asn Ser Met Val Thr Leu Gly Cys Leu Val Lys Gly Tyr
             20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
     50                  55                  60

Ser Ser Ser Val Thr Val Pro Ser Ser Pro Arg Pro Ser Glu Thr Val
 65                  70                  75                  80

Thr Cys Asn Val Ala His Pro Ala Ser Ser Thr Lys Val Asp Lys Lys
                 85                  90                  95
```

-continued

```
Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asn Thr Asn Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys
```

(2) INFORMATION FOR SEQ ID NO: 10:

(i) SEQUENCE CHARACTERISTICS:
(A) LENGTH: 320 amino acids
(B) TYPE: amino acid
(C) STRANDEDNESS: single
(D) TOPOLOGY: linear (xi) SEQUENCE DESCRIPTION: SEQ ID NO: 10:

```
Ala Lys Thr Thr Pro Pro Thr Val Tyr Pro Leu Ala Pro Gly Ser Asn
1               5                   10                  15

Ala Ala Ser Gln Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Lys Leu Tyr Thr Leu
    50                  55                  60

Ser Ser Ser Val Ser Val Pro Thr Ser Pro Glu Thr Val Thr Cys Asn
65                  70                  75                  80

Val Ala His Ala Pro Ser Ser Thr Lys Val Asp Lys Lys Ile Val Pro
                85                  90                  95

Arg Asp Cys Gly Cys Lys Pro Cys Ile Cys Thr Val Pro Glu Val Ser
            100                 105                 110

Ser Val Phe Ile Phe Pro Pro Lys Pro Lys Asp Thr Leu Leu Ile Thr
        115                 120                 125
```

-continued

```
Val Thr Pro Lys Val Thr Cys Val Val Val Asp Ile Ser Lys Asp Asp
    130                 135                 140

Pro Glu Val Gln Phe Ser Trp Phe Val Asp Asn Val Glu Val His Thr
145                 150                 155                 160

Ala Gln Thr Gln Pro Arg Glu Glu Gln Phe Asn Ser Thr Phe Arg Val
                165                 170                 175

Val Ser Ala Leu Pro Ile Met His Gln Asp Trp Leu Asn Gly Lys Glu
            180                 185                 190

Phe Lys Cys Arg Val Asn Ser Ala Ala Phe Pro Ala Pro Ile Glu Lys
        195                 200                 205

Thr Ile Ser Lys Thr Lys Gly Lys Pro Arg Ala Pro Gln Val Tyr Thr
    210                 215                 220

Ile Pro Pro Pro Lys Glu Gln Met Ala Lys Asp Lys Val Ser Leu Thr
225                 230                 235                 240

Cys Met Ile Thr Asp Phe Phe Pro Glu Asp Ile Thr Val Glu Trp Gln
                245                 250                 255

Ser Asp Gly Gln Ala Pro Glu Asn Tyr Lys Asn Thr Gln Pro Ile Met
            260                 265                 270

Asp Thr Asp Gly Ser Tyr Phe Val Tyr Ser Lys Leu Asn Val Gln Lys
        275                 280                 285

Ser Asn Trp Glu Ala Gly Asn Thr Phe Thr Cys Ser Val Leu His Glu
    290                 295                 300

Gly Leu His Asn His His Thr Glu Lys Ser Leu Ser Met Ser Pro Gly
305                 310                 315                 320
```

(2) INFORMATION FOR SEQ ID NO: 11:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 11:

```
Ile Tyr Arg Ala Asn Arg Leu Ile Asp Gly Val
1               5                   10
```

(2) INFORMATION FOR SEQ ID NO: 12:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: 1..9
(D) OTHER INFORMATION: /note= "Residues 29-37 of SEQ ID NO:6"

(xi) SEQUENCE DESCRIPTION: SEQ ID NO: 12:

```
Leu Thr Ala Tyr Thr Met Asn Trp Val
1               5
```

-continued (2) INFORMATION FOR SEQ ID NO: 13:

(i) SEQUENCE CHARACTERISTICS:
(A) LENGTH: 13 amino acids
(B) TYPE: amino acid
(C) STRANDEDNESS: single
(D) TOPOLOGY: linear (xi) SEQUENCE DESCRIPTION: SEQ ID NO: 13:

```
Ala Thr Pro Gly Pro Ala Tyr Ser Gly Arg Glu Ile Ile
1               5                   10
```

(2) INFORMATION FOR SEQ ID NO: 14:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: 1..11
(D) OTHER INFORMATION: /note= "Residues 24-34 of SEQ ID NO:5"

(xi) SEQUENCE DESCRIPTION: SEQ ID NO: 14:

```
Lys Ala Ser Gln Asp Ile Asn Gly Tyr Leu Asn
1               5                   10
```

(2) INFORMATION FOR SEQ ID NO: 15:

(i) SEQUENCE CHARACTERISTICS:
(A) LENGTH: 15 amino acids
(B) TYPE: amino acid
(C) STRANDEDNESS: single
(D) TOPOLOGY: linear (xi) SEQUENCE DESCRIPTION: SEQ ID NO: 15:

```
Pro Gln Tyr Ser Trp Arg Ile Asn Gly Ile Pro Gln Gln His Thr
1               5                   10                  15
```

(2) INFORMATION FOR SEQ ID NO: 16:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: 1..13
(D) OTHER INFORMATION: /note= "Residues 46-58 of SEQ ID NO:5"

(xi) SEQUENCE DESCRIPTION: SEQ ID NO: 16:

```
Thr Leu Ile Tyr Arg Ala Asn Arg Leu Ile Asp Gly Val
1               5                   10
```

(2) INFORMATION FOR SEQ ID NO: 17:

(i) SEQUENCE CHARACTERISTICS:
(A) LENGTH: 17 amino acids
(B) TYPE: amino acid
(C) STRANDEDNESS: single
(D) TOPOLOGY: linear (xi) SEQUENCE DESCRIPTION: SEQ ID NO: 17:

```
Ser Asn Pro Pro Ala Gln Tyr Ser Trp Leu Ile Asp Gly Asn Ile Gln
1               5                   10                  15

Gln
```

(2) INFORMATION FOR SEQ ID NO: 18:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: 1..6
(D) OTHER INFORMATION: /note= "Residues 9-14 of SEQ ID NO:6"

(xi) SEQUENCE DESCRIPTION: SEQ ID NO: 18:

```
Pro Glu Leu Val Lys Pro
1               5
```

(2) INFORMATION FOR SEQ ID NO: 19:

(i) SEQUENCE CHARACTERISTICS:
(A) LENGTH: 20 amino acids
(B) TYPE: amino acid
(C) STRANDEDNESS: single
(D) TOPOLOGY: linear (xi) SEQUENCE DESCRIPTION: SEQ ID NO: 19:

```
Phe Arg Val Tyr Pro Glu Leu Pro Lys Pro Ser Ile Ser Ser Asn Asn
1               5                   10                  15

Ser Lys Pro Val
            20
```

(2) INFORMATION FOR SEQ ID NO: 20:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: 1..4
(D) OTHER INFORMATION: /note= "Residues 16-19 of SEQ ID NO:5"

(xi) SEQUENCE DESCRIPTION: SEQ ID NO: 20:

```
Gly Glu Arg Val
1
```

(2) INFORMATION FOR SEQ ID NO: 21:

(i) SEQUENCE CHARACTERISTICS:
(A) LENGTH: 15 amino acids
(B) TYPE: amino acid
(C) STRANDEDNESS: single
(D) TOPOLOGY: linear (ix) FEATURE:
(A) NAME/KEY: Region
(B) LOCATION: 1..15
(D) OTHER INFORMATION: /note= "Residues 12-26 of SEQ ID NO:5"

(xi) SEQUENCE DESCRIPTION: SEQ ID NO: 21:

Tyr Ala Ser Leu Gly Glu Arg Val Thr Ile Thr Cys Lys Ala Ser
1 5 10 15

(2) INFORMATION FOR SEQ ID NO: 22:

(i) SEQUENCE CHARACTERISTICS:
(A) LENGTH: 15 amino acids
(B) TYPE: amino acid
(C) STRANDEDNESS: single
(D) TOPOLOGY: linear (xi) SEQUENCE DESCRIPTION: SEQ ID NO: 22:

Ser Trp Tyr Lys Gly Glu Arg Val Asp Gly Asn Arg Gln Ile Ile
1 5 10 15

(2) INFORMATION FOR SEQ ID NO: 23:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: 1..17
(D) OTHER INFORMATION: /note= "Residues 66-50 of SEQ ID NO:6"

(xi) SEQUENCE DESCRIPTION: SEQ ID NO: 23:

Gly Thr Phe Lys Gln Ser Tyr Asn Thr Asp Gly Ser Phe Pro Asn Ile
1 5 10 15

Leu (2) INFORMATION FOR SEQ ID NO: 24:

(i) SEQUENCE CHARACTERISTICS:
(A) LENGTH: 19 amino acids
(B) TYPE: amino acid
(C) STRANDEDNESS: single
(D) TOPOLOGY: linear (xi) SEQUENCE DESCRIPTION: SEQ ID NO: 24:

Phe Val Asn Gly Thr Phe Gln Gln Ser Thr Gln Glu Leu Phe Ile Pro
1 5 10 15

Asn Ile Thr (2) INFORMATION FOR SEQ ID NO: 25:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: 1..11
(D) OTHER INFORMATION: /note= "Residues 34-24 of SEQ ID NO:5"

(xi) SEQUENCE DESCRIPTION: SEQ ID NO: 25:

```
Asn Leu Tyr Gly Asn Ile Asp Gln Ser Ala Lys
1               5                   10
```

(2) INFORMATION FOR SEQ ID NO: 26:

(i) SEQUENCE CHARACTERISTICS:
(A) LENGTH: 13 amino acids
(B) TYPE: amino acid
(C) STRANDEDNESS: single
(D) TOPOLOGY: linear (xi) SEQUENCE DESCRIPTION: SEQ ID NO: 26:

```
Leu Asp Val Leu Tyr Gly Pro Asp Thr Pro Ile Ile Ser
1               5                   10
```

(2) INFORMATION FOR SEQ ID NO: 27:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: 1..5
(D) OTHER INFORMATION: /note= "Residues 35-31 of SEQ ID NO:6"

(xi) SEQUENCE DESCRIPTION: SEQ ID NO: 27:

```
Asn Met Thr Tyr Ala
1               5
```

(2) INFORMATION FOR SEQ ID NO: 28:

(i) SEQUENCE CHARACTERISTICS:
(A) LENGTH: 14 amino acids
(B) TYPE: amino acid
(C) STRANDEDNESS: single
(D) TOPOLOGY: linear (xi) SEQUENCE DESCRIPTION: SEQ ID NO: 28:

```
Pro Asn Asn Asn Gly Thr Tyr Ala Cys Phe Val Ser Asn Leu
1               5                   10
```

(2) INFORMATION FOR SEQ ID NO: 29:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO: 29:

```
Leu Ile Asp Gly Pro
1               5
```

(2) INFORMATION FOR SEQ ID NO: 30:

(i) SEQUENCE CHARACTERISTICS:
(A) LENGTH: 6 amino acids
(B) TYPE: amino acid
(C) STRANDEDNESS: single
(D) TOPOLOGY: linear (xi) SEQUENCE DESCRIPTION: SEQ ID NO: 30:

```
Phe Val Asn Thr Phe Ser
1               5
```

(2) INFORMATION FOR SEQ ID NO: 31:

(i) SEQUENCE CHARACTERISTICS:
(A) LENGTH: 18 amino acids
(B) TYPE: amino acid
(C) STRANDEDNESS: single
(D) TOPOLOGY: linear (xi) SEQUENCE DESCRIPTION: SEQ ID NO: 31:

```
Ser Asn Pro Pro Ala Gln Tyr Ser Trp Leu Ile Asp Gly Asn Ile Gln
1               5                   10                  15

Gln His
```

(2) INFORMATION FOR SEQ ID NO: 32:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO: 32:

```
Ser Pro Arg Ile Pro
1               5
```

(2) INFORMATION FOR SEQ ID NO: 33:

(i) SEQUENCE CHARACTERISTICS:
(A) LENGTH: 18 amino acids
(B) TYPE: amino acid
(C) STRANDEDNESS: single
(D) TOPOLOGY: linear (ix) FEATURE:
(A) NAME/KEY: Region
(B) LOCATION: 1..18
(D) OTHER INFORMATION: /note= "Residues 97-80 of SEQ ID NO:4"

(ix) FEATURE:
(A) NAME/KEY: Region
(B) LOCATION: 1..18
(D) OTHER INFORMATION: /note= "Residues 78-61 of SEQ ID NO:6"

(xi) SEQUENCE DESCRIPTION: SEQ ID NO: 33:

```
Thr Ser Ser Ser Arg Asp Val Thr Leu Thr Ala Lys Gly Thr Phe Lys
1               5                   10                  15

Gln Ser
```

(2) INFORMATION FOR SEQ ID NO: 34:

(i) SEQUENCE CHARACTERISTICS:
(A) LENGTH: 17 amino acids
(B) TYPE: amino acid
(C) STRANDEDNESS: single
(D) TOPOLOGY: linear -continued (xi) SEQUENCE DESCRIPTION: SEQ ID NO: 34:

Val Thr Ile Thr Cys Lys Ala Ser Gln Asp Ile Asn Gly Tyr Leu Asn
1 5 10 15

Trp (2) INFORMATION FOR SEQ ID NO: 35:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 35:

Ile Tyr Arg Ala Asn Arg Leu Ile Asp Gly Val
1 5 10

(2) INFORMATION FOR SEQ ID NO: 36:

(i) SEQUENCE CHARACTERISTICS:
(A) LENGTH: 34 base pairs
(B) TYPE: nucleic acid
(C) STRANDEDNESS: single
(D) TOPOLOGY: linear (xi) SEQUENCE DESCRIPTION: SEQ ID NO: 36:

GGGAATTCAT GRAATGSASC TGGGTYWTYC TCTT 34

(2) INFORMATION FOR SEQ ID NO: 37:

(i) SEQUENCE CHARACTERISTICS:
(A) LENGTH: 35 base pairs
(B) TYPE: nucleic acid
(C) STRANDEDNESS: single
(D) TOPOLOGY: linear (ix) FEATURE:
(A) NAME/KEY: misc_feature
(B) LOCATION: 6
(D) OTHER INFORMATION: /note= "N represents Inosine"

(xi) SEQUENCE DESCRIPTION: SEQ ID NO: 37:

GGTRGNCARA TAGGKRACCR GGGACCTTCG AACCC 35

(2) INFORMATION FOR SEQ ID NO: 38:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 38:

TAATACGACT CACTATAGGG 20

(2) INFORMATION FOR SEQ ID NO: 39:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO: 39:

CTTTTCCCAG TCACGACGT 19

-continued (2) INFORMATION FOR SEQ ID NO: 40:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO: 40:

ACTAGTCGAC ATGGTRTCCW CASCTCAGTT CCTTG 35

(2) INFORMATION FOR SEQ ID NO: 41:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO: 41:

CCCAAGCTTA CTGGATGGTG GGAAGATGGA 30

(2) INFORMATION FOR SEQ ID NO: 42:

(i) SEQUENCE CHARACTERISTICS:
(A) LENGTH: 15 amino acids
(B) TYPE: amino acid
(C) STRANDEDNESS: single
(D) TOPOLOGY: linear (xi) SEQUENCE DESCRIPTION: SEQ ID NO: 42:

Xaa Val Gln Leu Gln Gln Ser Gly Pro Glu Leu Val Lys Pro Gly
1 5 10 15

(2) INFORMATION FOR SEQ ID NO: 43:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 43:

CAGATGGAAG GGCCCAAC 18

(2) INFORMATION FOR SEQ ID NO: 44:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 44:

GATTGATGCA TATCATTACC 20

(2) INFORMATION FOR SEQ ID NO: 45:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 45:

GTTATCGATG TCGAATAGCC 20

(2) INFORMATION FOR SEQ ID NO: 46:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 46:

TTGCTGCAGA TTGAGTACTG TTCT 24

(2) INFORMATION FOR SEQ ID NO: 47:

(i) SEQUENCE CHARACTERISTICS:
(A) LENGTH: 8 amino acids
(B) TYPE: amino acids
(C) STRANDEDNESS: single
(D) TOPOLOGY: linear (xi) SEQUENCE DESCRIPTION: SEQ ID NO: 47:

```
Arg Ala Asn Arg Leu Ile Asp Gly
 1               5
```

(2) INFORMATION FOR SEQ ID NO: 48:

(i) SEQUENCE CHARACTERISTICS:
(A) LENGTH: 4 amino acids
(B) TYPE: amino acids
(C) STRANDEDNESS: single
(D) TOPOLOGY: linear (xi) SEQUENCE DESCRIPTION: SEQ ID NO: 48:

```
Leu Ile Asp Gly
 1
```

(2) INFORMATION FOR SEQ ID NO: 49:

(i) SEQUENCE CHARACTERISTICS:
(A) LENGTH: 15 amino acids
(B) TYPE: amino acids
(C) STRANDEDNESS: single
(D) TOPOLOGY: linear (xi) SEQUENCE DESCRIPTION: SEQ ID NO: 49:

```
Gly Gly Gly Gly Ser Gly Gly Gly Gly Ser Gly Gly Gly Gly Ser
 1               5                  10                  15
```

(2) INFORMATION FOR SEQ ID NO: 50:

(i) SEQUENCE CHARACTERISTICS:
(A) LENGTH: 7 amino acids
(B) TYPE: amino acids
(C) STRANDEDNESS: single
(D) TOPOLOGY: linear (xi) SEQUENCE DESCRIPTION: SEQ ID NO: 50:

```
Arg Ala Asn Arg Leu Ile Asp
 1               5
```

(2) INFORMATION FOR SEQ ID NO: 51:

(i) SEQUENCE CHARACTERISTICS:
(A) LENGTH: 23 amino acids
(B) TYPE: amino acid
(C) STRANDEDNESS: single
(D) TOPOLOGY: linear -continued (xi) SEQUENCE DESCRIPTION: SEQ ID NO: 51:

```
Asp Ile Lys Met Thr Gln Ser Pro Ser Ser Met Tyr Ala Ser Leu Gly
1               5                   10                  15

Glu Arg Val Thr Ile Thr Cys
            20
```

(2) INFORMATION FOR SEQ ID NO: 52:

(i) SEQUENCE CHARACTERISTICS:
(A) LENGTH: 15 amino acids
(B) TYPE: amino acid
(C) STRANDEDNESS: single
(D) TOPOLOGY: linear (xi) SEQUENCE DESCRIPTION: SEQ ID NO: 52:

```
Trp Phe Gln Gln Glu Pro Gly Lys Ser Pro Lys Thr Leu Ile
1               5                   10

Tyr
15
```

(2) INFORMATION FOR SEQ ID NO: 53:

(i) SEQUENCE CHARACTERISTICS:
(A) LENGTH: 32 amino acids
(B) TYPE: amino acid
(C) STRANDEDNESS: single
(D) TOPOLOGY: linear (xi) SEQUENCE DESCRIPTION: SEQ ID NO: 53:

```
Gly Val Pro Ser Arg Phe Ser Gly Ser Gly Ser Gly Gln Val Tyr Ser
1               5                   10                  15

Leu Thr Ile Ser Ser Leu Glu Tyr Glu Asp Met Gly Thr Tyr Tyr Cys
            20                  25                  30
```

(2) INFORMATION FOR SEQ ID NO: 54:

(i) SEQUENCE CHARACTERISTICS:
(A) LENGTH: 9 amino acids
(B) TYPE: amino acid
(C) STRANDEDNESS: single
(D) TOPOLOGY: linear (xi) SEQUENCE DESCRIPTION: SEQ ID NO: 54:

```
Leu Gln Phe Asp Glu Phe Pro Trp Met
1               5
```

(2) INFORMATION FOR SEQ ID NO: 55:

(i) SEQUENCE CHARACTERISTICS:
(A) LENGTH: 10 amino acids
(B) TYPE: amino acid
(C) STRANDEDNESS: single
(D) TOPOLOGY: linear (xi) SEQUENCE DESCRIPTION: SEQ ID NO: 55:

```
Phe Gly Gly Gly Thr Lys Leu Glu Ile Lys
1               5                   10
```

(2) INFORMATION FOR SEQ ID NO: 56:

(i) SEQUENCE CHARACTERISTICS:
(A) LENGTH: 30 amino acids
(B) TYPE: amino acid
(C) STRANDEDNESS: single
(D) TOPOLOGY: linear (xi) SEQUENCE DESCRIPTION: SEQ ID NO: 56:

Glu Val Gln Leu Gln Gln Ser Gly Pro Glu Leu Val Lys Pro Gly Ala
1 5 10 15

Ser Leu Lys Ile Ser Cys Glu Ala Ser Gly Tyr Ser Leu Thr
20 25 30

(2) INFORMATION FOR SEQ ID NO: 57:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO: 57:

Ala Tyr Thr Met Asn
1 5

(2) INFORMATION FOR SEQ ID NO: 58:

(i) SEQUENCE CHARACTERISTICS:
(A) LENGTH: 14 amino acids
(B) TYPE: amino acid
(C) STRANDEDNESS: single
(D) TOPOLOGY: linear (xi) SEQUENCE DESCRIPTION: SEQ ID NO: 58:

Trp Val Lys Gln Ser His Gly Lys Ser Leu Glu Trp Val Gly
1 5 10

(2) INFORMATION FOR SEQ ID NO: 59:

(i) SEQUENCE CHARACTERISTICS:
(A) LENGTH: 17 amino acids
(B) TYPE: amino acid
(C) STRANDEDNESS: single
(D) TOPOLOGY: linear (xi) SEQUENCE DESCRIPTION: SEQ ID NO: 59:

Leu Ile Asn Pro Phe Ser Gly Asp Thr Asn Tyr Ser Gln Lys Phe Thr
1 5 10 15

Gly (2) INFORMATION FOR SEQ ID NO: 60:

(i) SEQUENCE CHARACTERISTICS:
(A) LENGTH: 32 amino acids
(B) TYPE: amino acid
(C) STRANDEDNESS: single
(D) TOPOLOGY: linear (xi) SEQUENCE DESCRIPTION: SEQ ID NO: 60:

Lys Ala Thr Leu Thr Val Asp Arg Ser Ser Ser Thr Ala Tyr Met Glu
1 5 10 15

Leu Leu Ser Leu Thr Ser Glu Asp Ser Ala Val Tyr Tyr Cys Val Ile
20 25 30

(2) INFORMATION FOR SEQ ID NO: 61:

(i) SEQUENCE CHARACTERISTICS:
(A) LENGTH: 10 amino acids
(B) TYPE: amino acid
(C) STRANDEDNESS: single
(D) TOPOLOGY: linear (xi) SEQUENCE DESCRIPTION: SEQ ID NO: 61:

```
Thr Pro Val Pro Tyr Trp Tyr Phe Asp Val
1               5                   10
```

(2) INFORMATION FOR SEQ ID NO: 62:

(i) SEQUENCE CHARACTERISTICS:
(A) LENGTH: 11 amino acids
(B) TYPE: amino acid
(C) STRANDEDNESS: single
(D) TOPOLOGY: linear (xi) SEQUENCE DESCRIPTION: SEQ ID NO: 62:

```
Trp Gly Ala Gly Thr Thr Val Thr Val Ser Ser
1               5                   10
```

(2) INFORMATION FOR SEQ ID NO: 63:

(i) SEQUENCE CHARACTERISTICS:
(A) LENGTH: 389 base pairs
(B) TYPE: nucleic acid
(C) STRANDEDNESS: single
(D) TOPOLOGY: linear (xi) SEQUENCE DESCRIPTION: SEQ ID NO: 63:

```
ACTGAAATGG AGCCCTTCCT TGTTACTTCA TACCATCCTC TGTGCTTCCT TCCTCAGGGG     60

CTGATGCTGC ACCAACTGTA TCCATCTTCC CACCATCCAG TGAGCAGTTA ACATCTGGAG    120

GTGCCTCAGT CGTGTGCTTC TTGAACAACT TCTACCCCAA AGACATCAAT GTCAAGTGGA    180

AGATTGATGG CAGTGAACGA CAAAATGGCG TCCTGAACAG TTGGACTGAT CAGGACAGCA    240

AAGACAGCAC CTACAGCATG AGCAGCACCC TCACGTTGAC CAAGGACGAG TATGAACGAC    300

ATAACAGCTA TACCTGTGAG GCCACTCACA AGACATCAAC TTCACCCATT GTCAAGAGCT    360

TCAACAGGAA TGAGTGTTAG AGACAAAGG                                      389
```

(2) INFORMATION FOR SEQ ID NO: 64:

(i) SEQUENCE CHARACTERISTICS:
(A) LENGTH: 387 base pairs
(B) TYPE: nucleic acid
(C) STRANDEDNESS: single
(D) TOPOLOGY: linear (xi) SEQUENCE DESCRIPTION: SEQ ID NO: 64:

```
ACTGAAATGG AGCCCTTCCT TGTTACTTCA TACCATCCTC TGTGCTTCCT TCCTCAGGGG     60

CTGATGCTGC ACCAACTGTA TCCATCTTCC CACCATCCAG TGAGCAGTTA ACATCTGGAG    120

GTGCCTCAGT CGTGTGCTTC TTGAACAACT TCTACCCCAA AGACATCAAT GTCAAGTGGA    180

AGATTGATGG CAGTGAACGA CAAAATGGCG TCCTGAACAG TTGGACTGAT CAGGACAGCA    240

AAGACAGCAC CTACAGCATG AGCAGCACCC TCACGTTGAC CAAGGACGAG TATGAACGAC    300

ATAACAGCTA TACCTGTGAG GCCACTCACA AGACATCAAC TTCACCCATT GTCAAGAGCT    360

TCAACAGGAA TGAGTGTTAG AGACAAA                                        387
```

(2) INFORMATION FOR SEQ ID NO: 65:

(i) SEQUENCE CHARACTERISTICS:
(A) LENGTH: 390 base pairs
(B) TYPE: nucleic acid
(C) STRANDEDNESS: single
(D) TOPOLOGY: linear (ix) FEATURE:
(A) NAME/KEY: misc_feature
(B) LOCATION: 32
(D) OTHER INFORMATION: /note= "n represents a,t,c, or g"

(xi) SEQUENCE DESCRIPTION: SEQ ID NO: 65:

```
TACACTGAAA TGGAGCCCTT CCTTGTTACT TNATACCATC CTCTGTGCTT CCTTCCTCAG     60

GGGCTGATGC TGCACCAACT GTATCCATCT TCCCACCATC CAGTGAGCAG TTAACATCTG    120

GAGGTGCCTC AGTCGTGTGC TTCTTGAACA ACTTCTACCC CAAAGACATC AATGTCAAGT    180

GGAAGATTGA TGGCAGTGAA CGACAAAATG GCGTCCTGAA CAGTTGGACT GATCAGGACA    240

GCAAAGACAG CACCTACAGC ATGAGCAGCA CCCTCACGTT GACCAAGGAC GAGTATGAAC    300

GACATAACAG CTATACCTGT GAGGCCACTC ACAAGACATC AACTTCACCC ATTGTCAAGA    360

GCTTCAACAG GAATGAGTGT TAGAGACAAA                                     390
```

(2) INFORMATION FOR SEQ ID NO: 66:

(i) SEQUENCE CHARACTERISTICS:
(A) LENGTH: 387 base pairs
(B) TYPE: nucleic acid
(C) STRANDEDNESS: single
(D) TOPOLOGY: linear (xi) SEQUENCE DESCRIPTION: SEQ ID NO: 66:

```
ACTGAAATGG AGCCCTTCCT TGTTACTTCA TACCATCCTC TGTGCTTCCT TCCTCAGGGG     60

CTGATGCTGC ACCAACTGTA TCCATCTTCC CACCATCCAG TGAGCAGTTA ACATCTGGAG    120

GTGCCTCAGT CGTGTGCTTC TTGAACAACT TCTACCCCAA AGACATCAAT GTCAAGTGGA    180

AGATTGATGG CAGTGAACGA CAAAATGGCG TCCTGAACAG TTGGACTGAT CAGGACAGCA    240

AAGACAGCAC CTACAGCATG AGCAGCACCC TCACGTTGAC CAAGGACGAG TATGAACGAC    300

ATAACAGCTA TACCTGTGAG GCCACTCACA AGACATCAAC TTCACCCATT GTCAAGAGCT    360

TCAACAGGAA TGAGTGTTAG AGACAAA                                        387
```

(2) INFORMATION FOR SEQ ID NO: 67:

(i) SEQUENCE CHARACTERISTICS:
(A) LENGTH: 386 base pairs
(B) TYPE: nucleic acid
(C) STRANDEDNESS: single
(D) TOPOLOGY: linear (ix) FEATURE:
(A) NAME/KEY: misc_feature
(B) LOCATION: 9, 17, 18, 25
(D) OTHER INFORMATION: /note= "n represents a,t,c, or g"

(xi) SEQUENCE DESCRIPTION: SEQ ID NO: 67:

```
GAAATGGANC CCTTCCNNGT TACTNCATAC CATCCTCTGT GCTTCCTTCC TCAGGGGCTG     60

ATGCTGCACC AACTGTATCC ATCTTCCCAC CATCCAGTGA GCAGTTAACA TCTGGAGGTG    120

CCTCAGTCGT GTGCTTCTTG AACAACTTCT ACCCCAAAGA CATCAATGTC AAGTGGAAGA    180

TTGATGGCAG TGAACGACAA AATGGCGTCC TGAACAGTTG GACTGATCAG GACAGCAAAG    240

ACAGCACCTA CAGCATGAGC AGCACCCTCA CGTTGACCAA GGACGAGTAT GAACGACATA    300

ACAGCTATAC CTGTGAGGCC ACTCACAAGA CATCAACTTC ACCCATTGTC AAGAGCTTCA    360

ACAGGAATGA GTGTTAGAGA CAAAGG                                         386
```

(2) INFORMATION FOR SEQ ID NO: 68:

(i) SEQUENCE CHARACTERISTICS:
(A) LENGTH: 392 base pairs
(B) TYPE: nucleic acid
(C) STRANDEDNESS: single
(D) TOPOLOGY: linear (xi) SEQUENCE DESCRIPTION: SEQ ID NO: 68:

```
AATACACTGA AATGGAGCCC TTCCTTGTTA CTTCATACCA TCCTCTGTGC TTCCTTCCTC     60

AGGGGCTGAT GCTGCACCAA CTGTATCCAT CTTCCCACCA TCCAGTGAGC AGTTAACATC    120

TGGAGGTGCC TCAGTCGTGT GCTTCTTGAA CAACTTCTAC CCCAAAGACA TCAATGTCAA    180

GTGGAAGATT GATGGCAGTG AACGACAAAA TGGCGTCCTG AACAGTTGGA CTGATCAGGA    240

CAGCAAAGAC AGCACCTACA GCATGAGCAG CACCCTCACG TTGACCAAGG ACGAGTATGA    300

ACGACATAAC AGCTATACCT GTGAGGCCAC TCACAAGACA TCAACTTCAC CCATTGTCAA    360

GAGCTTCAAC AGGAATGAGT GTTAGAGACA AA                                   392
```

(2) INFORMATION FOR SEQ ID NO: 69:

(i) SEQUENCE CHARACTERISTICS:
(A) LENGTH: 393 base pairs
(B) TYPE: nucleic acid
(C) STRANDEDNESS: single
(D) TOPOLOGY: linear (ix) FEATURE:
(A) NAME/KEY: misc_feature
(B) LOCATION: 15, 24, 30, 31, 32
(D) OTHER INFORMATION: /note= “n represents a,t,c, or g”

(xi) SEQUENCE DESCRIPTION: SEQ ID NO: 69:

```
TACACTGAAA TGGANCCCTT CCTNGTTACN NNATACCATC CTCTGTGCTT CCTTCCTCAG     60

GGGCTGATGC TGCACCAACT GTATCCATCT TCCCACCATC CAGTGAGCAG TTAACATCTG    120

GAGGTGCCTC AGTCGTGTGC TTCTTGAACA ACTTCTACCC CAAAGACATC AATGTCAAGT    180

GGAAGATTGA TGGCAGTGAA CGACAAAATG GCGTCCTGAA CAGTTGGACT GATCAGGACA    240

GCAAAGACAG CACCTACAGC ATGAGCAGCA CCCTCACGTT GACCAAGGAC GAGTATGAAC    300

GACATAACAG CTATACCTGT GAGGCCACTC ACAAGACATC AACTTCACCC ATTGTCAAGA    360

GCTTCAACAG GAATGAGTGT TAGAGACAAA GGT                                  393
```

(2) INFORMATION FOR SEQ ID NO: 70:

(i) SEQUENCE CHARACTERISTICS:
(A) LENGTH: 343 base pairs
(B) TYPE: nucleic acid
(C) STRANDEDNESS: single
(D) TOPOLOGY: linear (ix) FEATURE:
(A) NAME/KEY: misc_feature
(B) LOCATION: 168, 169, 172, 173, 174, 329, 332
(D) OTHER INFORMATION: /note= “n represents a,t,c, or g”

(xi) SEQUENCE DESCRIPTION: SEQ ID NO: 70:

```
CTTCCTTCCT CAGGGGCTGA TGCTGCACCA ACTGTATCCA TCTTCCCACC ATCCAGTGAG     60

CAGTTAACAT CTGGAGGTGC CTCAGTCGTG TGCTTCTTGA ACAACTTCTA CCCCAAAGAC    120

ATCAATGTCA AGTGGAAGAT TGATGGCAGT GAACGACAAA ATGGCGTNNT GNNNAGTTGG    180

ACTGATCAGG ACAGCAAAGA CAGCACCTAC AGCATGAGCA GCACCCTCAC GTTGACCAAG    240
```

GACGAGTATG AACGACATAA CAGCTATACC TGTGAGGCCA CTCACAAGAC ATCAACTTCA 300

CCCATCGTCA AGAGCTTCAA CAGGAATGNG TNTTAGAGAC AAA 343

(2) INFORMATION FOR SEQ ID NO: 71:

(i) SEQUENCE CHARACTERISTICS:
(A) LENGTH: 390 base pairs
(B) TYPE: nucleic acid
(C) STRANDEDNESS: single
(D) TOPOLOGY: linear (xi) SEQUENCE DESCRIPTION: SEQ ID NO: 71:

TACACTGAAA TGGAGCCCTT CCTTGTTACT TCATACCATC CTCTGTGCTT CCTTCCTCAG 60

GGGCTGATGC TGCACCAACT GTATCCATCT TCCCACCATC CAGTGAGCAG TTAACATCTG 120

GAGGTGCCTC AGTCGTGTGC TTCTTGAACA ACTTCTACCC CAAAGACATC AATGTCAAGT 180

GGAAGATTGA TGGCAGTGAA CGACAAAATG GCGTCCTGAA CAGTTGGACT GATCAGGACA 240

GCAAAGACAG CACCTACAGC ATGAGCAGCA CCCTCACGTT GACCAAGGAC GAGTATGAAC 300

GACATAACAG CTATACCTGT GAGGCCACTC ACAAGACATC AACTTCACCC ATCGTCAAGA 360

GCTTCAACAG GAATGAGTGT TAGAGACAAA 390

(2) INFORMATION FOR SEQ ID NO: 72:

(i) SEQUENCE CHARACTERISTICS:
(A) LENGTH: 328 base pairs
(B) TYPE: nucleic acid
(C) STRANDEDNESS: single
(D) TOPOLOGY: linear (ix) FEATURE:
(A) NAME/KEY: misc_feature
(B) LOCATION: 1, 2, 7, 104
(D) OTHER INFORMATION: /note= "n represents a,t,c, or g"

(xi) SEQUENCE DESCRIPTION: SEQ ID NO: 72:

NNTGATNCTG CACCAACTGT ATCCATCTTC CCACCATCCA GTGAGCAGTT AACATCTGGA 60

GGTGCCTCAG TCGTGTGCTT CTTGAACAAC TTCTACCCCA AAGNCATCAA TGTCAAGTGG 120

AAGATTGATG GCAGTGAACG ACAAAATGGC GTCCTGAACA GTTGGACTGA TCAGGACAGC 180

AAAGACAGCA CCTACAGCAT GAGCAGCACC CTCACGTTGA CCAAGGACGA GTATGAACGA 240

CATAACAGCT ATACCTGTGA GGCCACTCAC AAGACATCAA CTTCACCCAT CGTCAAGAGC 300

TTCAACAGGA ATGAGTGTTA GAGACAAA 328

(2) INFORMATION FOR SEQ ID NO: 73:

(i) SEQUENCE CHARACTERISTICS:
(A) LENGTH: 387 base pairs
(B) TYPE: nucleic acid
(C) STRANDEDNESS: single
(D) TOPOLOGY: linear (xi) SEQUENCE DESCRIPTION: SEQ ID NO: 73:

ACTGAAATGG AGCCCTTCCT TGTTACTTCA TACCATCCTC TGTGCTTCCT TCCTCAGGGG 60

CTGATGCTGC ACCAACTGTA TCCATCTTCC CACCATCCAG TGAGCAGTTA ACATCTGGAG 120

GTGCCTCAGT CGTGTGCTTC TTGAACAACT TCTACCCCAG AGACATCAAT GTCAAGTGGA 180

AGATTGATGG CAGTGAACGA CAAAATGGTG TCCTGAACAG TTGGACTGAT CAGGACAGCA 240

AAGACAGCAC CTACAGCATG AGCAGCACCC TCACATTGAC CAAGGACGAG TATGAACGAC 300

```
ATAACAGCTA TACCTGTGAG GCCACTCACA AGACATCAAC TTCACCCATC GTCAAGAGCT    360

TCAACAGGAA TGAGTGTTAG AGCCAAA                                        387
```

(2) INFORMATION FOR SEQ ID NO: 74:

(i) SEQUENCE CHARACTERISTICS:
(A) LENGTH: 452 base pairs
(B) TYPE: nucleic acid
(C) STRANDEDNESS: single
(D) TOPOLOGY: linear (xi) SEQUENCE DESCRIPTION: SEQ ID NO: 74:

```
AACTGTTTAC ACATAATACA CTGAAATGGA GCCCTTCCTT GTTACTTCAT ACCATCCTCT     60

GTGCTTCCTT CCTCAGGGGC TGATGCTGCA CCAACTGTAT CCATCTTCCC ACCATCCAGT    120

GAGCAGTTAA CATCTGGAGG TGCCTCAGTC GTGTGCTTCT TGAACAACTT CTACCCCAGA    180

GACATCAATG TCAAGTGGAA GATTGATGGC AGTGAACGAC AAAATGGTGT CCTGAACAGT    240

TGGACTGATC AGGACAGCAA AGACAGCACC TACAGCATGA GCAGCACCCT CACATTGACC    300

AAGGACGAGT ATGAACGACA TAACAGCTAT ACCTGTGAGG CCACTCACAA GACATCAACT    360

TCACCCATTG TCAAGAGCTT CAACAGGAAT GAGTGTTAGA GCCAAAGGTC CTGAGACGCC    420

ACCACCAGCT CCCCAGCTCC ATCCTATCTT CC                                  452
```

(2) INFORMATION FOR SEQ ID NO: 75:

(i) SEQUENCE CHARACTERISTICS:
(A) LENGTH: 440 base pairs
(B) TYPE: nucleic acid
(C) STRANDEDNESS: single
(D) TOPOLOGY: linear (xi) SEQUENCE DESCRIPTION: SEQ ID NO: 75:

```
GTCTATAACA TGCATAGCAC TGATTTTCCT TGTTACTTCA TACCATCCTC TGTGCTTCCT     60

TCCTCAGGGG CTGATGCTGC ACCAACTGTA TCTATCTTCC CACCATCCAC GGAACAGTTA    120

GCAACTGGAG GTGCCTCAGT CGTGTGCCTC ATGAACAACT TCTATCCCAG AGACATCAGT    180

GTCAAGTGGA AGATTGATGG CACTGAACGA CGAGATGGTG TCCTGGACAG TGTTACTGAT    240

CAGGACAGCA AAGACAGCAC GTACAGCATG AGCAGCACCC TCTCGTTGAC CAAGGCTGAC    300

TATGAAAGTC ATAACCTCTA TACCTGTGAG GTTGTTCATA AGACATCATC CTCACCCGTC    360

GTCAAGAGCT TCAACAGGAA TGAGTGTTAG ACCCAAAGGT CCTGAGGTGC CACCTGCTCC    420

CCAGCTCCTT CCAATCTTCC                                                440
```

(2) INFORMATION FOR SEQ ID NO: 76:

(i) SEQUENCE CHARACTERISTICS:
(A) LENGTH: 440 base pairs
(B) TYPE: nucleic acid
(C) STRANDEDNESS: single
(D) TOPOLOGY: linear (xi) SEQUENCE DESCRIPTION: SEQ ID NO: 76:

```
GTCTATAACA TGCATAGCAC TGATTTTCCT TGTTACTTCA TACCATCCTC TGCGCTTCCT     60

TCCTCAGGGG CTGATGCTGC ACCAACTGTA TCCATCTTCC CACCATCCAT GGAACAGTTA    120

ACATCTGGAG GTGCCACAGT CGTGTGCTTC GTGAACAACT TCTATCCCAG AGACATCAGT    180

GTCAAGTGGA AGATTGATGG CAGTGAACAA CGAGATGGTG TCCTGGACAG TGTTACTGAT    240

CAGGACAGCA AAGACAGCAC GTACAGCATG AGCAGCACCC TCTCGTTGAC CAAGGTTGAA    300
```

-continued

```
TATGAAAGGC ATAACCTCTA TACCTGTGAG GTTGTTCATA AGACATCATC CTCACCCGTC    360

GTCAAGAGCT TCAACAGGAA TGAGTGTTAG ACCCAAAGGT CCTGAGGTGC CACCTGCTCC    420

CCAGTTCCTT CCAATCTTCC                                                440
```